United States Patent
Mycek et al.

(10) Patent No.: US 11,076,784 B2
(45) Date of Patent: Aug. 3, 2021

(54) SYSTEM FOR ANALYZING TISSUE

(71) Applicant: The Regents of the University of Michigan, Ann Arbor, MI (US)

(72) Inventors: Mary-Ann Mycek, Ann Arbor, MI (US); Fan Wu, Greenbelt, MD (US); James M. Scheiman, Charlottesville, VA (US); Euisik Yoon, Ypsilanti, MI (US); William Lloyd, Farmington Hills, MI (US); Seung Yup Lee, Decatur, GA (US)

(73) Assignee: The regents of the University of Michigan, Ann Arbor, MI (US)

( * ) Notice: Subject to any disclaimer, the term of this patent is extended or adjusted under 35 U.S.C. 154(b) by 810 days.

(21) Appl. No.: 15/706,900

(22) Filed: Sep. 18, 2017

(65) Prior Publication Data

US 2018/0008172 A1   Jan. 11, 2018

Related U.S. Application Data

(63) Continuation-in-part of application No. PCT/US2016/023437, filed on Mar. 21, 2016.
(Continued)

(51) Int. Cl.
*A61B 5/1455* (2006.01)
*A61B 5/00* (2006.01)
(Continued)

(52) U.S. Cl.
CPC .......... *A61B 5/1455* (2013.01); *A61B 5/0084* (2013.01); *A61B 5/0261* (2013.01);
(Continued)

(58) Field of Classification Search
CPC . A61B 5/1455; A61B 5/1459; A61B 5/14503; A61B 5/14507; A61B 5/14514;
(Continued)

(56) References Cited

U.S. PATENT DOCUMENTS 6,174,291 B1   1/2001   McMahon et al.
6,564,087 B1   5/2003   Pitris et al.
(Continued)

FOREIGN PATENT DOCUMENTS

EP   1884211 A2   2/2008
WO   2004082468 A2   9/2004
(Continued)

OTHER PUBLICATIONS

All About Circuits (https://www.allaboutcircuits.com/textbook/direct-current/chpt-7/what-is-a-series-parallel-circuit/, Jun. 7, 2015).*
(Continued)

*Primary Examiner* — Carolyn A Pehlke
(74) *Attorney, Agent, or Firm* — Howard & Howard Attorneys PLLC

(57) ABSTRACT

A system for analyzing tissue includes a platform and an optical sensing unit coupled to the platform. The optical sensing unit has a detector and a plurality of light sources surrounding and electrically isolated from the detector. The optical sensing units obtain optical data for tissue analysis.

21 Claims, 43 Drawing Sheets
(4 of 43 Drawing Sheet(s) Filed in Color)

Related U.S. Application Data

(60) Provisional application No. 62/177,603, filed on Mar. 19, 2015.

(51) Int. Cl.
  *A61B 5/026* (2006.01)
  *G01N 33/543* (2006.01)

(52) U.S. Cl.
  CPC .......... *G01N 33/54366* (2013.01); *G06T 2207/30004* (2013.01)

(58) Field of Classification Search
  CPC ... A61B 5/0084; A61B 5/0082; A61B 5/0059; A61B 5/0071; A61B 5/0261; A61B 5/6847; A61B 5/6848; A61B 5/685; G01N 33/54366
  See application file for complete search history.

(56) References Cited

U.S. PATENT DOCUMENTS

| | | | |
|---|---|---|---|
| 8,666,479 | B2 | 3/2014 | Berndt |
| 8,694,266 | B2 | 4/2014 | Mycek et al. |
| 2004/0249268 | A1 | 12/2004 | Da Silva |
| 2005/0203419 | A1 | 9/2005 | Ramanujam et al. |
| 2005/0261568 | A1 | 11/2005 | Hular et al. |
| 2008/0009751 | A1 | 1/2008 | Berndt |
| 2008/0194969 | A1* | 8/2008 | Werahera ............ A61B 5/7267 600/476 |
| 2009/0180962 | A1 | 7/2009 | Black et al. |
| 2010/0081964 | A1 | 4/2010 | Mark et al. |
| 2011/0136132 | A1 | 6/2011 | Tseng et al. |
| 2011/0251494 | A1 | 10/2011 | Hendriks et al. |
| 2013/0149714 | A1 | 6/2013 | Scherer et al. |
| 2013/0267821 | A1* | 10/2013 | Hashimshony .... A61B 17/3205 600/407 |
| 2014/0171788 | A1 | 6/2014 | Stigall |
| 2015/0282713 | A1* | 10/2015 | Fei ....................... A61B 5/681 600/476 |
| 2016/0066789 | A1* | 3/2016 | Rogers ................... A61N 1/05 604/20 |
| 2017/0273671 | A1* | 9/2017 | Reich ................ A61B 10/0275 |

FOREIGN PATENT DOCUMENTS

| | | |
|---|---|---|
| WO | 2005087092 A1 | 9/2005 |
| WO | 2008008318 A2 | 1/2008 |
| WO | 2010058344 A1 | 5/2010 |
| WO | 2014068468 A1 | 5/2014 |

OTHER PUBLICATIONS

Visible light spectrum (http://hyperphysics.phy-astr.gsu.edu/hbase/vision/specol.html#c1, Aug. 7, 2013).*
DigChip (VishayT1090P spec sheet, https://www.digchip.com/datasheets/parts/datasheet/513/T1090P-SD-F.php, Mar. 2012).*
International Search Report for Application No. PCT/US2016/023437 dated Jun. 27, 2016, 3 pages.
Abraham, Susan C. et al., "Pancreaticoduodenectomy (Whipple Resections) in Patients Without Malignancy", The American Journal of Surgical Pathology, 27(1), 2003, pp. 110-120.
Amelink, A. et al., "Non-Invasive Measurement of the Microvascular Properties of Non-Dysplastic and Dysplastic Oral Leukoplakias by Use of Optical Spectroscopy", Oral Oncology, vol. 47, 2011, pp. 1165-1170.
American Cancer Society, "Cancer Facts and Figures 2013", 2013, pp. 1-62.
American Cancer Society, "Cancer Facts and Figures 2014", 2014, pp. 1-70.
American Cancer Society, "How Common Is Breast Cancer?", Jul. 1, 2017, 4 pages.
American Cancer Society, "Key Statistics for Lung Cancer", Feb. 8, 2016, 3 pages.
American Cancer Society, "Key Statistics for Prostate Cancer" Feb. 16, 2016, 3 pages.
Analog Devices, "AN-1212 Application Note", 2013, 2 pages.
Balthasar, MD, Andrea et al., "Optical Detection of Vascular Penetration During Nerve Blocks" An In Vivo Human Study, Regional Anethesia and Pain Medicine, vol. 37, No. 1, Jan.-Feb. 2012, pp. 3-7.
Balthasar, MD, Andrea et al., "Optical Detection of Peripheral Nerves: An In Vivo Human Study", Regional Anesthesia and Pain Medicine, vol. 37, No. 3, May-Jun. 2012., pp. 277-282.
Becker, Valentin et al., "Needle-Based Confocal Endomicroscopy for In Vivo Histology of Intra-Abdominal Organs: First Results in a Porcine Model (with Videos)", Gastrointestinal Endoscopy, vol. 71, No. 7, 2010, pp. 1260-1266.
Bigio, Irving J. et al., "Diagnosis of Breast Cancer Using Elastic-Scattering Spectroscopy: Preliminary Clinical Results", Journal of Biomedical Optics, vol. 5, No. 2, Apr. 2000, pp. 221-228.
Brown, J. Quincy et al., "Quantitative Optical Spectroscopy: A Robust Tool for Direct Measurement of Breast Cancer Vascular Oxygenation and Total Hemoglobin Content In Vivo", Cancer Res. vol. 69, No. Apr. 1, 2009, pp. 2919-2926.
Burton, Paul et al., "Tutorial in Biostatistics: Extending the Simple Linear Regression Model to Account for Correlated Responses: An Introduction to Generalized Estimating Equations and Multi-Leval Mixed Modelling", Statistics in Medicine, vol. 17, 1998, pp. 1261-1291.
Callery, MD, Mark P. et al., "Pretreatment Assessment of Resectable and Borderline Resectable Pancreatic Cancer: Expert Consensus Statement", Ann Surg Oncol, vol. 16, 2009, pp. 1727-1733.
Cao, Hung, "An Integrated uLED Optrode for Optogenetic Stimulation and Electrical Recording", IEEE Transactions on Biomedical Engineering, vol. 60, No. 1, Jan. 2013, pp. 225-229.
Chandra, Malavika et al., "Probing Pancreatic Disease Using Tissue Optical Spectroscopy", JBO Letters, Journal of Biomedical Optics, vol. 12(6), Nov./Dec. 2007, pp. 060501-1 to 060501-3.
Chandra, Malavika et al., "Quantitative Molecular Sensing in Biological Tissues: An Approach to Non-Invasive Optical Characterization", Optics Express, vol. 14, No. 13, Jun. 26, 2006, pp. 6157-6171.
Chandra, Malavika et al., "Spectral Areas and Ratios Classifier Algorithm for Pancreatic Tissue Classification Using Optical Spectroscopy", JBO Letters, Journal of Biomedical Optics, Jan./Feb. 2010, pp. 010514-1 to 010514-3.
Cree, "Cree EZ-n (Gent) LED Chips Handling and Packaging Recommendation", 2017, pp. 1-8.
Cubeddu, Rinaldo et al., "A Solid Tissue Phantom for Photon Migration Studies", Phys. Med. Biol., vol. 42, 1997, pp. 1971-1979.
Desjardins, Adrien E., "Needle Stylet with Integrated Optical Fibers for Spectroscopic Contrast During Peripheral Nerve Blocks", Journal of Biomedical Optics, vol. 16, No. 7, Jul. 2011, pp. 077001-1-077004-8.
Eloubeidi, Mohamed A. et al., "A Prospective Evaluation of an Algorithm Incorporating Routine Preoperative Endoscopic Ultrasound-Guided Fine Needle Aspiration in Suspected Pancreatic Cancer", J. Gastrointest. Surg., vol. 11, 2007, pp. 813-819.
Fang, Can et al., "Depth-Selective Fiber-Optic Probe for Characterization of Superficial Tissue at a Constant Physical Depth", Biomedical Optics Express, vol. 2, No. 4, Apr. 1, 2011, pp. 838-849.
Fritscher-Ravens, M.D., Annette et al., "Comparison of Endoscopic Ultrasound-Guided Fine Needle Aspiration for Focal Pancreatic Lesions in Patients with Normal Parenchyma and Chronic Pancreatitis", Journal of Gastroenterology, vol. 97, No. 11, 2002, pp. 2768-2775.
Frost & Sulli Van, "Analysis of the U.S. Breast Imaging Systems Market—A Guide to One of Medical Imaging's Key Multi-Modality Hubs", NB26-54, Jan. 2013, pp. 1-168.
Frost & Sullivan, "Analysis of the Global Tissue Diagnositcs Market—Reimbursement Cuts and Hospital Consolidation Impede the Uptake of Automated Equipment in Laboratories", NC76-52, Nov. 2013, pp. 1-219.

(56) References Cited

OTHER PUBLICATIONS

Frost & Sullivan, "Analysis of the U.S. Medical Ultrasound Imaging Systems Market-Growth to be Driven by Emerging Market Segments", N9CE-50, Dec. 2011, pp. 1-101.
Frost & Sullivan, "European Cancer Market Outlook—M62A-52", Jun. 2011, pp. i-9-88.
Frost & Sullivan, "U.S. Cancer Molecular Diagnostics Markets N39E-55", 2008, pp. i-6-16.
Fu, Henry L. et al., "A Low-Cost, Portable, and Quantitative Spectral Imaging System for Application to Biological Tissues", Optics Express, vol. 18, No. 12, Jun. 7, 2010, pp. 12630-12645.
Giovannini, Marc et al., "Feasibility of Intratumoral Confocal Microscopy Under Endoscopic Ultrasound Guidance", EUS Journal, Spring Publishing, vol. 1, Issue 2, 2012, pp. 80-83.
Gouillat, C., "Pancreatic Surgical Complications—the Case for Prophylaxis", Gut, vol. 49, 2001, pp. iv29-iv35.
Hanley, James A. et al., "Statistical Analysis of Correlated Data Using Generalized Estimating Equations: An Orientation", American Journal of Epidemiology, vol. 157, 2003, pp. 364-375.
Hartwig, W. et al., "Preoperative Tissue Diagnosis for Tumours of the Pancreas", British Journal of Surgery, vol. 96, 2009, pp. 5-20.
Hartwig, W. et al., "Preoperative Tissue Diagnosis for Tumours of the Pancreas", British Journal of Surgery, vol. 96, No. 5-20, pp. 1-20.
Ho, Choon-Kiat et al., "Complications of Pancreatic Surgery", HPB, vol. 7, 2005, pp. 99-108.
Hu, Wenyan et al., "Nonlinear Optical Microscopy for Histology of Fresh Normal and Cancerous Pancreatic Tissues", PLoS ONE, vol. 7, Issue 5, May 2012, pp. 1-8.
Iftimia, Nicusor et al., "Differentiation of Pancreatic Cysts with Optical Coherence Tomography (OCT) Imaging: an Ex Vivo Pilot Study", Biomedical Optics Express, vol. 2, No. 8, Aug. 1, 2011, pp. 2372-2382.
Isayama, Hiroyuki et al., "The Role of Endoscopic Ultrasound (EUS) in the Management of Patients with Pancreatic Cancer: Now Bigger Than Ever", J Gastrointest Oncol, 2013, Pates 121-122.
Kanick, PhD, Stephen C et al., "Characterization of Mediastinal Lymph Node Physiology In Vivo by Optical Spectroscopy During Endoscopic Ultrasound-Guided Fine Needle Aspiration", Journal of Thoracic Oncology, vol. 5, No. 7, Jul. 2010, pp. 981-987.
Kanick, S.C. et al., "Incorporation of Single Fiber Reflectance Spectroscopy Into Ultrsound-Guided Endoscopy (EUS-FNA) of Mediastinal Lymph Nodes", Biomed, 2010, 3 pages.
Kanick, Stephen Chad et al., "Integration of Single-Fiber Reflectance Spectroscopy Into Ultrasound-Guided Endoscopic Lung Cancer Staging of Mediastinal Lymph Nodes", Journal of Biomedical Optics, vol. 15, No. 1, Feb. 2010, pp. 017004-1-017004-8.
Konda, Vani J. et al., "An International Multi-Center Trial on Needle-Based Confocal Laser Endomicroscopy (nCLE): Results from the In Vivo CLE Study in the Pancreas with Endosonography of Cystic Tumors (INSPECT)", Gastroenteroley, AGA Abstracts, 2012, 1 page.
Konda, Vani J.A. et al., "First Assessment of Needle-Based Confocal Laser Endomicroscopy During EUs-FNA Procedures of the Pancreas (with Videos)", Gastrointestinal Endoscopy, vol. 74, No. 5, 2011, pp. 1049-1060.
Lee, Chin C. et al., "A New Gold-Indium Eutectic Bonding Method", Met. Res. Soc. Symp. Proc., vol. 264, 1992, pp. 305-310.
Lee, Chin C. et al., "Au—In Bonding Below the Eutectic Temperature", IEEE Transactions on Components, Hybrids, and Manufacturing Technology, vol. 16, No. 3, May 1993, pp. 311-316.
Lee, Seung Yup et al., "Characterizing Human Pancreatic Cancer Precursor Using Quantitative Tissue Optical Spectroscopy", Biomedical Optics Express, vol. 4, No. 12, 2013, pp. 2828-2834.
Liu, Yang et al., "Optical Markers in Duodenal Mucose Predict the Presence of Pancreatic Cancer", Clin Cancer Res, vol. 13, No. 15, Aug. 1, 2007, pp. 4392-4399.

Lo, Justin Y. et al., "A Strategy for Quantitative Spectral Imaging of Tissue Absorption and Scattering Using Light Emitting Diodes and Photodiodes", Optics Express, vol. 17, No. 3, Feb. 2, 2009, pp. 13272-1384.
Maesoon, Im et al., "Neural Probes Integrated with Optical Mixer/Splitter Waveguides and Multiple Stimulation Sites", MEMS, 2011, pp. 1051-1054.
Maiss, J. et al., "The compactEASIE is a Feasible Training Model for Endoscopic Novices: A Prospective Randomised Trial", Science Direct, 2006, pp. 70-78.
Orozco, Luis, "Programmable-Gain Transimpedance Amplifiers Maximize Dynamic Range in Spectroscopy Systems", Analog Dialogue 47-05, May 2013, Pates 1-5.
Pohl, H. et al., "Miniprobe Confocal Laser Microscopy for the Detection of Invisable Neoplasia in Patients with Barrett's Oesophagus", Gut, vol. 57, 2008, pp. 1648-1653.
Pu, Yang et al., "Screen Prostrate Cancer Using a Portable Near Infrared Scanning Imaging Unit with an Optical Fiber-Based Rectal Probe", Optical Biosy X, Proc. of SPIE, vol. 8220, 2012, pp. 822002-1-822002-8.
Schwarz, Richard A. et al., "Ball Lens Coupled Fiber-Optic Probe for Depth-Resolved Spectroscopy of Epithelial Tissue", Optics Letters, vol. 30, No. 10, pp. 1159-1161.
Sharma, Vikrant et al., "Auto-Fluorescence Lifetime Spectroscopy for Prostate Cancer Detection: An Optical Biopsy Approach", Biomedical Optics and 3D Imaging OSA, 2012, 3 pages.
Smith, Benjamin et al., "Future of Cancer Incidence in the United States: Burdens Upon an Aging, Changing Nation", J Clin Oncol, vol. 27, 2009, pp. 2758-2765.
Soares, Jaqueline S. et al., "Diagnostic Power of Diffuse Reflectance Spectroscopy for Targeted Detection of Breast Lesions with Microcalcifications", PNAS, vol. 110, No. 2, Jan. 8, 2013, pp. 471-476.
Song, MD, Tae Jun et al., "The Prospective Randomized, Controlled Trial of Endocscopic Ultrasound-Guided Fine-Needle Aspiration Using 22G and 19G Aspiration Needles for Solid Pancreatic or Peripancreatic Masses", The American Journal of Gastroenterology, 2010, pp. 1739-1745.
Testoni, Pier A. et al., "Intraductal Optical Coherence Tomography for Investigating Main Pancreatic Duct Strictures", American Journal of Gastroenterolgy, 2007, pp. 269-274.
Turzhitsky, Vladimir et al., "Investigating Population Risk Factors of Pancreatic Cancer by Evaluation of Optical Markers in the Duodenal Mucosa", Disease Markers, vol. 25, 2008, pp. 313-321.
Vishwanath, Karthik et al., "Do Fluorescence Decays Remitted from Tissues Accurately Reflect Intrinsic Fluroophore Lifetimes?", Optics Letters, vol. 29, No. 13, Jul. 1, 2004, pp. 1512-1514.
Vishwanath, Karthik et al., "Quantitative Fluorescence Lifetime Spectroscopy in Turbid Media: Comparison of Theoretical, Experimental and Computational Method", Physics in Medicine and Biology, vol. 47, 2002, pp. 3387-3405.
Viswanath, Karthik et al., "Portable, Fiber-Based, Diffuse Reflection Spectroscopy (DRS) Systems for Estimating Tissue Optical Properties", Applied Spectroscopy, vol. 65, No. 2, 2011, pp. 206-215.
Volynskaya, Zoya et al., "Diagnosing Breast Cancer Using Diffuse Reflectance Spectroscopy and Intrinsic Fluorescence Spectroscopy", Journal of Biomedical Optics, vol. 13, No. 2, Mar./Apr. 2008, pp. 024012-1-024012-9.
Wentz, Christian T. et al., "A Wirelessly Powered and Controlled Device for Optical Neural Control of Freely-Behaving Animals" J Neural Eng, vol. 8, No. 4, Aug. 2011, pp. 1-14.
Wilson, R.H. et al., "Models of Light Propagation in Human Tissue Applied to Cancer Diagnostics", Technology in Cancer Research and Treatment, vol. 10, No. 2, Apr. 2011, pp. 121-134.
Wilson, Robert H. et al., "Optical Spectroscopy Detects Histological Hallmarks of Pancreatic Cancer", Optics Express, vol. 17, No. 20, Sep. 28, 2009, pp. 17502-17516.
Wilson, Robert H. et al., "Photon-Tissue Interaction Model Enables Quantitative Optical Analysis of Human Pancreatic Tissues", Optics Express, vol. 18, No. 21, Oct. 11 2010, pp. 21612-21621.

(56) References Cited

OTHER PUBLICATIONS

Wilson, Robert H., "Optical Spectroscopy Detects Histological Hallmarks of Pancreatic Cancer", Optics Express, vol. 17, No. 20, Sep. 28, 2009, pp. 17502-17516.
Zhu, Changfang et al., "Fluroescence Spectroscopy: An Adjunct Diagnostic Tool to Image-Guided Core Needle Biopsy of the Breast", IEEE Transactions on Biomedical Engineering, vol. 56, No. 10, Oct. 2009, pp. 2518-2528.
Zinter, Joseph P. et al., "Maximizing Fluoroscence Collection Efficiency in Mutliphoton Microscopy", Optics Express, vol. 19, No. 16, Aug. 1, 2011, pp. 15348-15362.

\* cited by examiner

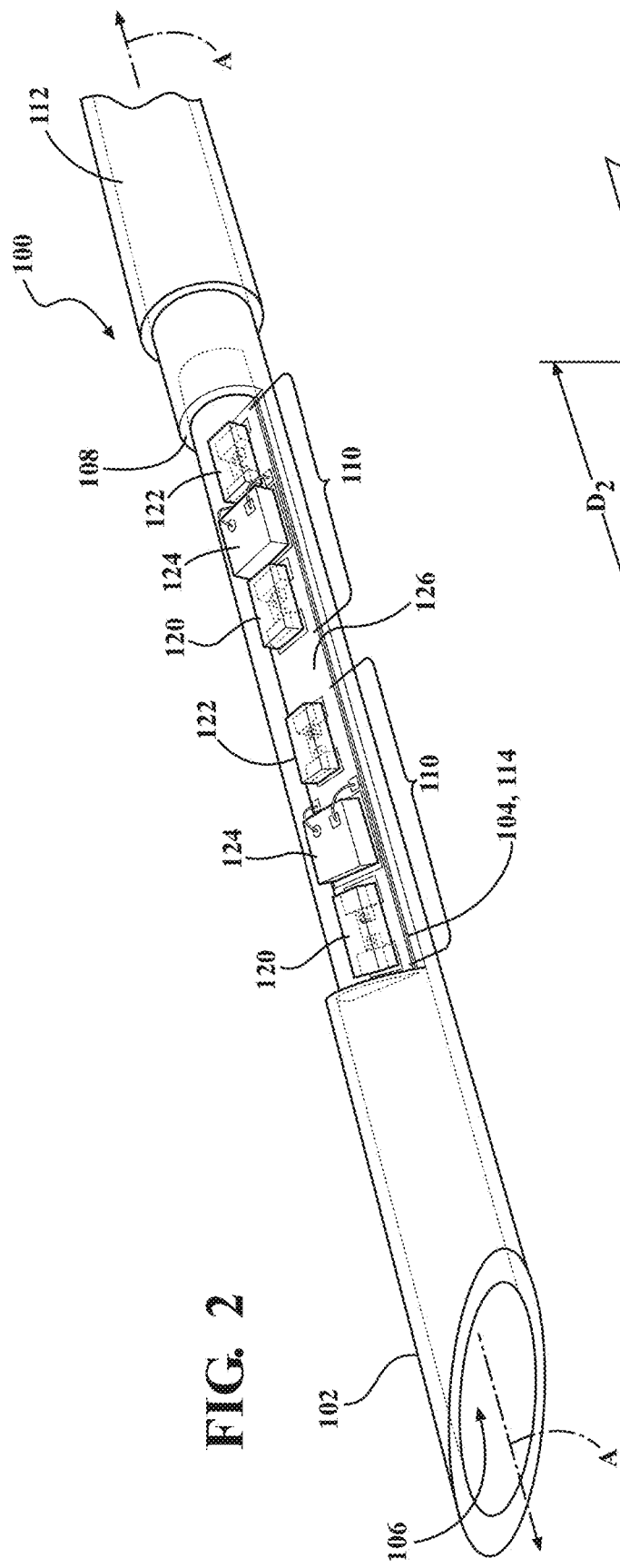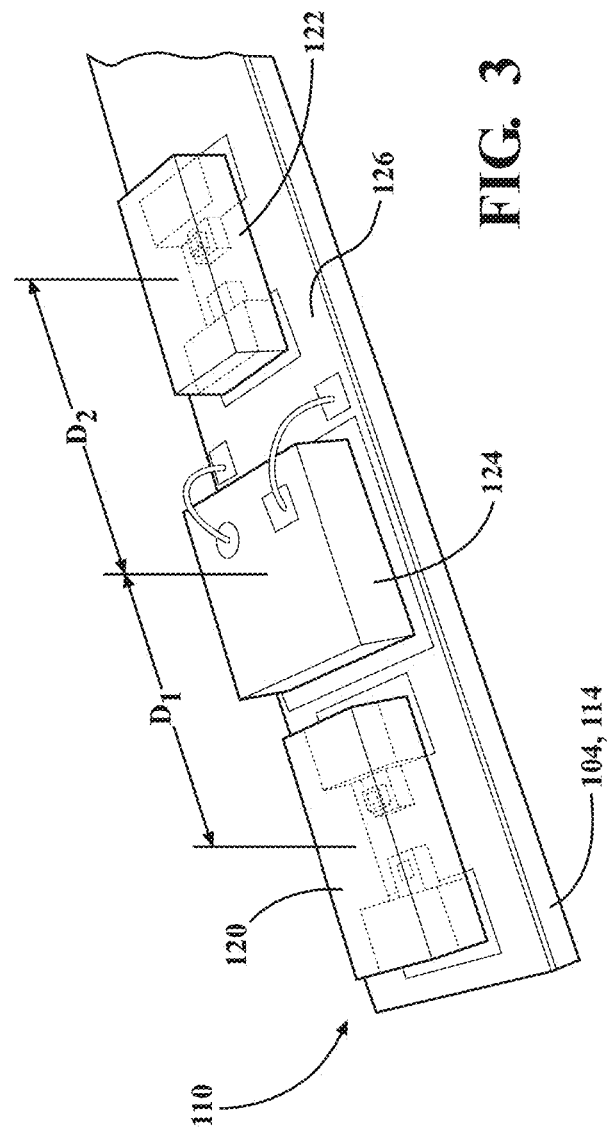

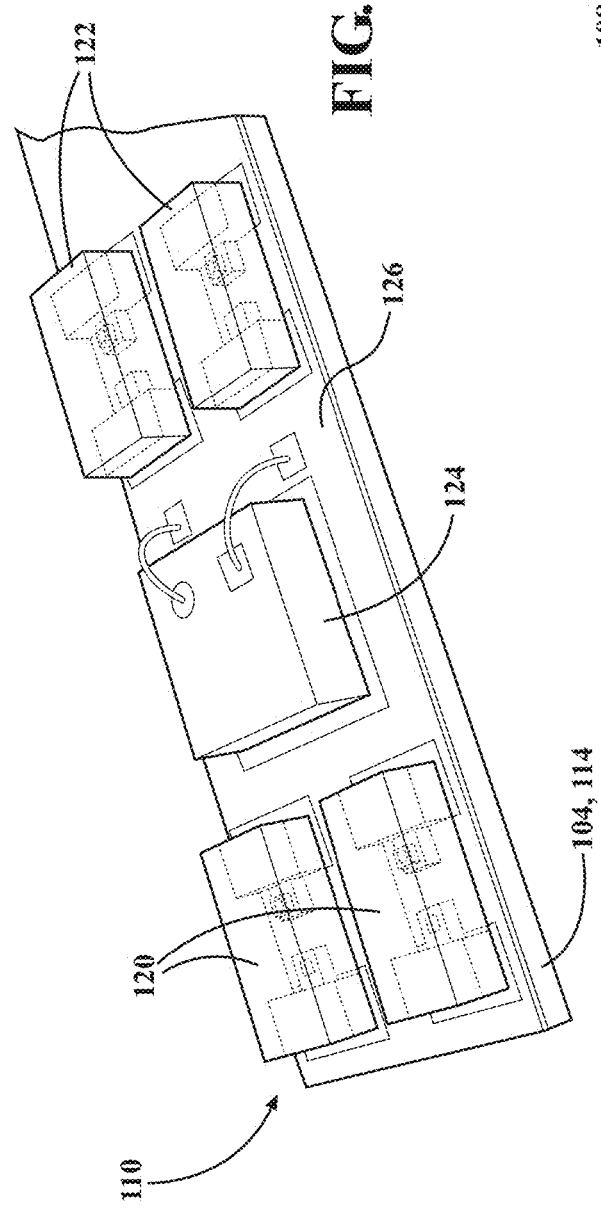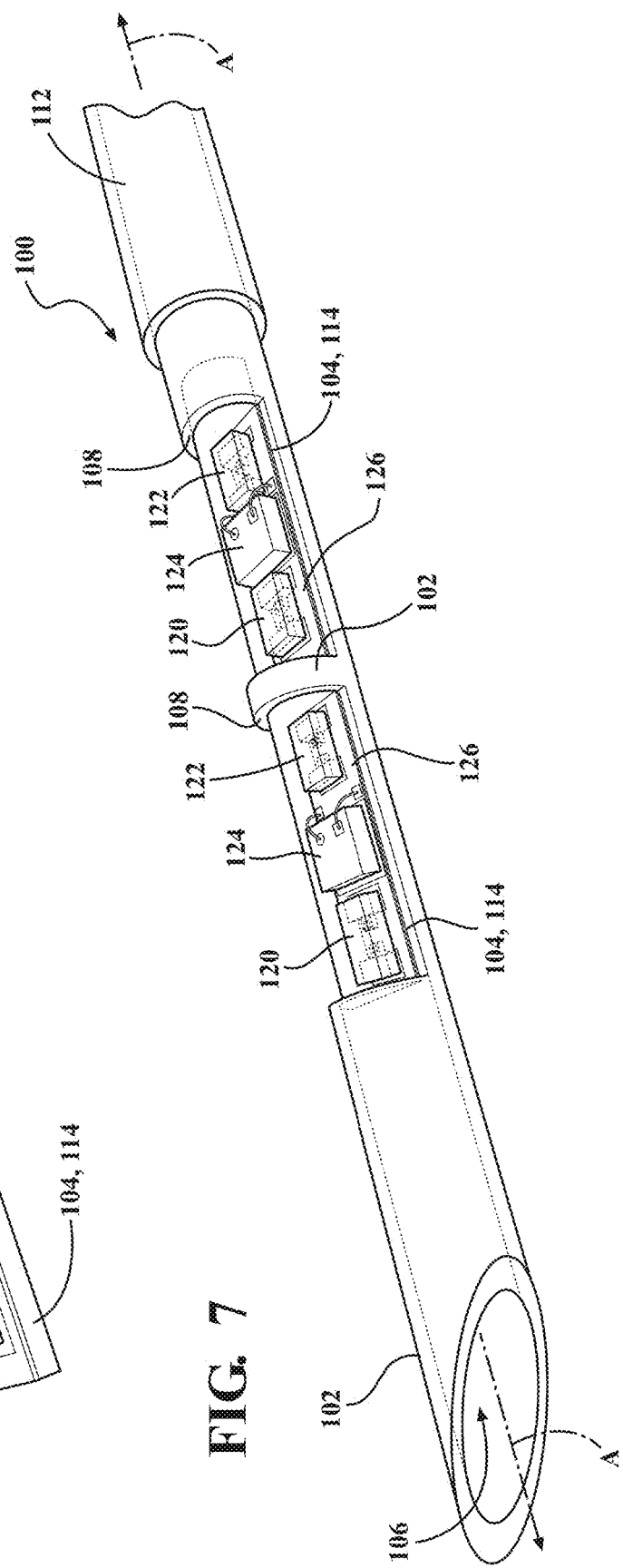

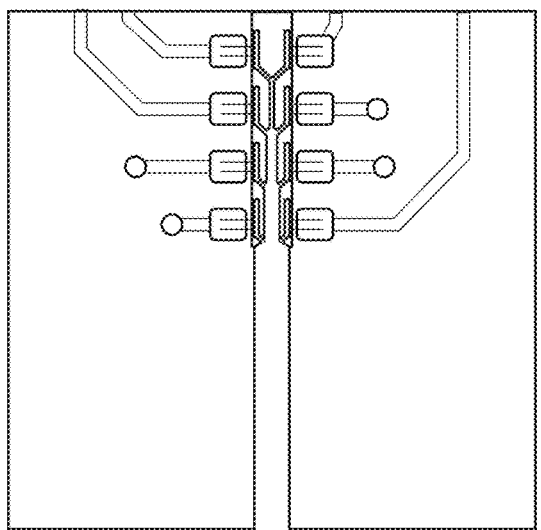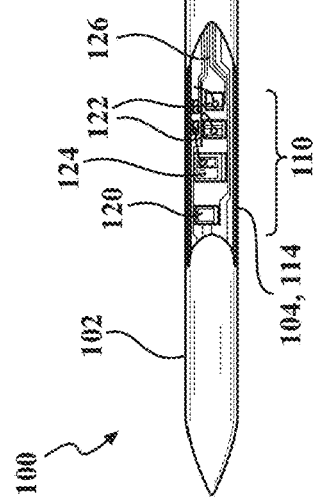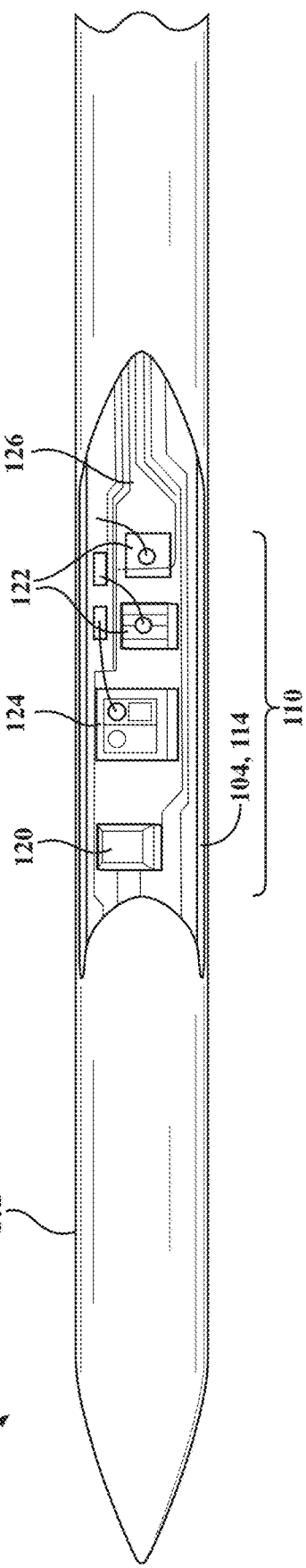

Packaged μLED
(Rohm PicoLED)

| Component | Specification |
|---|---|
| Dimensions | 0.300x0.600x0.200 mm |
| Brightness | 17 mcd @ 470 nm, 60 mcd @ 630 nm |
| Forward Voltage | 2.9V @ 470 nm, 2V @ 630 nm |
| Forward Current | 5mA @ 470 nm, 20mA @ 630 nm |

Phototransistor
(Vishay TI090P)

| Component | Specification |
|---|---|
| Dimensions | 0.530x0.530x0.185 mm |
| Current Input | 50 mA |
| Collector (Current) Output | 0.43-0.77 mA @ 905 nm, E=1mW/cm$^2$ |
| Sensitivity | -0.1@470 nm, -0.5@630 nm (Relative to maximum sensitivity) | a) Rinse with acetone and IPA
b) Eutectic bonding of PD and Red LED
c) Eutectic bonding of Blue LED
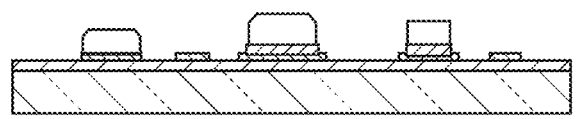
d) Wire bonding on PD and Red LED
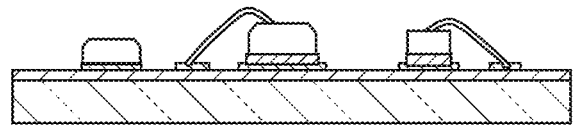
e) Epoxy Encapsulation
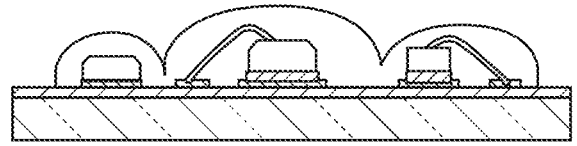
FIG. 14
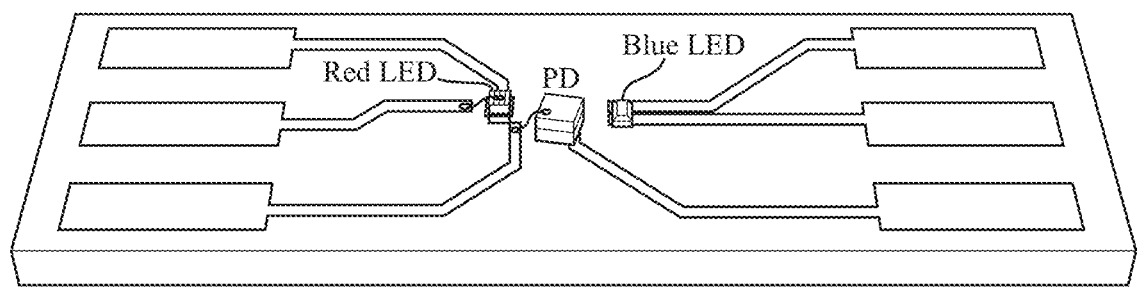
FIG. 15

Table 1. Comparison of extracted parameters by PTI model using 176 wavelengths and 4 wavelengths.

| | Tissue Type (Number of measurements) | 176 wavelengths | 4 wavelengths |
|---|---|---|---|
| Nuclear Size (μm ± Std. Error) | Normal (39) | 8.96 ± 0.10 | 8.78 ± 0.10 |
| | Chronic Pancreatitis (34) | 9.20 ± 0.22 | 9.14 ± 0.16 |
| | Adenocarcinoma (32) | 10.70 ± 0.30 | 10.06 ± 0.25 |
| Nuclear Refractive Index (± Std. Error) | Normal (39) | 1.372 ± 0.001 | 1.373 ± 0.001 |
| | Chronic Pancreatitis (34) | 1.375 ± 0.002 | 1.374 ± 0.001 |
| | Adenocarcinoma (32) | 1.391 ± 0.002 | 1.383 ± 0.001 |

FIG. 20

SYSTEM FOR ANALYZING TISSUE

CROSS REFERENCE TO RELATED APPLICATIONS

The subject patent application is a Continuation-In-Part of International Application No. PCT/US2016/023437 filed on Mar. 21, 2016, which claims priority to and all the advantages of U.S. Provisional Application No. 62/177,603, filed on Mar. 19, 2015. The contents of International Application No. PCT/US2016/023437 and U.S. Provisional Application No. 62/177,603 are incorporated herein by reference in their entirety.

GOVERNMENT LICENSE RIGHTS

This invention is made with government support under EB018537 awarded by the National Institutes of Health. The government has certain rights in the invention.

FIELD OF THE DISCLOSURE

The present disclosure relates generally to tissue diagnostic tools, and more particularly, to a system for analyzing tissue.

BACKGROUND

Considerable advancements in optical diagnostics have been made in recent years for non-invasive, quantitative, and rapid analysis of tissue in a clinical setting. Numerous advancements have also been made in cell biology through the development of fluorescence-based analysis methods. Furthermore, biomedical studies (including studies involving cancer and other diseases) have been transformed through commercial technology for whole body animal imaging, such as, e.g. the Caliper Life Sciences IVIS imaging system. In clinical settings, the US Food and Drug Administration (FDA)-approved optical technologies are typically employed, such as a pulse oximeter, a Philips BiliChek bilirubinometer, a DentalEZ Identafi oral cancer screening system, and a MELA Sciences MelaFind system for each melanoma detection.

For many clinical applications, optical technologies are not subject to a confined space, as the tissue being studied is readily accessible from outside of the body, such as in the oral cavity or the skin. Therefore, presently-developed technologies are typically large footprint instruments, such as robust and expansive spectroscopy/imaging systems that access tissue with remote fiber-optic probes. Remote fiber-optic probes are often employed in these techniques, because the probes are easy to use, are typically reliable, and enable remote sample sensing (i.e., sample sensing away from the equipment).

Needle-based clinical methodologies have also been used for tissue diagnostics, such as fine-needle aspiration for cancer detection (including breast, lung, prostate, and pancreatic cancer detection), as well as for pain management (including nerve block treatments). Two common approaches for needle-based tissue analysis include imaging and spectroscopy. Imaging through a hollow needle has also been used with the needle-based confocal imaging system, such as the Cellvizio available from Mauna Kea. However, there are limitations to needle-based imaging systems, such as a small field-of-view and the system is often complicated and time consuming for real-time quantitative image analysis. Spectroscopy may be employed for remote tissue sensing through hollow needles. However, spectroscopy systems utilizing fiber-optic probes are typically limited, e.g., in terms of their rigidity, lack of volumetric mapping, and/or constrained center-to-center spacing between the optic source and detector(s). Furthermore, given the small inner diameter of the hollow needles, current needle-based optical sensing techniques often employ fiber-optic probes for light delivery and detection. Critical limitations to such approaches include the relative rigidity of the fiber-optic probes, such as the inability to undergo tight bends, and the inability of the fiber-optic probes to enable volumetric mapping.

Pancreatic adenocarcinoma (i.e., pancreatic cancer) is one of the leading causes of cancer death in the United States. Among the estimated 42,000 patients diagnosed with pancreatic cancer in the United States in 2014, about 7% of these patients were diagnosed at an early stage. Pancreatic cancer also has the highest mortality rate of any solid tumor, with a five-year survival rate of just 5%. Among the estimated 42,000 patients diagnosed with pancreatic cancer in the United States in 2014, those with advanced stage metastatic disease have a five-year survival rate of about 1.8%, while those with advanced stage localized regional disease (i.e., where the tumor is not amenable to surgical removal, typically due to involvement of critical blood vessels) have a five-year survival rate of about 8%. Further, the five-year survival rate of patients with surgically resectable (or potentially resectable after neo-adjuvant therapy) disease is about 20%.

Current diagnostic methods, including computed tomography (CT), magnetic resonance imaging (MRI) and endoscopic ultrasound (EUS), have not yet provided accurate diagnosis during the early stage of pancreatic cancer, such as by failing to identify small lesions or accurately differentiating masses as either adenocarcinoma or pancreatitis (inflammation of the pancreas). Further, identifying and utilizing molecular markers has not been helpful with solving the foregoing problem(s).

A key challenge for pancreatic cancer detection is to provide an accurate tissue diagnosis that allows for rapid institution of therapy, such as surgery for resectable tumors, neoadjuvant for borderline resectable disease, or definitive chemoradiotherapy with localized unresectable disease. Pretreatment tissue diagnosis is typically mandatory for patients considered for therapy, and the currently preferred modality for obtaining a tissue diagnosis is endoscopic ultrasound-guided fine-needle aspiration (EUS-FNA). However, EUS-FNA has limitations. For example, challenges of obtaining accurate characterization of suspect pancreatic neoplasia may occur due to the relative inaccessibility of the pancreas given its anatomical location, the non-specific nature of symptoms, and/or the characteristic stromal reaction with intense fibrosis associated with adenocarcinoma and chronic pancreatitis. These factors significantly complicate attempts to differentiate the similar appearing lesions by imaging, even with cytological evaluation of fine-needle aspirates. Finding small nests of tumor cells in an area of fibrosis is one challenge, and differentiating well-differentiated cancers from normal is another challenge.

Endoscopic ultrasound (EUS) is an imaging modality that provides access to the pancreas for tissue evaluation, and is a current diagnostic procedure for tissue acquisition in suspect pancreatic cancer. FIG. 1 is a clinical image from a pancreatic EUS-FNA. The image shown in FIG. 1 lacks specific contrast afforded by ultrasound sensing alone, and the pancreatic mass is difficult to distinguish. Further, classification of the mass often relies on cytology, which is typically non-diagnostic. While EUS imaging remains the most sensitive test to identify a pancreatic mass, determining that the mass is benign or malignant remains problematic due to reliance on EUS-guided fine needle aspiration sampling. As mentioned above, however, FNA cytology samples are typically non-diagnostic leading to a negative predictive value of 50 to 70%, given the high pre-test likelihood for cancer among the patients referred for the procedure. For such patients with a strong clinical suspicion of pancreatic cancer, laparotomy to obtain tissue for those with unresectable disease or an unnecessary resection for those with a resectable tumor may be performed.

The failure of accurate tissue characterization often causes patients to undergo major surgery to reveal only a benign or inflammatory disease on pathologic examination. The mortality of pancreatic surgery is from 2 to 5% in experienced centers, with major morbidity of 20 to 25%. In addition, when chronic pancreatitis is found to be present, EUS-FNA detected pancreatic adenocarcinoma with a sensitivity of just 54% and many studies have concluded that EUS-FNA is insufficient to rule out a malignancy.

Additionally, studies have shown that endoscopic ultrasound compatible optoelectronic sensing technology provides diagnostic information to supplement cytology-based diagnosis and overcomes the limitations of cytology-based diagnosis. This may be accomplished by providing independent diagnosis of a pancreatic abnormality or by guiding an endoscopist performing the EUS to select the most likely areas to obtain diagnostically relevant cytological material. Studies have also shown that optical sensing can provide a new source of contrast for the detection of pancreatic cancer.

Due, at least in part, to the challenges associated with accessing the pancreas, relatively little research in biomedical optics has been conducted in the human pancreas. Field effect analysis of duodenal tissues adjacent the pancreas and limited optical coherence tomography studies in the pancreas also do not address the targeted clinical problem. Further, recent studies have established feasibility for needle-based confocal laser endomicroscopy, as diagnostic utility has been considered elusive even in large clinical studies.

For at least the reasons set forth above, there is an opportunity to develop an improved tool and technique for tissue diagnostics, particularly for diagnosing pancreatic cancer.

SUMMARY

One embodiment of the present disclosure includes a system for analyzing tissue. The system includes a platform and an optical sensing unit coupled to the platform. The optical sensing unit has a detector and a plurality of light sources surrounding and electrically isolated from the detector. The optical sensing units obtain optical data for tissue analysis.

Another embodiment of the present disclosure includes a system for analyzing tissue comprising a tissue aspiration needle defining a cavity having an opening and a microprobe disposed within the cavity and carried by the tissue aspiration needle. The microprobe defines a longitudinal axis and has a platform and a plurality of optical sensing units coupled to the platform and linearly arranged along the longitudinal axis. The optical sensing units are exposed through the opening of the cavity. Each of the sensing units has first and second light sources and a detector arranged between and electrically isolated from the first and second light sources. The plurality of sensing units obtains optical data substantially simultaneously for analyzing the tissue.

Another embodiment of the present disclosure includes a method of analyzing tissue utilizing a system comprising a platform and an optical sensing unit coupled to the platform. The optical sensing unit has a detector and a plurality of light sources surrounding and electrically isolated from the detector. The method comprises the steps of directing a light from the light sources toward the tissue, obtaining optical data while the light is being directed toward the tissue, and utilizing the optical data to analyze the tissue.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Advantages of the present disclosure will be readily appreciated as the same becomes better understood by reference to the following detailed description when considered in connection with the accompanying drawings. It is to be understood that the drawings are purely illustrative and the drawings are not necessarily drawn to scale.

FIG. 2 is a semi-schematic, perspective view of an embodiment of a system for analyzing tissue including a microprobe carried by a tissue aspiration needle.

FIG. 3 is an enlarged, semi-schematic, perspective view of an embodiment of a sensing unit of the microprobe.

FIG. 4 is a semi-schematic, perspective view of another embodiment of a sensing unit of the microprobe.

FIG. 5A is a semi-schematic, plan view of another embodiment of a system for analyzing tissue including a microprobe carried by a tissue aspiration needle.

FIG. 5B is an enlarged view of a portion of the system of FIG. 5A, illustrating another embodiment of a sensing unit of the microprobe.

FIG. 7 is a semi-schematic perspective view of another embodiment of the system for analyzing tissue, where the aspiration needle has a plurality of openings.

FIG. 14 illustrates an example of a process for assembling the first prototype board of the optoelectronic microprobe.

FIG. 15 illustrates an assembled prototype board for the optoelectronic microprobe.

FIG. 20 is a table (Table 1) comparing extracted parameters of different types of pancreatic tissues by the PTI model using 176 wavelengths and 4 wavelengths.

DETAILED DESCRIPTION

Referring to the figures, wherein like numerals indicate corresponding parts throughout the several views, embodiments of a system 100, 200 for analyzing tissue are shown in the figures and described in detail below.

In one embodiment shown, for example, in FIGS. 2-5B and 7-9, the system 100 includes a tissue aspiration needle 102 and a microprobe 104 carried by the needle 102. The microprobe 104 utilizes EUS-compatible optoelectronic sensing technology for obtaining diagnostic information of tissue, such as pancreatic tissue. For instance, the microprobe 104 utilizes the optoelectronic sensing technology to obtain optical spectroscopy data of fresh pancreatic tissue. Typically, the optical spectroscopy data is obtained utilizing the microprobe 104 during a pancreatic EUS-FNA procedure. The optical spectroscopy data may be used in a corresponding pancreatic tissue classification algorithm to differentiate between malignant and non-malignant pancreatic tissues. Utilizing the EUS-compatible optoelectronic sensing technology, the optical data obtained by the system 100 can also be used to provide additional diagnostic information to supplement cytology-based diagnosis. In some instances, the EUS-compatible optoelectronic sensing technology can be used to overcome certain limitations of cytology-based diagnosis, such as by providing independent diagnosis of the pancreatic abnormality or by guiding the endoscopist performing the procedure to select the most likely areas to obtain diagnostically relevant cytological material.

Figure 1:
FIG. 1 is a clinical image generated from a pancreatic endoscopic ultrasound-guided fine-needle aspiration technique showing a pancreatic mass.
Figure 6A:
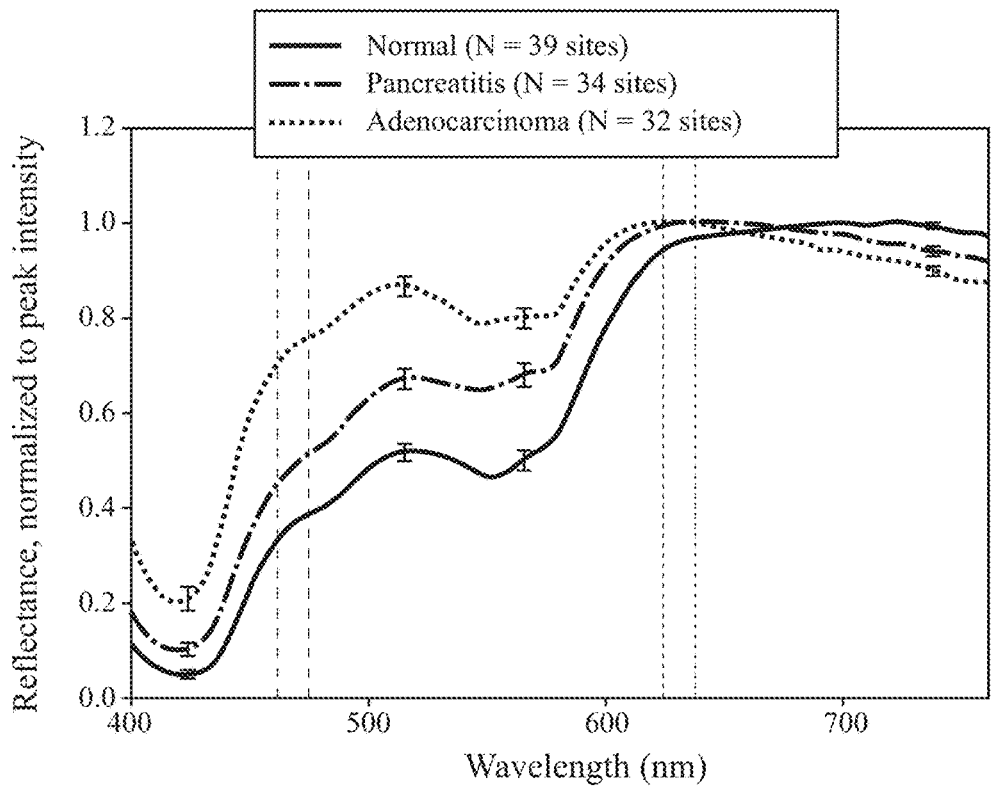
FIG. 6A is a graph showing the average reflectance spectra illustrating differences between normal tissues, tissues with chronic pancreatitis, and tissues with pancreatic adenocarcinoma.
Figure 6B:
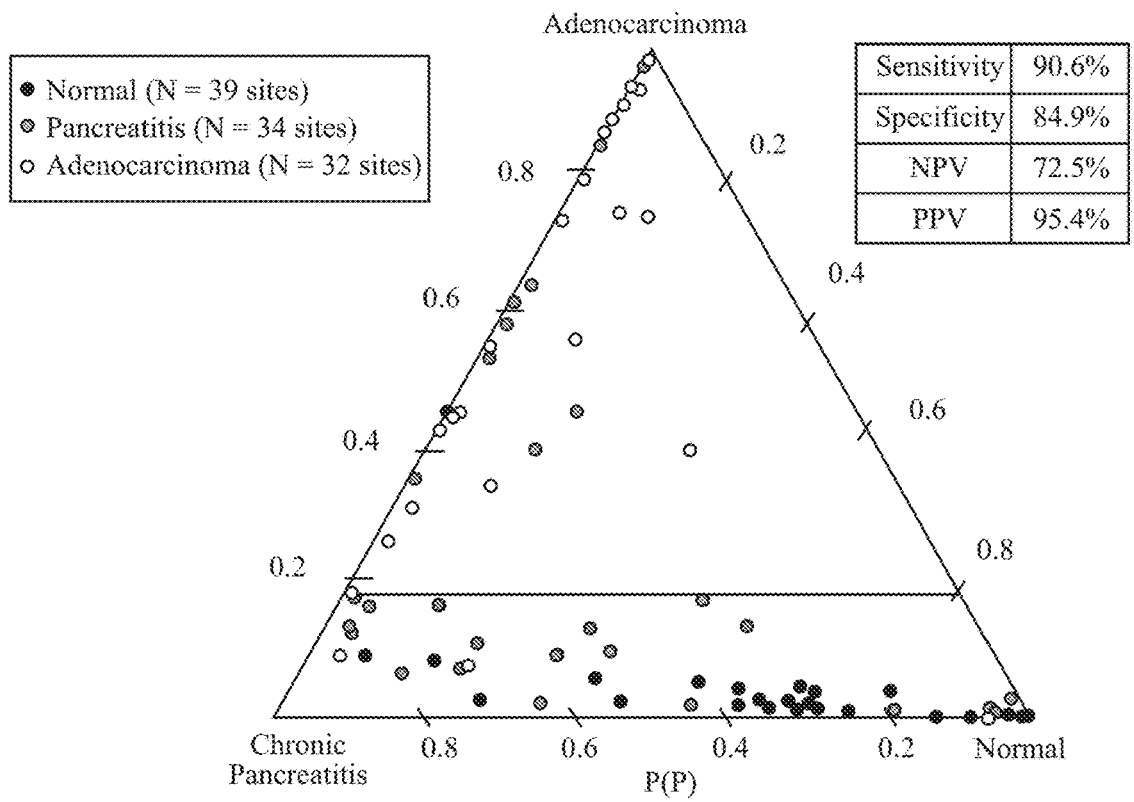
FIG. 6B is a graph showing previously reported analysis metrics utilizing mathematical algorithms for intrapatient correlation classified cancerous from benign pancreatic tissues with a sensitivity of about 90.6% and specificity of about 84.9%.
Figure 6C:
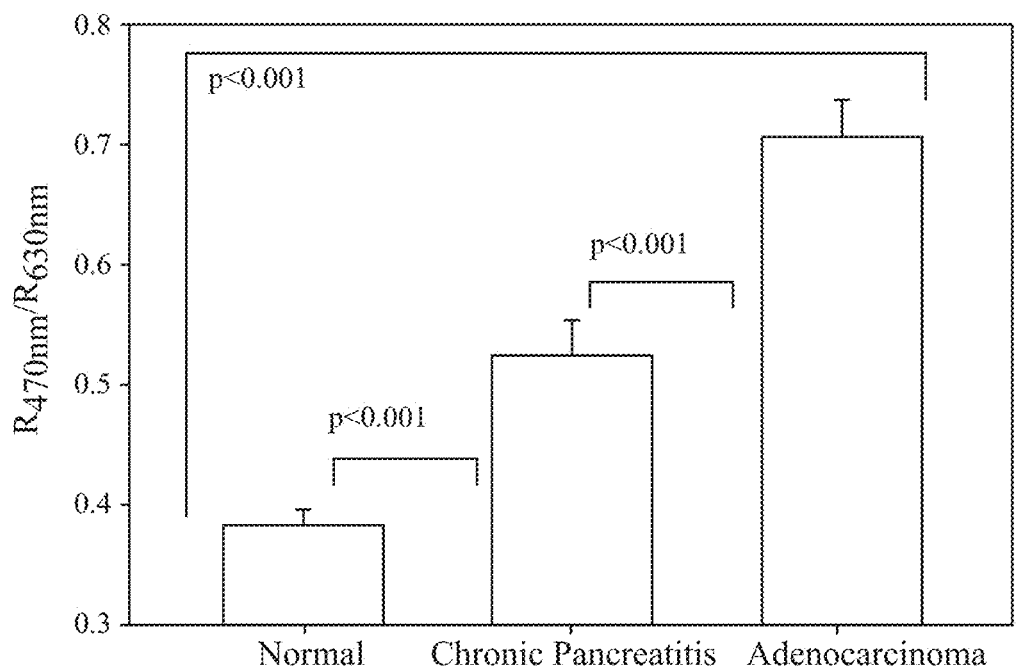
FIG. 6C is a graph showing the ratio of summed intensities within each wavelength band distinguished among normal tissues, tissues with chronic pancreatitis, and tissues with pancreatic adenocarcinoma.
Figure 6D:
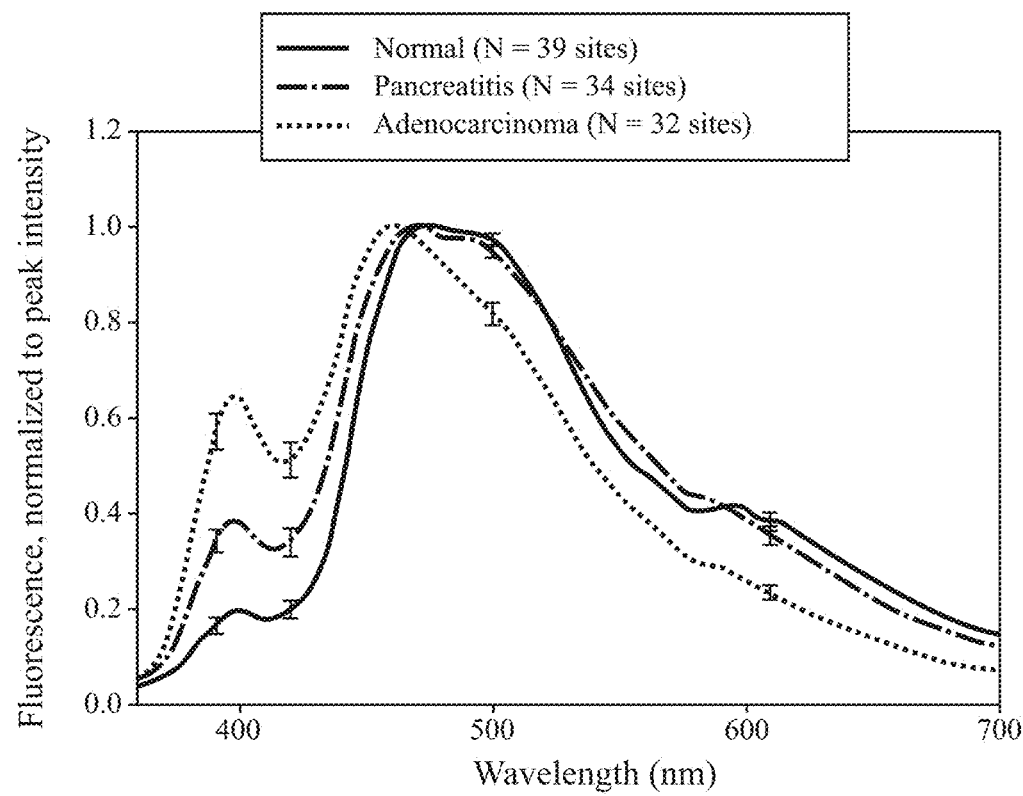
FIG. 6D is a graph showing the averaged fluorescence spectra for normal tissues, tissues with chronic pancreatitis, and tissues with pancreatic adenocarcinoma.
Figure 6E:
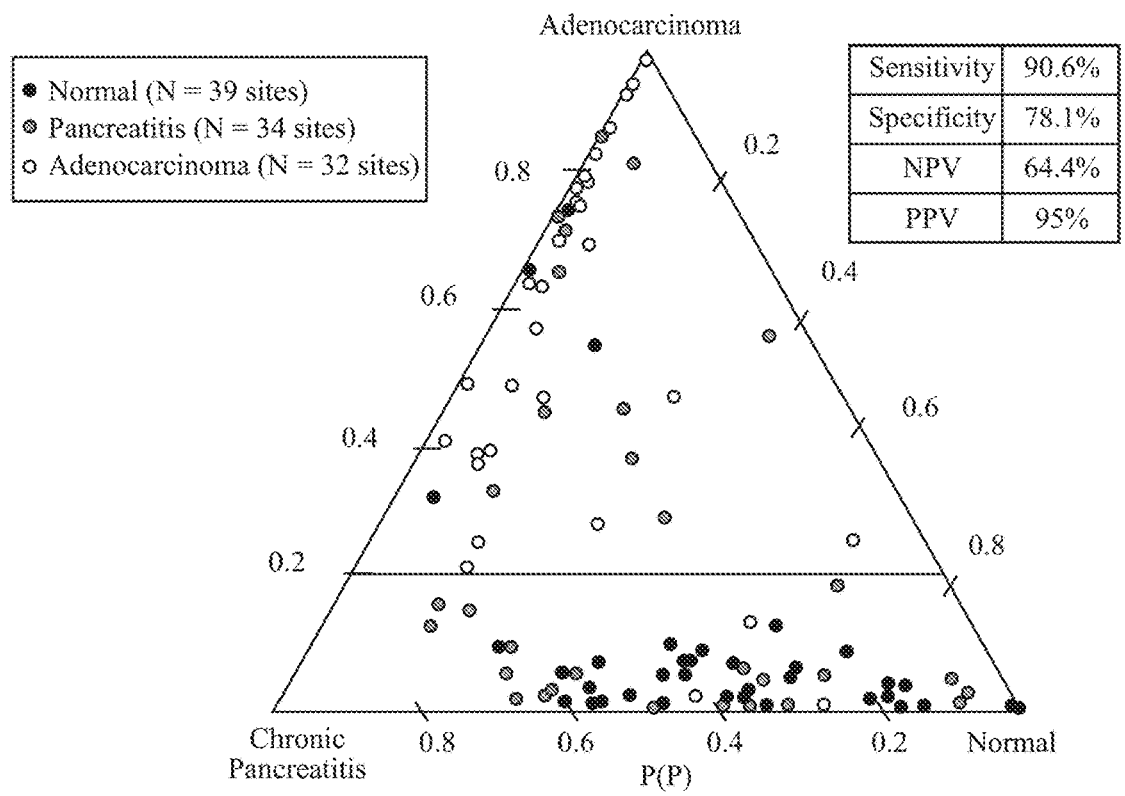
FIG. 6E is a graph showing analysis metrics utilizing steady state fluorescence for intrapatient correlation classified cancerous from benign pancreatic tissues with a sensitivity of about 90.6% and specificity of about 78.1%.
Figure 6F:
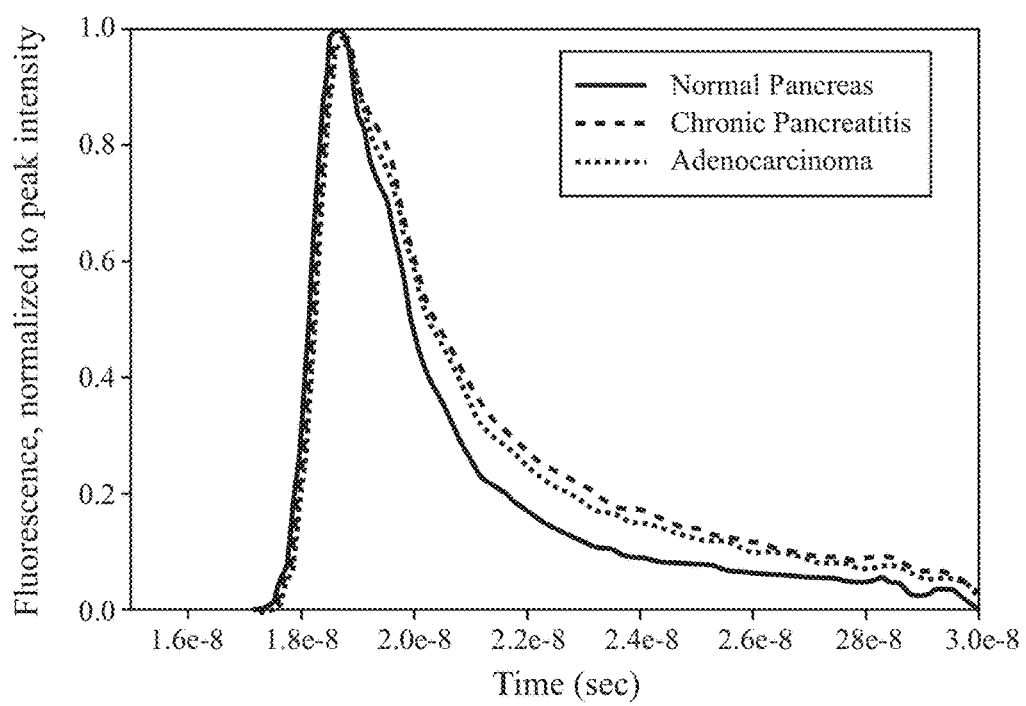
FIG. 6F is a graph showing the time-resolved fluorescence for normal tissues, tissues with chronic pancreatitis, and tissues with pancreatic adenocarcinoma.

Furthermore, the microprobe 104 is robust, compact, and enables volumetric mapping of the tissue. Accordingly, the microprobe 104 can be used to interrogate a larger volume of tissue compared to current fine-needle aspiration procedures, which can measure just a single tissue site. The microprobe 104 of the system 100, again which utilizes optoelectronic sensing technology, can also advantageously provide volumetric mapping of multiple tissue sites and enhance accuracy of the diagnosis. For example, FIGS. 6A through 6F illustrate results from a clinical pilot study from freshly-excised pancreatic tissue from eighteen patients. FIG. 6A shows that the averaged reflectance spectra revealed significant differences between normal, chromic pancreatitis, and pancreatic adenocarcinoma. FIG. 6B shows that the classification algorithm accounting for intrapatient correlation distinguished cancerous from benign pancreatic tissues with a sensitivity of 90.6% and a specificity of 84.9%. FIG. 6C shows the ratio of summed intensities within each wavelength band accurately distinguished among the three most prevalent pancreatic tissues. FIG. 6D shows an averaged fluorescence spectrum, which also reveals significant differences between normal, chronic pancreatitis, and pancreatic adenocarcinoma. FIG. 6E shows analysis metrics using steady-state fluorescence also classified cancerous from benign pancreatic adenocarcinoma. FIG. 6F shows that time-resolved fluorescence reveals significant differences between normal chronic pancreatitis and pancreatic adenocarcinoma. Adding parameters related fluorescence lifetime classification algorithm classified adenocarcinoma from benign tissues with sensitivity of 92.3% and specificity of 82.9%, which shows that time-resolved fluorescence sensing has the potential to accurately distinguish pancreatic cancer from benign tissues.

In addition to the above, the microprobe 104 can be used to accurately diagnose three common types of pancreatic tissues—normal tissue, chronic pancreatitis, and adenocarcinoma. Further, the system 100 is significantly smaller than other optical-fiber-based systems, and the system 100 can have comparable or even superior optical performance than other optical-fiber-based systems. The system 100 is also usable for non-invasive diagnostics (e.g., the microprobe can be used to view the tissue, rather than take the tissue) and is suitable and/or compatible with EUS-FNA procedures. These features render the system 100 as being compatible with current clinical standard-of-care procedures in pancreatic cancer staging, as well as in other current clinical standard-of-care procedures of lung, prostate, and breast cancer staging.

The System 100

Embodiments of the system 100 are described below with reference to FIGS. 2-5B and 7-9. As shown, the system 100 includes a platform 114 and an optical sensing unit 110 coupled to the platform 114. In this embodiment, the platform 114 may be coupled to or be part of a stylet. As shown, the platform 114 is a groove defined within the stylet. The combination of the platform 114 (and stylet) and optical sensing unit 100 in this embodiment is referred to as a microprobe 104. In an example, the microprobe 104 has a length and defines a longitudinal axis A.

As mentioned above, the system 100 for analyzing tissue comprises a tissue aspiration needle 102 and a microprobe 104 carried by the tissue aspiration needle 102. In an embodiment, the tissue aspiration needle 102 may be a hollow needle. For example, the tissue aspiration needle 102 defines a cavity 106 having an opening 108. As shown, the microprobe 104 may be inserted within the cavity 106 of the hollow tissue aspiration needle 102. As a non-limiting example, the needle 102 may be a EUS-FNA aspiration needle. Non-limiting examples of suitable aspiration needles include 19 gauge (19 G) hollow needles, 22 gauge (22 G) hollow needles, and 25 gauge (25 G) hollow needles. A non-limiting example of suitable a needle is a hollow needle with an inner diameter of from 0.50 to 1.00 mm. In another non-limiting example, the needle 102 is a 19 gauge hollow needle with an inner diameter of from 0.65 to 0.85 mm. In one particular non-limiting example, the needle 102 is a 19 gauge hollow needle having a 0.68 mm (i.e., 680 μm) inner diameter. In yet another particular non-limiting example, the needle 102 is a 19 gauge hollow needle having a 0.85 mm (i.e., 850 μm) inner diameter. Another non-limiting example of a suitable needle is a 22 gauge hollow needle having a 0.45 to 0.65 mm inner diameter. It is to be understood that any EUS-FNA suitable hollow aspiration needle may be used having any suitable gauge and/or inner diameter. In addition, the hollow aspiration needle may have any suitable length. In an example, the needle 102 is about 5 to 8 cm in length. One non-limiting example of a EUS-FNA suitable hollow aspiration needle is a Cook Medical EchoTip® ProCore™ biopsy needle, available from Cook Medical Inc. (Bloomington, Ind.).

As mentioned above, the aspiration needle 102 also includes an opening or window 108. The opening 108 is formed in the body of the needle 102 and extends partially along the length of the needle 102. The opening 108 typically aligns with the optical sensing unit(s) 110 disposed on the microprobe 104 to enable quasi-spectral sensing. In an embodiment shown in FIG. 2, the needle 102 includes a single opening 108 aligned with the optical sensing unit(s) 110 of the microprobe 104. In instances where the microprobe has a plurality of optical sensing units 110, the needle 102 may have multiple openings 108, with each opening 108 being aligned with a respective one of the optical sensing units 110. This is shown, for example, in FIG. 7.

The opening(s) 108 may have any suitable length and width. In instances where the needle 102 has a single opening 108, the opening 108 is typically large enough to expose the entire optical sensing unit 110 (such as where the microprobe 104 has a single optical sensing unit 110). For instance, for an optical sensing unit 110 having a length of about 2 mm, the opening 108 may have a length of at least 2 mm. Alternatively, when the needle 102 may have a single opening 108, the opening 108 may be large enough to expose all of the optical sensing units 110 (such as where the microprobe 104 has multiple optical sensing units 110). In instances where the needle 102 has multiple openings 108, each opening 108 is typically large enough to expose the respective optical sensing unit 110 of the microprobe 104. In yet another embodiment, the needle 102 may have multiple openings 108, where each opening 108 is large enough to expose two or more optical sensing units 110. For example, the needle 102 may have two openings 108 and the microprobe 104 may have four optical sensing units 110, and each opening 108 defined in the needle 102 may be large enough to expose two of the optical sensing units 110.

In an embodiment, the opening 108 has a length of from about 0.5 to 20 mm. In another embodiment, the opening 108 has a length of from about 1 to 10 mm. In yet another embodiment, the opening 108 has a length of from about 3.5 to 6.5 mm. Further, the width of the opening 108 may be defined by the curve of the round or circular needle 102. In one embodiment, the width of the opening 108 may be half of the circumference of body of the needle 102. In yet another embodiment, the width of the opening may be less than half of the circumference of the body of the needle 102.

In an embodiment, the system 100 further includes a protective sheath 112 that is movable or slidable along the length of the needle 102. The sheath 112 covers the surface of the needle 102, including the opening(s) 108. In use, the protective sheath 112 may be removed (such as by moving or sliding the sheath 112 along the length of the needle 102) to expose the optoelectronics (i.e., the optical sensing unit(s) 110) of the microprobe 104. The microprobe 104 can then be used for optical sensing and needle aspiration.

As previously mentioned, the microprobe 104 may have a single optical sensing unit 110 or a plurality of optical sensing units 110. In an embodiment, the plurality of optical sensing units 110 includes at least two optical sensing units 110. In another embodiment, the plurality of optical sensing units 110 includes from two to twenty optical sensing units 110.

Figure 8:
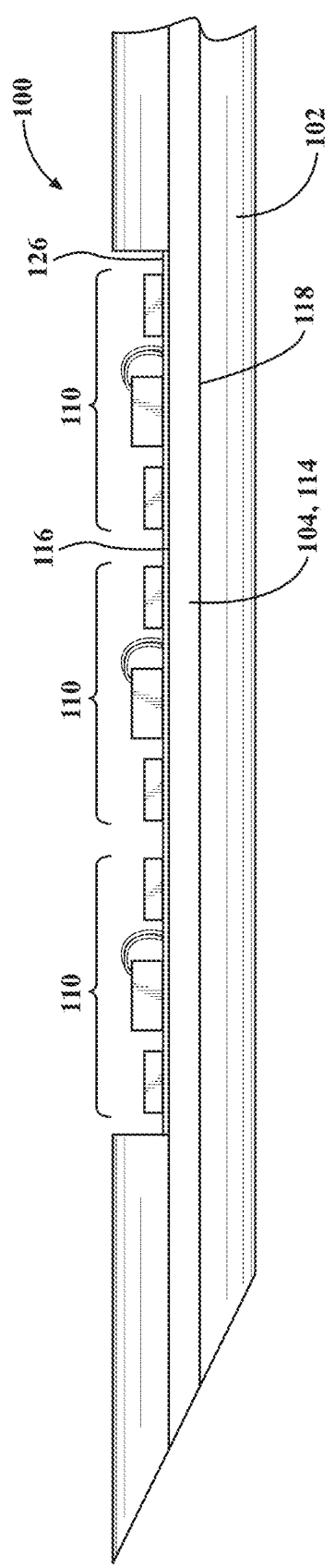
FIG. 8 is a semi-schematic side view of another embodiment of the system for analyzing tissue, where the microprobe has a plurality of optical sensing units coupled to one of the surfaces of the microprobe.

In an embodiment, the microprobe 104 has first 116 and second 118 opposing surfaces, and the single optical sensing unit 110 may be coupled to one of the first 116 or second 118 opposing surfaces. In instances where the microprobe 104 has multiple optical sensing units 110, all of the optical sensing units 110 may be arranged on the first 116 or second 118 opposing surfaces of the microprobe 104. As shown in FIG. 8, for example, the microprobe 104 has three optical sensing units 110, all of which are coupled to the first surface 116 of the microprobe 104. As also shown in FIG. 8, the plurality of optical sensing units 110 are linearly arranged on the first surface 116 and along the longitudinal axis A of the microprobe 104.

Figure 9:
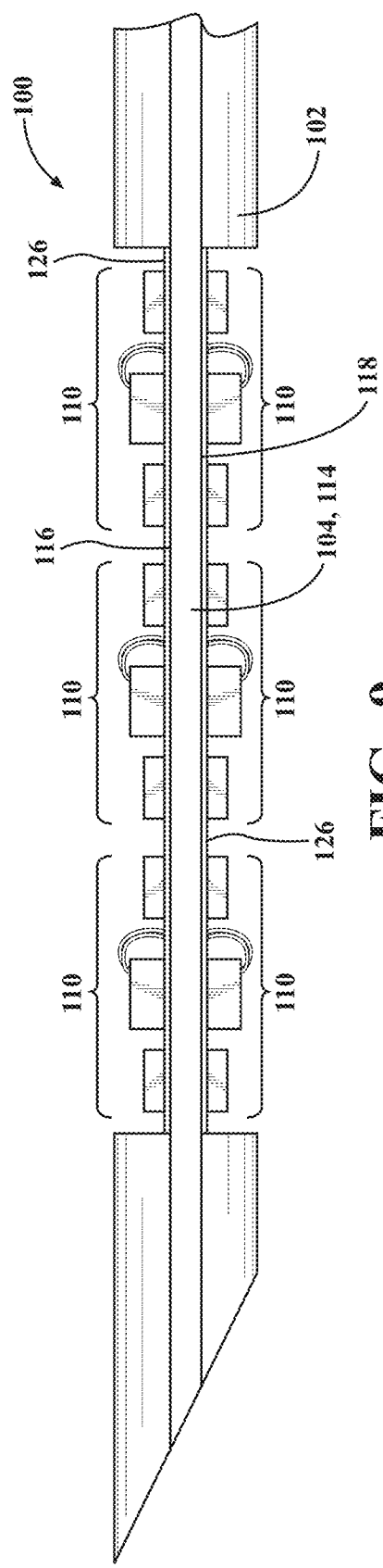
FIG. 9 is a semi-schematic side view of another embodiment of the system for analyzing tissue, where the microprobe has a plurality of optical sensing units coupled to both of the opposing surfaces of the microprobe.

In another embodiment, the microprobe 104 includes at least one optical sensing unit 110 coupled to each of the first 116 and second 118 opposing surfaces. As shown in FIG. 9, for example, the microprobe 104 has six optical sensing units 110, with three of the optical sensing units 110 coupled to the first surface 116 of the microprobe 104 and the remaining three optical sensing units 110 coupled to the second surface 118 of the microprobe 104. As also shown in FIG. 9, the three optical sensing units 110 are linearly arranged on the first surface 116 of the microprobe 104, and the remaining three optical sensing units 110 are linearly arranged on the second surface 116 of the microprobe 104. It is to be understood that the microprobe 104 may have any number of optical sensing units 110 on one or more surfaces 116, 118 of the microprobe 104. It is further to be understood that the number of optical sensing units 110 coupled to the first surface 116 of the microprobe 104 can be the same or different than the number of optical sensing units 110 coupled to the second surface 118 of the microprobe 104. With multiple optical sensing units 110 linearly arranged along the longitudinal axis A, the microprobe 104 has volumetric mapping capabilities with linear translation. Further, with multiple sensing units 110, the microprobe 104 can assess or interrogate tissue over an extending tissue volume.

Details of the optical sensing unit 110 will now be described at least with reference to FIGS. 2-5B. In an embodiment, the optical sensing unit 110 includes at least one first light source 120 and at least one second light source 122, and the detector 124 is disposed between the first 120 and second 122 light sources. In a non-limiting example shown in FIGS. 2 and 3, the optical sensing unit 110 has a detector 124 arranged between and electrically isolated from a first light source 120 and a second light source 122. In another non-limiting example as shown in FIG. 4, the optical sensing unit 110 has a detector 124 arranged between and electrically isolated from a plurality of first light sources 120 and a plurality of second light sources 122. In the example shown in FIG. 4, the first light sources 120 are arranged in parallel at one side of the detector 124, and the second light sources 122 are arranged in parallel at the opposing side of the detector 124. In the example shown in FIGS. 5A-5B, the optical sensing unit 110 has a first light source 120 and a plurality of second light sources 122, with the plurality of second light sources 122 arranged in series. In embodiments where the optical sensing unit 110 has a plurality of first light sources 120 and/or a plurality of second light sources 122, the optical sensing unit 110 can have any number of first 120 and second 122 light sources, and the light sources 120 and 122 can be arranged in any desirable manner (such as in parallel, in series, e.g., aligned along the longitudinal axis A, scattered, etc.) at their respective sides of the detector 124. In addition, the plurality of first light sources 120 may be the same or different from one another, and the plurality of second light sources 122 may be the same or different from one another. In a non-limiting example, and with reference to FIGS. 5A-5B, the first light source 120 may be a blue light-emitting diode (LED), and the second light sources 122 may include a red LED and a near-infrared LED. In this embodiment, the red LED is positioned adjacent the detector 124, and the near-infrared LED is positioned adjacent the red LED such that the red LED is located between the detector 124 and the near-infrared LED. With different first light sources 120 and/or different second light sources 122, multiple diagnostically-relevant wavelengths can be covered which expands the sensing capacity of the microprobe.

Figure 10:
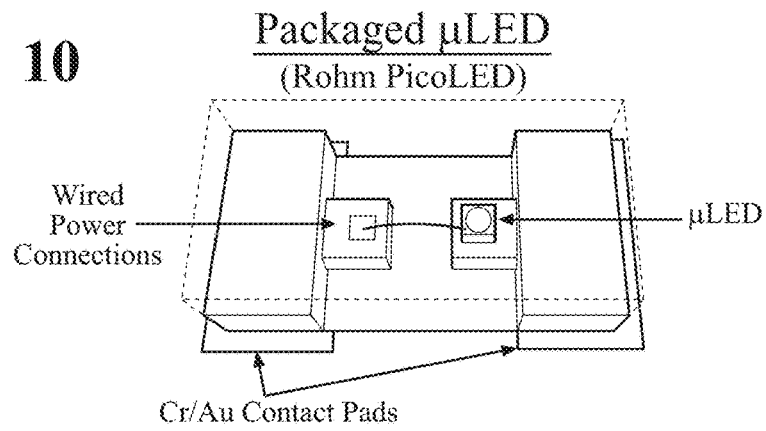
FIG. 10 illustrates an example of a packaged µLED for first and second light sources of an embodiment of the optical sensing unit.

The first 120 and second 122 light sources are chosen from any suitable optical/light source having sufficient power (e.g., up to about 0.05 W) at diagnostically-relevant wavelengths and relatively low power consumption. Non-limiting examples of diagnostically-relevant wavelengths include wavelength range for ultraviolet light, wavelength range for visible light, wavelength range for near-infrared light, and wavelength range for infrared light. For sensing, the optical/light sources 120, 122 can each operate up to about 0.05 W without damaging the tissue. In a non-limiting example, the optical power range of the optical/light sources 120, 122 is from about 1 to 50 mW. One non-limiting example of a suitable light source for the first 120 and second 122 light sources is a packaged µLED or surface mounted LED, such as a Rohm PicoLED as illustrated in FIG. 10. Another non-limiting example of a suitable light source for the first 120 and second 122 light sources is a die-level chip LED, either packaged or non-packaged. Yet another non-limiting example of a suitable light source for the first 120 and second 122 light sources is a small-sized laser diode. In an embodiment, each of the first 120 and second 122 light sources may be a µLED emitting light within the visible spectrum. In another embodiment, the first light source 120 may be a µLED emitting a red light and the second light source 122 may be a µLED emitting a blue light. In yet another embodiment, the first light source 120 may be a µLED emitting light at a wavelength of from 600 to 700 nm, and the second light source 122 may be a µLED emitting light at a wavelength of from 400 to 500 nm. While the present embodiment has been described as the first light source 120 emitting a red light and the second light source 122 emitting a blue light, it is to be understood that the light sources 120, 122 can be reversed. Said differently, in another embodiment, the first light source 120 can emit a blue light while the second light source 122 can emit a red light.

Additionally, with multiple optical sensing units 110, the arrangement of the first and second light sources 120, 122 can be consistent with each sensing unit 110 (e.g., the first light source 120 emits a red light while the second light source 122 emits a blue light) or can be random (e.g. the first light source 120 emits a red light in one or more of the optical sensing units 110, while the first light source 120 emits a blue light in the remaining optical sensing unit(s) 110). Typically, the first 120 and second 122 light sources have wavelengths centered on 630 nm and 470 nm, respectively, which provides optical data in two diagnostic regimes to successfully differentiate normal from adenocarcinoma tissues. For instance, the optical data includes a reflectance intensity, and an increase in the reflectance intensity at about 470 nm is typically attributed to an increase in cell nuclei diameter which typically increases during cancer formation. Further, a reflectance intensity at about 630 nm typically serves as a reference intensity that is independent of local tissue absorption and scattering properties.

Figure 11:
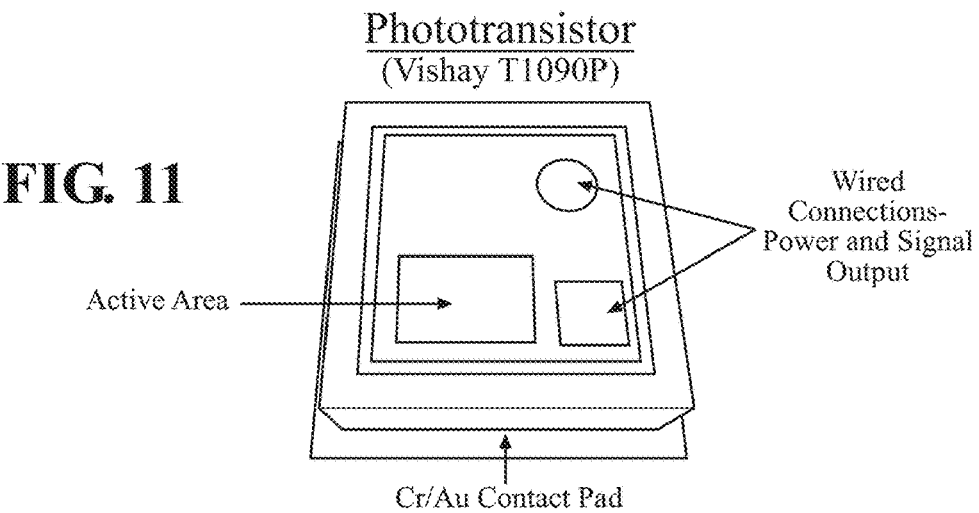
FIG. 11 illustrates an example of a phototransistor for a detector of an embodiment of the optical sensing unit.

The detector 124 is chosen from any suitable detector, such as a photodiode (such as an Avalanche photodiode (APD)), a photodetector, a phototransistor, and a silicon photomultiplier (SIPM). The detector 124 has a high radiant detection efficiency (such as about 0.77 mA/mW/cm$^2$) and adequate sensitivity for wavelengths of light within the visible spectrum. In an embodiment, the detector 124 is a phototransistor, such as a Vishay T1090P available from Vishay Intertechnology (Malvern, Pa.), as illustrated in FIG. 11. In an embodiment, the detector 124 has a peak spectroscopic sensitivity of from about 850 to 900 nm.

As shown at least in FIGS. 2-5B and 7-9, each optical sensing unit 110 includes the detector 124 arranged between the first 120 and second 122 light sources. Further, the detector 124 is electrically isolated from (i.e., is spaced from or does not touch) the first 120 and second 122 light sources. Further, the first 120 and second 122 light sources are arranged on opposing sides of the detector 124. The first 120 and second 122 light sources (with the detector 124 arranged between them) are separated by a distance of from about 0.4 to 5 mm, measured from the center of the first light source 120 to the center of the second light source 122 (i.e., $D_1+D_2$ shown in FIG. 3, for example). In another embodiment, the center-to-center spacing between the first 120 and second 122 light sources is from about 1 to 3 mm. In yet another embodiment, the center-to-center spacing between the first 120 and second 122 light sources is about 2 mm.

The separation or distance between the first 120 and second 122 light sources (with the detector 124 between them) may be referred to as a center-to-center spacing or source-detector separation (SDS). By controlling the center-to-center spacing or source-detector separation, one can also control a penetration depth of light. Typically, the maximum light penetration depth is half of a given SDS in biological tissues. However, maximum light penetration depth may also be affected by the absorption properties of the tissue. Hemoglobin is one of the chromophores that attenuates an incident light and its absorption characteristics is dependent on the wavelength and oxygen-binding status. Hemoglobin absorption is much lower in a near-infrared (NIR) wavelength range (700 to 900 nm) than a visible wavelength range (400 to 700 nm). Accordingly, the maximum SDS of the sensing unit 110 using visible light (such as red and blue) may be limited to a few millimeters, an NIR LED could have a significantly larger SDS leading to deeper penetration and larger tissue interrogation volume.

In an embodiment, the separation between the detector 124 and the first light source 120 may be substantially the same as the separation between the detector 124 and the second light source 122. With a substantially same separation between the detector 124 and each of the first 120 and second 122 light sources, optical measurements can be obtained at substantially the same penetration depths for different wavelengths. It is to be understood, however, that the separation between the detector 124 and each of the first 120 and second 122 light sources can be different depending, at least in part, on how optical measurements are chosen to be made.

In a non-limiting example, the size of each of the light sources 120, 122 and the detector 124 can be up to about 700 µm. In another non-limiting example, the size of each of the light sources 120, 122 and the detector 124 can be from about 100 to 700 µm.

Figure 25A:
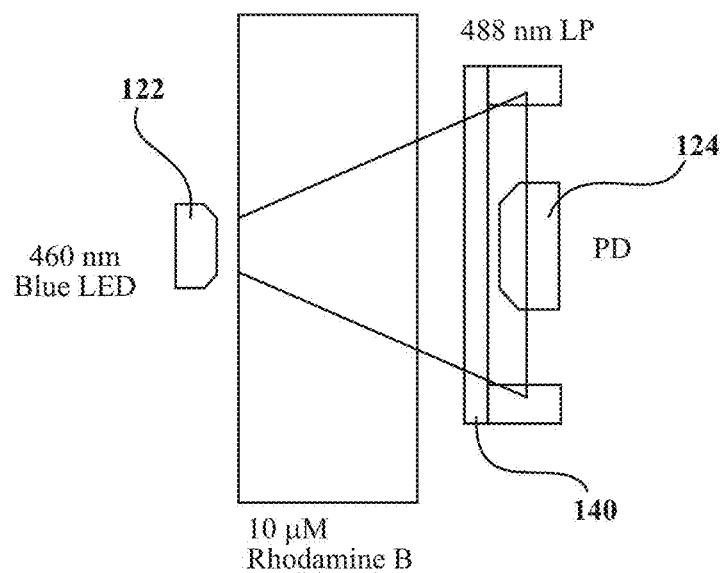
FIG. 25A is a schematic illustration of a fluorescence measurements setup including a long pass filter with 488 nm cutting wavelength positioned closely to the detector so that just light passed the long pass filter is detectable by the detector.

In an embodiment, and as shown, e.g., in FIG. 25A, the system 100 further includes at least one filter 140 adjacent the detector 124. In a non-limiting example, the filter 140 is a long pass filter. The filter 140 is designed to cut the wavelength of light, and is usable for measuring fluorescence of the interrogated tissue.

In an embodiment, and as shown at least in FIGS. 2 and 3, the system 100 further includes a microfabricated printed circuit board 126 disposed on the platform 114, and the sensing unit(s) 110 is/are directly coupled to the printed circuit board 126. In instances where the system 100 includes optical sensing unit(s) 110 coupled to the first surface 116, the system 100 would further include a printed circuit board 126 coupled to the platform 114 and the optical sensing unit(s) 110 would be coupled to the printed circuit board 126. In instances where the system 100 also includes optical sensing unit(s) 110 coupled to the second surface 118, then the system 100 would further include another printed circuit board 126 coupled to the second surface 118 and the optical sensing unit(s) 110 would be coupled to the printed circuit board 126. The system 100 may also include wires and/or connections to connect the microprobe 104 to an external device(s), such as a controller, an optical data reader, a power supply, and/or the like. Alternatively, and in an embodiment, the microprobe 104 can operate on battery power and transmit data via a wireless connection. Without physical wiring, there is typically easier access to the target tissue and more freedom to move around the subject or person during a procedure.

Wireless transmission of power and data can address potential problems of long wire connection in the system 100 (such as, e.g., resistance increase, failure, infection and manufacturing cost). A radio frequency (RF) telemetry circuit can be integrated in a CMOS process on a chip that fits into the hollow needle 102. For instance, for a 19 gauge needle, the chip size can be 0.8 mm×up to few millimeters (w×l). The telemetry circuit may include a voltage regulator for power conversion, clock generator, demodulator, pre-amplifier, analog-digital converter and transmitter. An antenna in the telemetry chip integrated with the system 100 may receive both power and data via an inductive link from an external transmitter unit. The circuit generates power from radio frequency (RF) carrier signals, demodulates the control data and produces a clock signal to operate the electronics. The control circuit drives the light sources 120, 122 (LEDs) and the signal measured by the detector 124 in the optical sensing unit 110 is pre-amplified, digitized and transmitted back to the outside through a wireless link. Besides the electromagnetic RF, infrared or acoustic energy can be used to implement wireless communication.

Figure 12:
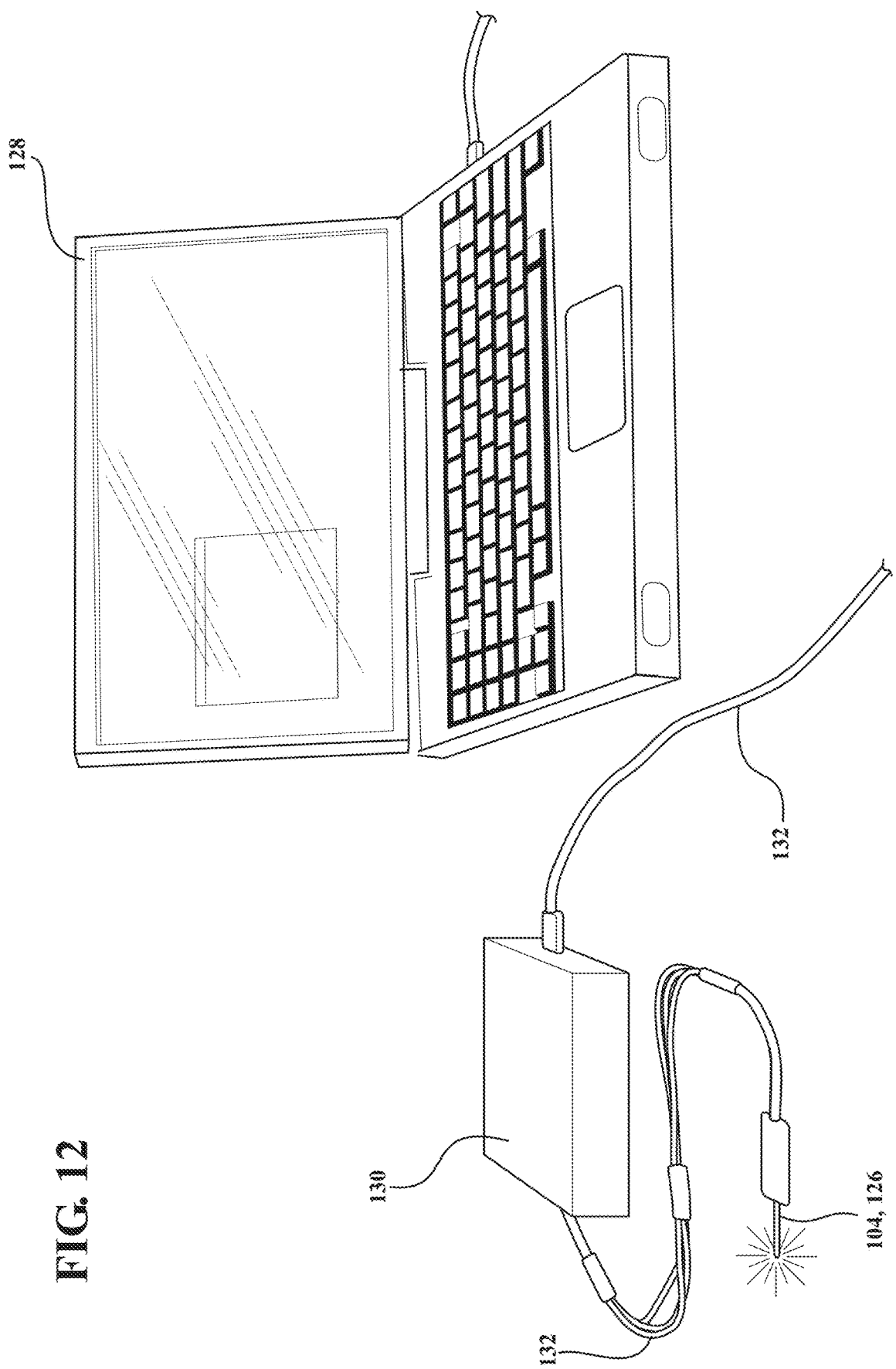
FIG. 12 illustrates an embodiment of the system for analyzing tissue including a needle microprobe connected to a printed circuit board, a control electronics box, and a computer including graphic user interface (GUI) software.

The system 100 may also be coupled to a computer 128 as shown in FIG. 12, which has a memory for storing an application including computer-readable instructions for utilizing the optical data obtained by the system 100 to obtain factors of the interrogated tissue. As also shown in FIG. 12, the system 100 includes a control electronics box 130 and the computer 128 with a graphic user interface (GUI). FIG. 12 also shows the circuit board 126, which is external to the microprobe 104. This setup is used to test the microprobe 104 and circuit board 126 *ex vivo*. Further, wires 132 commercialized for neural recording may be used to connect the microprobe 104 to the electronics box 130. A single USB cable can be used to supply DC power and transmit commands to the electronic box 130, and can be used to transmit data from the microprobe 104 to the electronic box 130 and to the computer 128. Upon receiving the optical data from the microprobe 104, the application resident on the computer 128 may be used to generate factors for clinical evaluation of the interrogated tissue. Further details of the application and how utilizing the optical data obtained from the system 100 is described below.

Fabrication of a First Prototype Board for the System 100

Figure 13:
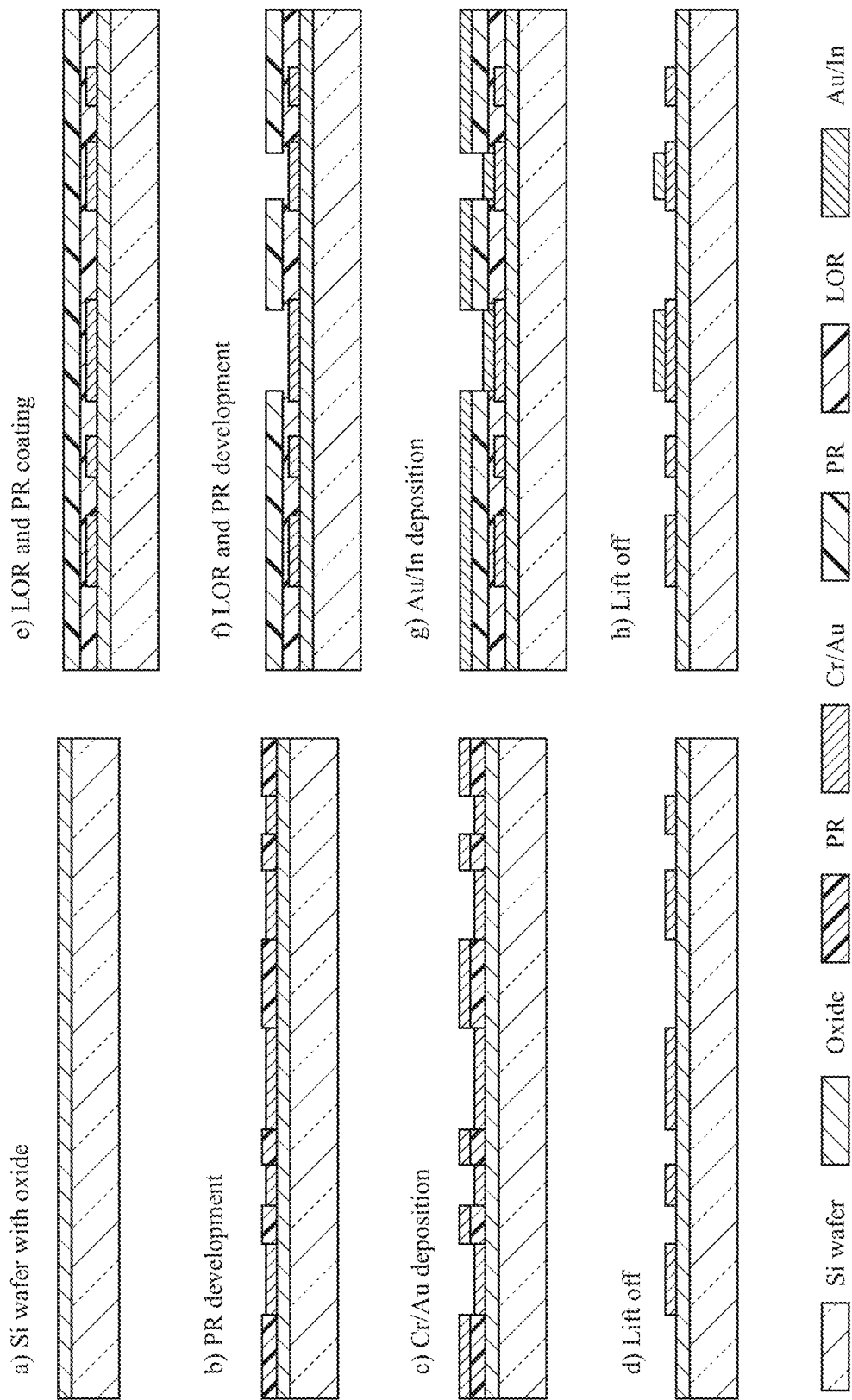
FIG. 13 illustrates an example of a process for fabricating a first prototype board for the microprobe.

Referring now to FIG. 13, a prototype board for the system 100 may be fabricated with known microfabrication techniques to form silicon-based neural probes. Further, the system 100, particularly the microprobe 104 may be fabricated on a silicon-on-insulator (SOI) wafer with electrical isolation. For example, the microprobe 104 may be fabricated on a silicon wafer with 500 µm thickness with a 2 µm thick oxide layer on top for insulation. As shown in FIG. 13, in step a), Cr/Au may be patterned by a lift-off process for pad contacts for the light sources 120, 122 and the detector 124, and interconnections to external electrodes. During the lift-off process, a photoresist may be spin-coated and patterned by photolithography, as shown in step b). In step c), Cr/Au (30/200 nm) may be deposited onto the patterned photoresist by an electron beam evaporator. Then during step d), the photoresist with undesired Au/Cr layer may be lifted away to leave the Cr/Au pattern.

As shown in step e) of FIG. 13, indium (In)—Au eutectic bonding may be used to bond the bottom side (i.e., the Au side) of the first light source 120 and the detector 124. Accordingly, indium pads may be defined within the Cr/Au pattern by a second lift-off process. In step e), to pattern thick (e.g., 6 µm) indium pads, a lift-off resist may be coated as an under-cut layer in a bi-layer lift-off process. In step f), the photoresist may be coated onto the lift-off resist and the photoresist and lift-off resist may be developed by photolithography. In steps g) and h), a lift-off process following by soaking the device in a positive red stripper at about 85° C. for about 20 minutes and sonication until the pattern is completely defined.

Assembly of the System 100 from the First Prototype

A non-limiting example of a method for assembling the system 100 is described below with reference to FIG. 14, steps a)-e). As shown in FIG. 14, prior to assembly, and as shown in step a), the method includes rinsing the fabricated bare board by immersing the board into acetone for about 10 minutes and then immersing the board in isopropyl alcohol for about 5 minutes. As shown in step b) in FIG. 14, the method further includes In—Au eutectic bonding by employing customized recipes to bond the bottom side of the detector 124 (PD) and the first light source 120 (Red LED) onto the defined indium pads. A temperature profile may be programmed to provide the optimal temperature in a rapid thermal process tool (e.g., Jetfirst-100, Jipelec, Montpellier, France). Au—In bonding may be provoked by maintaining a temperature of about 250° C. for about 5 minutes. Further, since the bottom side metal of the second light source 122 (blue LED) die (e.g., 460DA3547, Cree, Durham N.C.) is an Au-Sin alloy (solder), which is a eutectic alloy, the temperature may be raised up to about 280° C. in 5 seconds based on a recommended flux eutectic reflow process. Higher temperatures (e.g., 290° C. and 300° C.) may be utilized to find an optimal condition. It is to be understood that once eutectic bonding is formed between the Au and In, higher temperature for Au—Sn eutectic bonding (e.g., about 280° C.) than the eutectic temperature of In—Au (e.g., 250° C.) does not affect the bonding status.

Figure 16A:
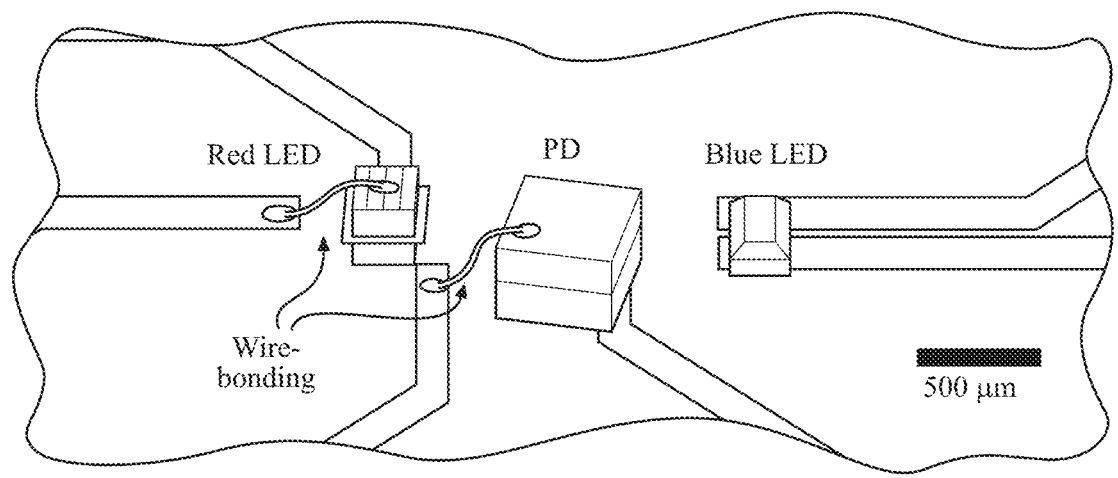
FIG. 16A is an enlarged view of bonded light sources (µLEDs) and detector of the assembled prototype board for the optoelectronic microprobe.
Figure 16B:
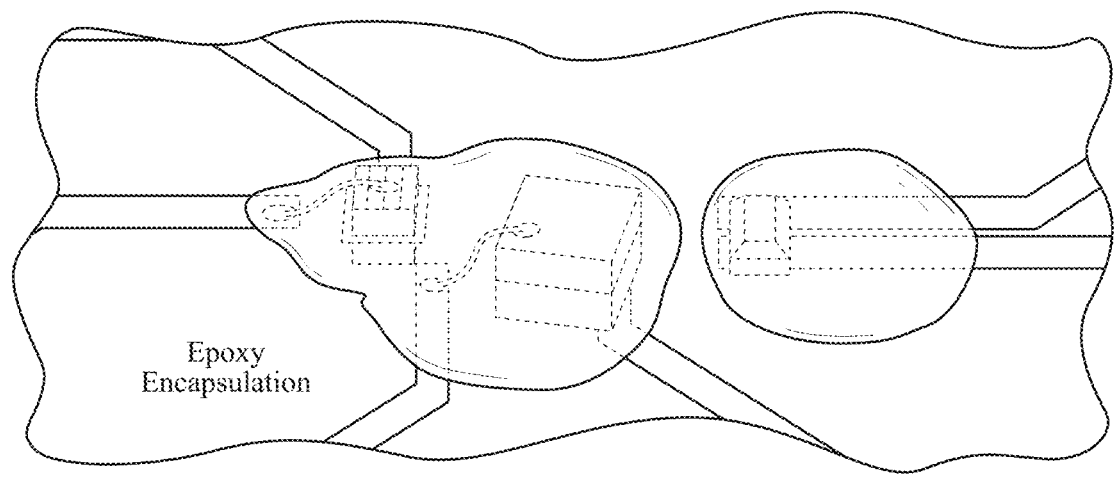
FIG. 16B is an enlarged view of an epoxy encapsulation of the components of the assembled prototype board for the optoelectronic microprobe.

The method further includes wire-bonding the cathode pad on the top of the detector 124 (photodiode) and the first light source 120 (Red LED) to the interconnections at the bottom of the board via, e.g., 0.007 inch Au wire. Optically transparent epoxy (e.g., NOR-61, Norland, Cranbury, N.J.) may be used to encapsulate the bonded components. In an example, a drop of the epoxy may be delivered using a 30 G-needle (available from Becton Dickinson, Franklin Lakes, N.J.) to confine the volume covering the three components. In an example, the epoxy may be cured using a 365 nm ultraviolet with exposure for about 10 seconds. An example of an assembled prototype board for the system 100 is shown in FIG. 15. Further, FIG. 16A is an enlarged view of eutectic bonded LEDs and photodiode of the assembled prototype, and FIG. 16B is an enlarged view of a portion of the prototype showing an epoxy encapsulation to protect the wire bonding and components of the system 100.

Fabrication of a Second Prototype Board of the Microprobe

Figure 17:
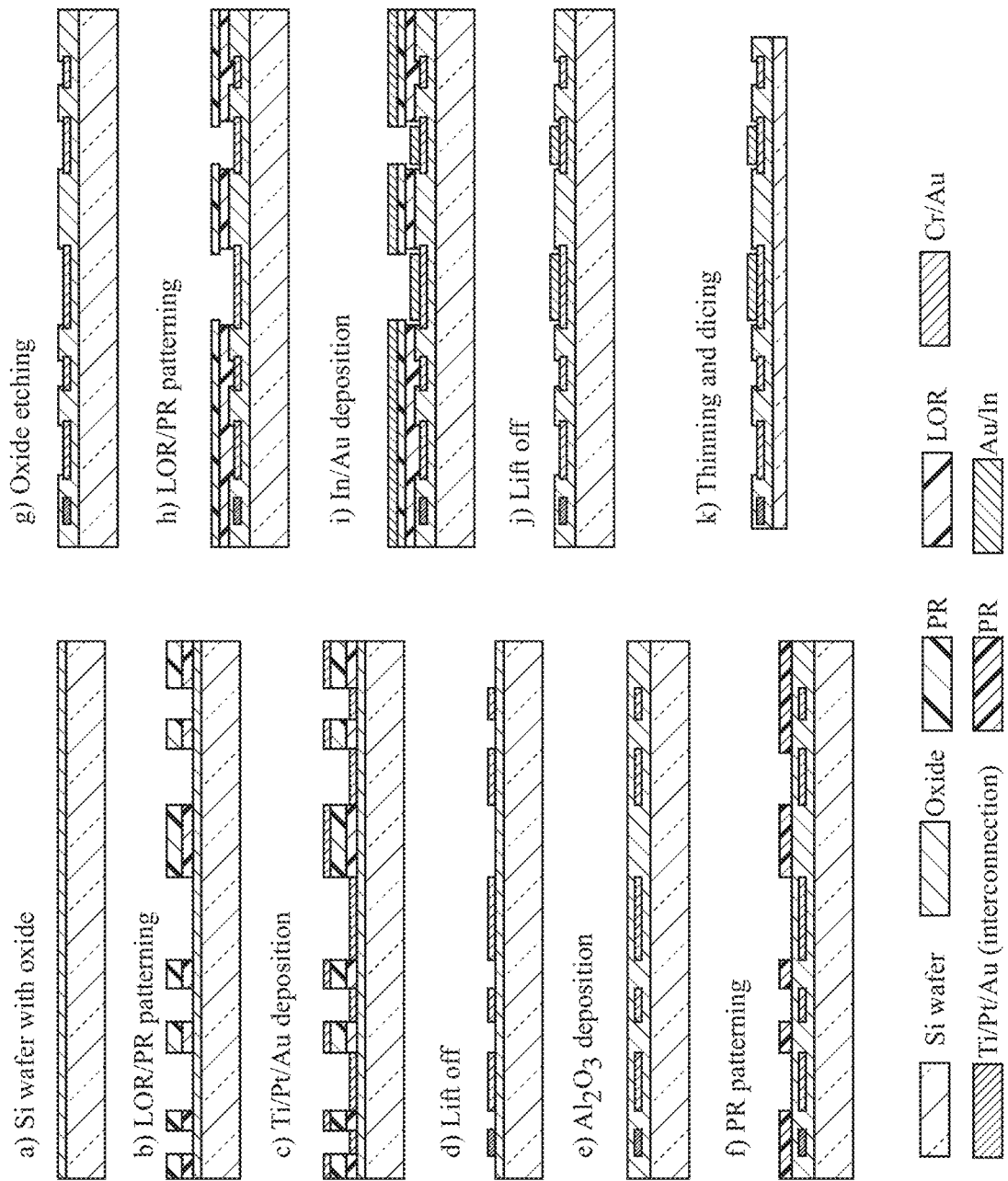
FIG. 17 illustrates an example of a process for fabricating a second prototype board for the microprobe.

An embodiment of another prototype fabrication process is described below. The prototype board for the system 100 may be fabricated on a silicon wafer with 500 μm thickness (2 μm-thick oxide layer on the top for insulation) based on the microfabrication procedure illustrated in FIG. 17. This fabrication process may be used to produce a prototype having a 25 mm length, a 0.75 mm width, and a 0.15 mm thickness, which fits an inner diameter of 0.85 mm of a 19 gauge aspiration needle, as shown in FIG. 17. An additional thinning step is added to the fabrication method described above to reduce the thickness of a conventional 10-inch silicon wafer. Further, this fabrication process includes a step for adding a top insulation layer for interconnection protection. The second prototype may be used to verify the technical feasibility of a FNA needle-compatible microprobe for tissue phantoms and ex vivo tissue assessment.

As shown in FIG. 17, the prototype may be fabricated as follows. In step a), Ti/Pt/Au and Au/In layers are patterned by a lift-off process for pad contacts of the light sources 120, 122 (light emitting diode (LED)) and the detector 124 (photodiode (PD)), and interconnections for external electrodes. Then, a liftoff resist (LOR) and photoresist (PR) is coated and baked. In step b), the photoresist is exposed, and the liftoff resist and photoresist are developed. In step c), Ti/Pt/Au (200/300/4500 Å) is/are deposited on the patterned photoresist by an electron beam (E-beam) evaporator (such as an Enerjet Evaporator). In step d), the photoresist with the undesired layer is lifted away to leave a Ti/Pt/Au pattern. In step e), to provide electrical insulation over patterned interconnections, atomic layer deposition (ALD) may be used to deposit a 300 Å-thick $Al_2O_3$ layer for enhanced adhesion and insulation before $SiO_2$ (1 μm) deposition by plasma-enhanced chemical vapor deposition (PECVD). In step f), the photoresist is coated, baked, exposed, and developed for patterning. In step g), the oxide layer is etched for bonding pads contact, while the oxide layer on the interconnections remains for insulation. In step h), to bond the bottom side (Au) of the first light source 120 (red LED) and the detector 124 (photodiode), an indium (In)—Au eutectic bonding process is chosen. Thus, In-pads are defined within bonding pads by the second lift-off process. To pattern thick (6 μm) In-pads, the liftoff resist (LOR, LOR 30B, Microchem) is coated as an under-cut layer in a bi-layer lift-off process. The photoresist is coated onto the liftoff resist, and the photoresist and liftoff resist are developed. In step i) an electron-beam evaporator (Cooke Vacuum Products) is used to deposit Au/In (1 nm/6 μm). In step j), a lift-off process is used followed by soaking in a positive resist stripper (PRS) in about 85° C. for about 20 minutes and sonication until the pattern is completely defined. In step k), the wafer is thinned down to about 150 μm by removing the backside of the wafer and releasing each probe unit.

Accordingly, utilizing the fabrication method described above, the assembled prototype includes eutectic bonding of the first light sourced 120 (red LED) and detector 124 on the fabricated board, eutectic bonding of the second light source (blue LED) on the fabricated board, and wire-bonding of the red LED, the blue LED, and the detector in the fabricated board. The resultant board may be connected to a printed circuit board, and the electrodes may be wire-bonded in the board and the printed circuit board. Epoxy may be used on the wire-bondings for protection. The board may then be inserted into a needle 102 (such as a 19 gauge aspiration needle), and epoxy may be used in the area where the needle contacts the printed circuit board. Epoxy may also be used on the sensing area through the opening (or viewing window) of the needle.

Assembly of the System 100 from the Second Prototype

The assembly of the system 100 from the second prototype board may be accomplished utilizing the same process described above for the assembly of the system 100 from the first prototype board.

System Controller Design and Development

In an embodiment, the system 100 further includes the computer 128, which can operate as a controller that sequences excitation and detection for each sensing unit 110. Combined with on-board signal processing electronics, the computer 128 enables real-time monitoring of the diffuse reflectance intensity and calculation of diagnostic parameters (such as $R_{470nm}/R_{630nm}$) at tissue interrogation sites. Accordingly, the microprobe 104 may be connected (such as with a wire) to an external circuit. The external circuit may include a multi-channel μLED current driver and trans-impedance amplifiers. A single supply low noise LED current driver may be implemented by employing a current output digital-analog converter. Emitted μLED light intensity may be adjusted with current level controlled digitally by a controller (such as a microcontroller). The trans-impedance amplifier generally converts the detector 124 current to a voltage signal with an amplification of about $10^5$. A programmable gain amplifier may be used to enable an additional gain setting, which provides a high dynamic range. The amplified voltage may be filtered by a second order, low-pass filter (e.g., with a cut-off frequency of about 1 kHz) to yield a high SNR signal. A 16-bit analog-digital converter may be used to read the resulting voltage at a range of about 50 kHz. Further, a microcontroller may be employed to control all the excitation and detection procedures, including switching the excitation sequence of the light sources 120, 122, adjusting the light source (μLED) intensity and trans-impedance amplifier gain, and reading ADC values.

Hardware for the computer 128 may be controlled with GUI software. For example, the GUI software may enable users to adjust the light intensity of the light sources 120, 122, as well as their frequency and duration. For detection, the GUI software may also allow users to set an appropriate gain for amplification, and displays and records the absolute intensity of detected light for the different wavelengths along with the ratio metric value.

A specific example of the controller design and development is described in detail below. A custom electronic control module may be designed and developed to drive the light sources 120, 122, read the detected photons on the detector 124, and control the overall sensing process. A microcontroller unit based on a 32-bit ARM core (e.g., ST32F405OE, STMicroelectronics, Geneva, Switzerland) may be employed to sequence the two light sources 120, 122, set the gain on the PGA, read the ADC values, and send the data to the computer 128 via, e.g., universal asynchronous receiver/transmitter (UART) communication.

A single supply low noise LED current driver may be implemented by employing a current output digital-analog converter (such as a DAC AD5452 Analog Device). A trans-impedance amplifier converts the phototransistor current to a voltage signal with an amplification of about $10^5$. A programmable gain amplifier (e.g., a LTC6910 available from Linear Technology (Milpitas, Calif.)) may enable an additional gain setting, which provides a high dynamic range. Further, the amplified voltage may be subsequently filtered by a second order low-pass filter (e.g., having a cut-off frequency of about 1 kHz) to yield a high SNR signal. A 16-bit analog-digital converter (such as an ADS1115 available from Texas Instruments (Dallas, Tex.)) may be used to read the resulting voltage at a rate of about 50 kHz.

System Integration

Custom-designed electronics has been developed to control the microprobe. The electronics has four-channel LED drivers and two-channel trans-impedance amplifiers, followed by a programmable gain amplifier and low-pass filtering for phototransistor signal conditioning. The microcontroller executes A/D conversion and transmits the data to the computer 128 via, e.g., a USB connection. The application is written in C # language, sends commands to control the LED driver and TIA, and receives and displays the data from the electronics.

Method of Analyzing Tissue Utilizing the System 100

A method of analyzing tissue (such as pancreatic tissue) utilizing the system 100 will now be described. The method includes the steps of directing a light from the light sources 120, 122 toward the tissue, obtaining optical data while the light is being directed toward the tissue, and utilizing the optical data to analyze the tissue. In an embodiment, the method further includes the steps of introducing the needle 102 (with the microprobe 104 carried by the needle 102) into a body (such as a human body during a EUS-FNA procedure). Upon identifying the tissue, the method includes retracting the sheath 112 from the needle 102 to expose the optical sensing units 110. Utilizing control electronics external to the needle 102, the method includes sending a signal from the electronics to the light sources 120, 122 (such as through a long wire through a EUS-FNA channel) to switch on the first light source 120. In response, the first light source 120 emits a red light. Once the red light is emitted from the first light source 120, the detector 124 detects reflected light and sends a detection signal to the electronics. In instances where the system 100 includes a filter 140 adjacent the detector 124, the detector 124 alternatively detects fluorescence light and sends a detection signal to the computer 128.

In an embodiment, the method further comprises sending another signal from the electronics to the light sources 120, 122 (such as through a long wire through a EUS-FNA channel) to switch on the second light source 122. In response, the second light source 122 emits a blue light. Once the blue light is emitted from the second light source 122, the detector 124 detects reflected light and sends a detection signal to the electronics. In instances where the system 100 includes a filter 140 adjacent the detector 124, the detector 124 alternatively detects fluorescence light and sends a detection signal to the computer 128.

Utilizing the detected optical data (e.g., the two reflectance intensities), the step of analyzing the data includes calculating a reflectance ratio (described in detail below) and displays the ratio in the GUI monitor of the computer 128.

The method described above may be accomplished in real-time, or close to real-time (e.g., within 1 second). The ratio values on the screen may then be utilized, such as by a physician, to characterize the interrogated tissue and/or to obtain additional information on the interrogated tissue that may assist with other diagnostic procedures.

The System 200

Figure 18:
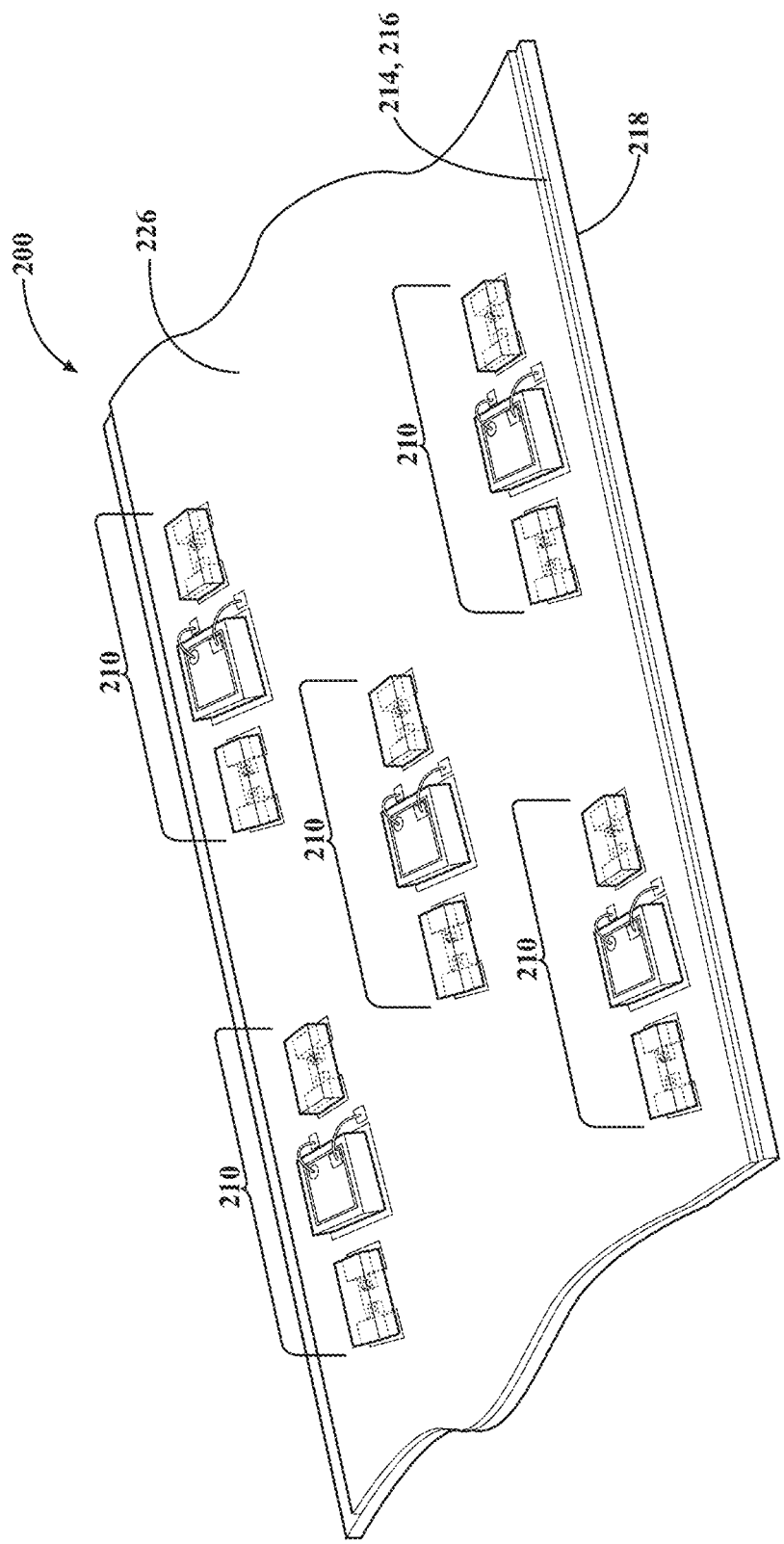
FIG. 18 is a semi-schematic plan view of another embodiment of a system for analyzing tissue.

Another embodiment of the system 200 is shown in FIG. 18. In this embodiment, the system 200 includes a platform 214 such as a flexible board or sheet, and further includes at least one optical sensing unit 210 coupled to the platform 214. As shown, the system 200 further includes a printed circuit board 226 coupled to the platform 214, and the optical sensing unit(s) 210 is/are directly coupled to the printed circuit board 226. Further, the platform 214 has first 216 and second 218 opposed surfaces, and the optical sensing unit(s) 210 is/are coupled to at least one of the first 216 and second 218 opposed surfaces. In an embodiment, the system 200 includes a plurality of optical sensing units 210 arranged on at least one of the opposed first 216 and second 218 opposed surfaces of the flexible sheet/platform 214. The optical sensing units 210 may be arranged on the first 216 and/or second 218 opposed surfaces according to a predefined pattern. Alternatively, the optical sensing units 210 may be randomly arranged on the first 216 and/or second 218 opposed surfaces. In instances where the system 200 includes optical sensing unit(s) 210 coupled to the second surface 218, then the system 200 would further include another printed circuit board coupled to the second surface 218 and the optical sensing unit(s) 210 would be coupled to the printed circuit board. In a non-limiting example, the size of each of the light sources and the detector of each of the optical sensing units 210 of the system 200 can be up to about 2 mm. In another non-limiting example, the size of each of the light sources and the detector of each of the optical sensing units 210 can be from about 1 to 2 mm.

The system 200 may be used, for example, for external tissue diagnostics, such as for detecting skin cancers. For instance, the flexible sheet/platform 214 may be wrapped around or otherwise applied to the suspect skin tissue, and the system 200 can obtain optical data for subsequent tissue analysis and diagnostics.

In addition, the system 200 may include all of the features described above with reference to the system 100, including a computer, wires, connections, etc. However, since the system 200 is designed for external tissue diagnostics, the system 200 is not designed for nor does it include an aspiration needle.

Optical Data Processing

The systems 100, 200 described above may be used in an appropriate diagnostic procedure to obtain optical data which may be utilized, by the computer application, to provide factors of the tissue that can be used to render an accurate tissue diagnosis. This tissue diagnosis can lead to rapid institution of an appropriate therapy, such as surgery for resectable tumors, neoadjuvant therapy for borderline resectable disease, and definitive chemotherapy for located unresectable disease. In use, the system 100, 200 is positioned adjacent the live tissue and the sensing unit(s) 110, 210 generates pulses of light to interrogate the live tissue and obtain data pertaining to a reflectance intensity and direction of the interrogated tissue.

The presence of cancer may be determined in instances where the reflectance intensity or direction changes. Accordingly, with observing reflectance data, one can distinguish between cancerous tissue and healthy tissue.

The optical data processing application includes a ratiometric analysis algorithm and a quasi-spectral analysis algorithm to obtain useful factors for tissue diagnostics utilizing the optical data obtained from the microprobe 104. The ratiometric analysis algorithm uses a simple reflectance ratio between two discrete wavelengths. For human pancreatic tissue assessment, the reflectance ratio, $R_{470nm}/R_{650nm}$, is a suitable candidate to distinguish malignant tissues (adenocarcinoma) from non-malignant tissues including normal tissues and chromic pancreatitis. Typically, the reflectance intensities at 450 to 470 nm are significantly different among the foregoing types of tissues. This may be attributed to different scattering properties depending on nuclei size, refractive index, and collagen contents. However, the reflectance intensities at 630 to 650 nm in three tissue types are very close, which serves as a reference reading.

Employing different wavelengths related to hemoglobin absorption has a potential to assess total hemoglobin (Hb) concentration and tissue oxygenation. Ratiometric analysis based on isosbestic and non-isosbestic points has the capability to estimate tissue hemoglobin concentration and oxygenation. Isosbestic points are the wavelengths in which oxyhemoglobin and deoxyhemoglobin have substantially the same absorbance, for example, 500, 529, 545, 570 and 584 nm. Non-isosbestic points are the wavelengths showing the biggest difference in absorbance between oxy- and deoxy-hemoglobin, for example, 516, 539, 560, 577 and 593 nm. However, ratiometric analysis based on isosbestic and non-isosbestic points utilizes a full reflectance spectrum acquired by a fiber-based diffuse reflectance spectroscopy. For the optoelectronic microprobe 104, however, two light sources 120, 122 (such as two LEDs) with wavelengths as close to isosbestic and non-isosbestic wavelengths as possible can be selected to enable rapid estimation of blood parameters. Rapid and non-invasive assessment of Hb concentration and oxygenation has many clinical applications, including cancer detection, anemia detection, perfusion monitoring, etc. An advantage of the ratiometric analysis includes rapid processing time enabling real-time monitoring.

The quasi-spectral analysis can be used to analyze the full reflectance spectrum to extract biophysically relevant parameters or optical properties of the tissue directly from the microprobe 104 measurements. A photon-tissue interaction (PTI) model is used to analyze diffuse reflectance spectrum obtained from human pancreatic tissues. The PTI model is a mathematical equation based on fundamental principles for light scattering and absorption at a given fiber optic probe geometry. The PTI model calculates a reflectance spectrum from input variables including nuclei size and the refractive index of the nuclei. By fitting the PTI model to the obtained reflectance spectrum, parameters generating the least error between the model and the experiment are extracted. The original model uses a full wavelength reflectance spectrum from 400 to 700 nm with a 2 nm step for a total of 176 wavelengths.

Figure 19:
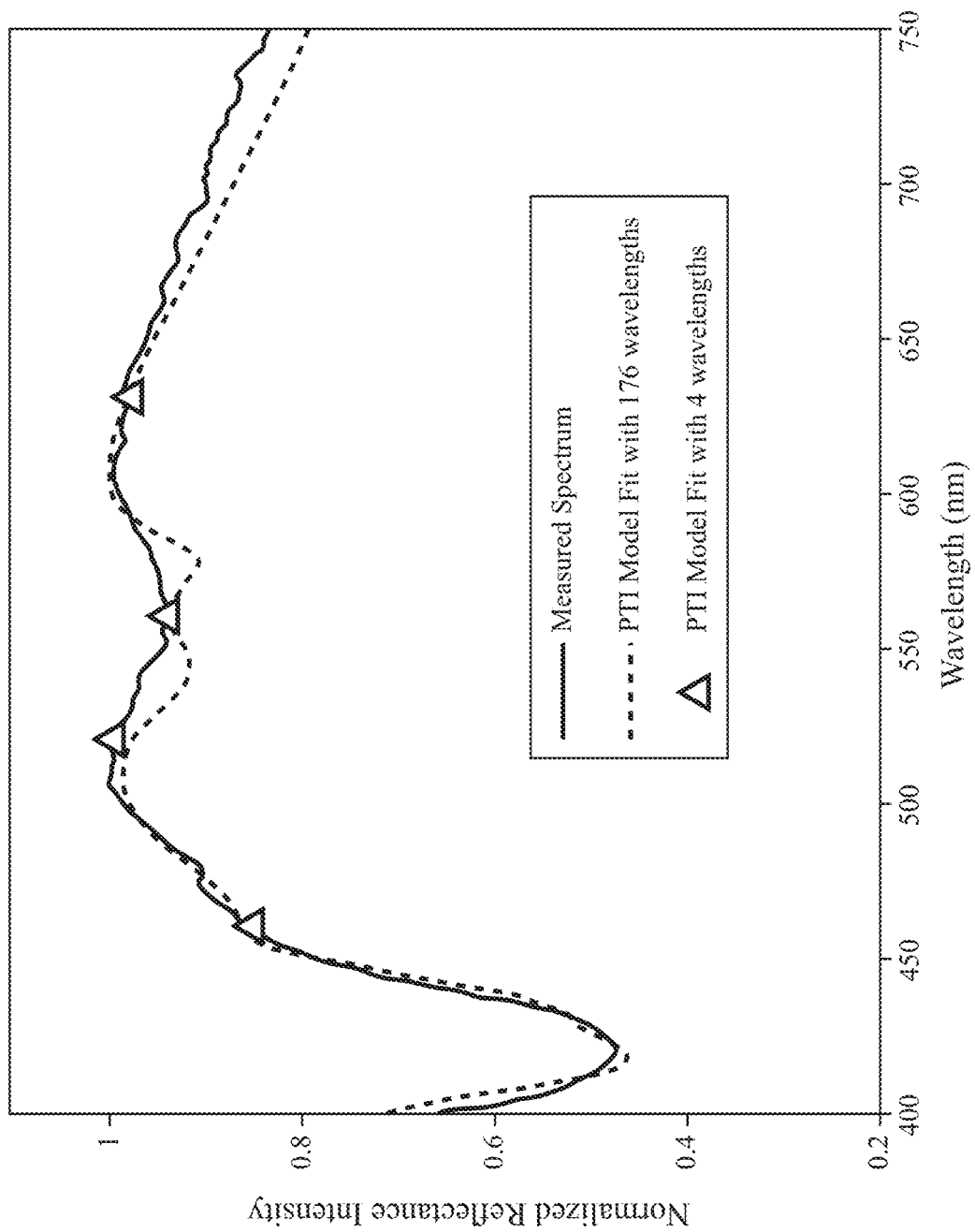
FIG. 19 is a graph showing a photon tissue interaction (PTI) model fit with 176 and 4 wavelengths, respectively, for the same measured spectrum.

To employ the PTI model for the optoelectronic microprobes that include LEDs with a narrow band, the PTI model is used with fewer wavelengths. Accordingly, to assess the feasibility of wavelength reduction to accurately extract parameters, the PTI model is performed on existing tissue reflectance dataset obtained from freshly-excised human pancreas using four wavelengths. The results are compared with the parameters extracted by a full wavelength PTI model. The four selected wavelengths are 460, 520, 560 and 630 nm. The four wavelengths represent the full spectral diagnostic information in pancreatic tissues. For example, the relative reflectance at 470 nm is associated with an increase in cell nuclei diameter, which typically increases during cancer formation. The reflectance at 520 nm and 560 nm are selected due to relatively less hemoglobin absorption, avoiding a and 13 bands of the hemoglobin. The reflectance at about 630 nm serves as a reference intensity that is relatively independent of local tissue absorption and scattering properties. Utilizing the four wavelengths, the mathematical model is capable of extracting diagnostically-relevant parameters consistent with those extracted from the full-wavelength reflectance spectra. FIG. 19 shows a representative PTI model that fits with full wavelength and the four wavelengths compared to measured reflectance spectrum.

Table 1 (shown in FIG. 20) provides two extracted parameters from three different tissue types. The results in Table 1 do not show that there is a significant difference between the PTI results using 176 and 4 wavelengths. The average difference between the two model results at the same measurement is 0.8 for nuclear size and 0.006 for refractive index, respectively. Additionally, two extracted parameters from the PTI model with 4 wavelengths can distinguish adenocarcinoma from a normal pancreas (p is greater than 0.05, Wilcoxon rank sum test). Accordingly, the results show that PTI model with a reduced number of wavelengths can produce comparable outcomes to the PTI model results with a full reflectance spectrum.

Through the results set forth above, the PTI model is capable of using reduced wavelengths. In addition, four LEDs with four different wavelengths can be allocated around the detector on the microprobe to obtain diffused reflectance intensity at each wavelength. The optoelectronic microprobe coupled with the PTI model has the potential to enable real-time monitoring of biophysically relevant parameters and performing optical biopsy during EUS procedure in clinics.

The preliminary comparison described above demonstrates the possibility of quasi-spectral sensing using the optoelectronic microprobe 104 for non-invasive assessment of biophysically-relevant parameters.

In addition to the mathematical model described above, a computational model can also be used to generate a reflectance spectrum. Monte Carlo (MC) simulation is a computational tool for modeling proton propagations inside biological tissues. Computing all travel paths of a vast amount of individual photons gives information on the overall reflectance intensity. The parameters related to photon travel such as direction, angle, and path length of each photon step are calculated based on a probability of governing physical equations rather than one deterministic equation such as the PTI model. Typically, inputs for the MC model are absorption and scattering coefficients. Multiple MC runs with a different range of absorption and scattering coefficients relevant to biological tissues can be used to create a look-up table.

The created MC look-up-table (MCLUT) is employed to produce a modeled spectrum, which compares with the measured spectrum in the fitting algorithm for inversion process to extract biophysically-relevant parameters. As fewer wavelengths work for the PTI model, the four-wavelength approach of the optoelectronic microprobe also utilizes this MCLUT-based inverse model to assess tissue scattering and absorption parameters.

Figure 21:
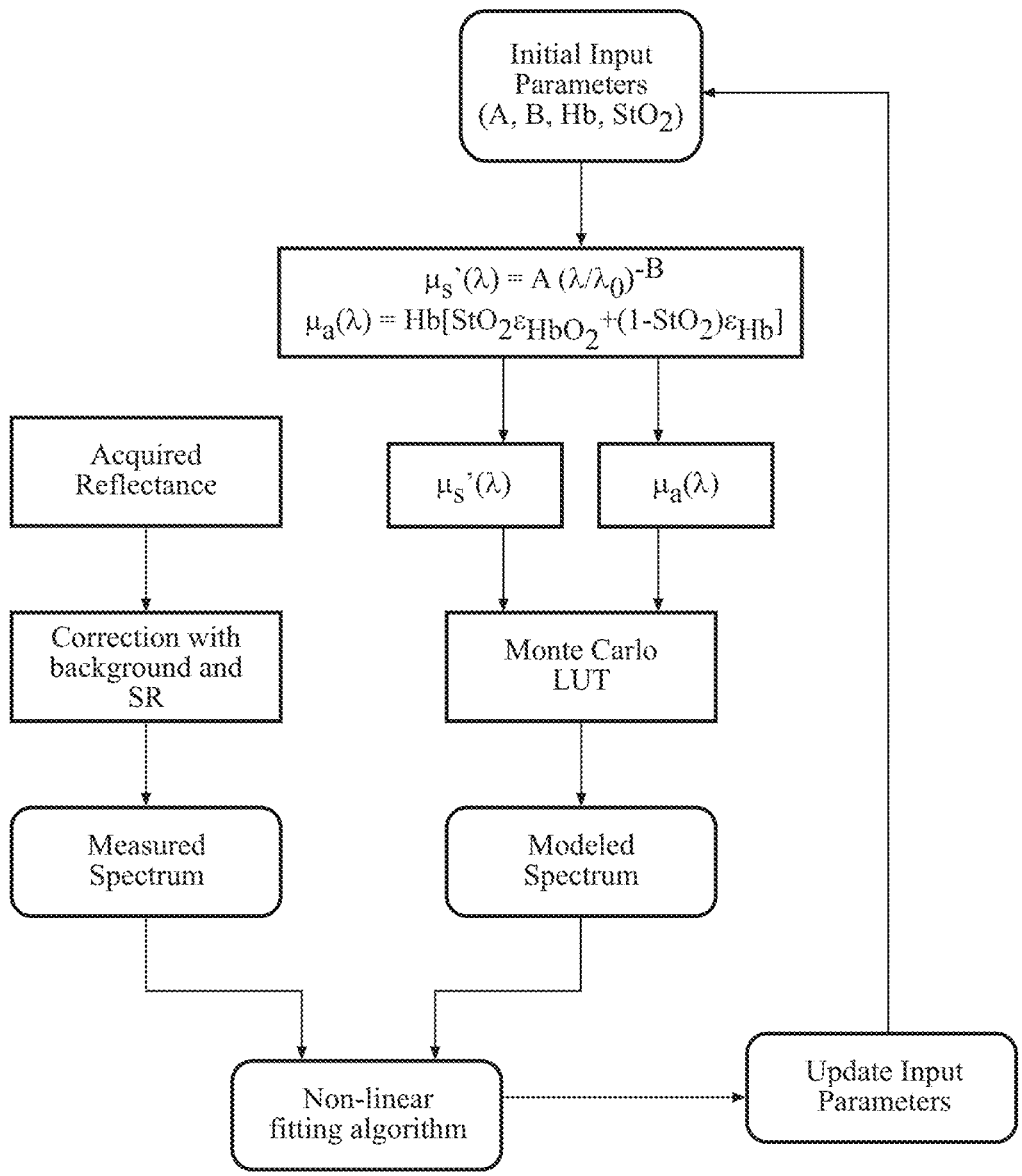
FIG. 21 is a flow diagram illustrating an optical data analysis algorithm.

Customized data analysis is based on an MCLUT inverse model approach. Monte Carlo simulations incorporating the optoelectronic microprobe geometry produces diffuse reflectance intensities for all combinations of physically realistic absorption (0-50 cm$^{-1}$) and scattering coefficients (0-50 cm$^{-1}$). Monte Carlo in a parallel implementation working on a general-purpose graphic processing unit may be used to decrease time to create the look-up-table. The process or algorithm to estimate the biophysical parameters including the parameter related to scatter density A and a scattering power parameter related to the scatter size B, the total hemoglobin concentration and oxygen saturation is shown in FIG. 21. In this process, the input parameters A, B, hemoglobin concentration, and oxygen saturation are used to calculate wavelength-dependent scattering and absorption coefficients. These coefficients are inputs to a MCLUT producing a modeled diffuse reflectance spectrum. The modeled spectrum then fits the measured corrected spectrum. Iterations with non-linear fitting algorithms are used to find optimal parameters yielding the best fit.

EXAMPLES

LED Characterization $I_f$-$V_f$ curves for the light sources (LEDs) of a microprobe having two LEDs (red and blue) may be obtained by adjusting the forward voltage by 0.1 V in a digital power supply (e.g., E3631A, Keysight Technology, Santa Clara, Calif.) and recording the corresponding forward current flowing through the LED. For the blue LEDs, three different sets of LEDs according to the eutectic bonding temperatures (e.g., 280, 290 and 300° C.) may be measured. For the red LEDs, to investigate the effect of the second eutectic bonding of the blue LEDs, two sets of the red LEDs may be measured before and after the eutectic bonding of the blue LEDs. Optical power of the emitted LED light is measured using an integrating sphere coupled with a photodetector (e.g., 3A-IS-V1, Ophir-Spiricon, North Logan, Utah) to account for diverging beam(s) of the both LEDs. The emission wavelength may be recorded by an optical spectrometer (such as a HR2000, Ocean Optics). To check the wavelength shift by different forward voltage, forward voltage may be varied for each LED.

Photodiode Characterization

The linearity between the detected optical power and photodiode (PD) output may be assessed by emitting blue and red LEDs, which may be characterized with $I_f$-optical power curves, towards the photodiode at a specific distance. The blue LED located 45 mm away from the photodiode and drove with the forward voltage varying from 2.9 V to 3.5 in 0.1 V step. The output voltage at the trans-impedance amplifier coupled with PGA may be read by an oscilloscope (such as a TDS220, Tektronics, Beaverton, Oreg.). The resistance determining the gain in the trans-impedance amplifier may be about 100 K to provide a gain of $10^5$, and the gain of the PGA may be set to 100 for a total gain of $10^7$. The distances between photodiode and LEDs may be determined to make the output voltage swing from 0 to 5V, which is a supply voltage of the trans-impedance amplifier and the programmable-gain amplifier (PGA). The red LED may be located 60 mm away from the photodiode because the relative sensitivity of the photodiode in 630 nm is higher than 460 nm. The same measurement may be performed with the red LEDs.

Reflectance Sensing of the Microprobe on Tissue Simulating Phantoms

Figure 22A:
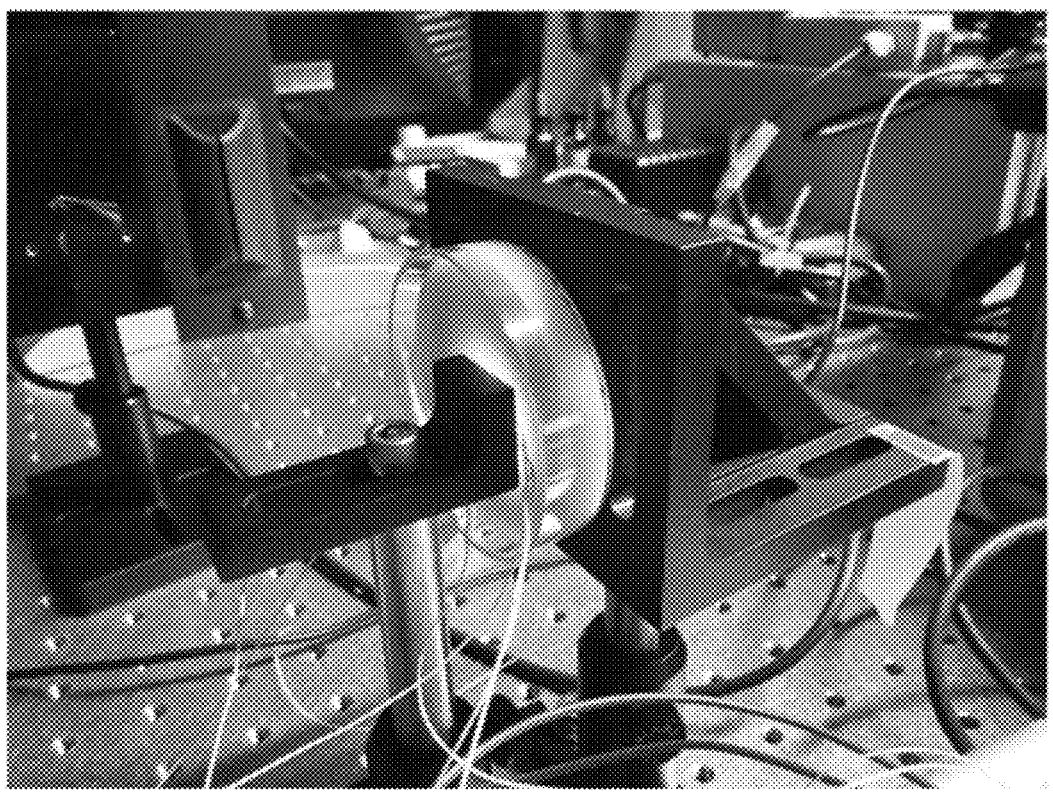
FIG. 22A is a photograph showing reflectance sensing on tissue simulating phantoms at 460 nm.
Figure 22B:
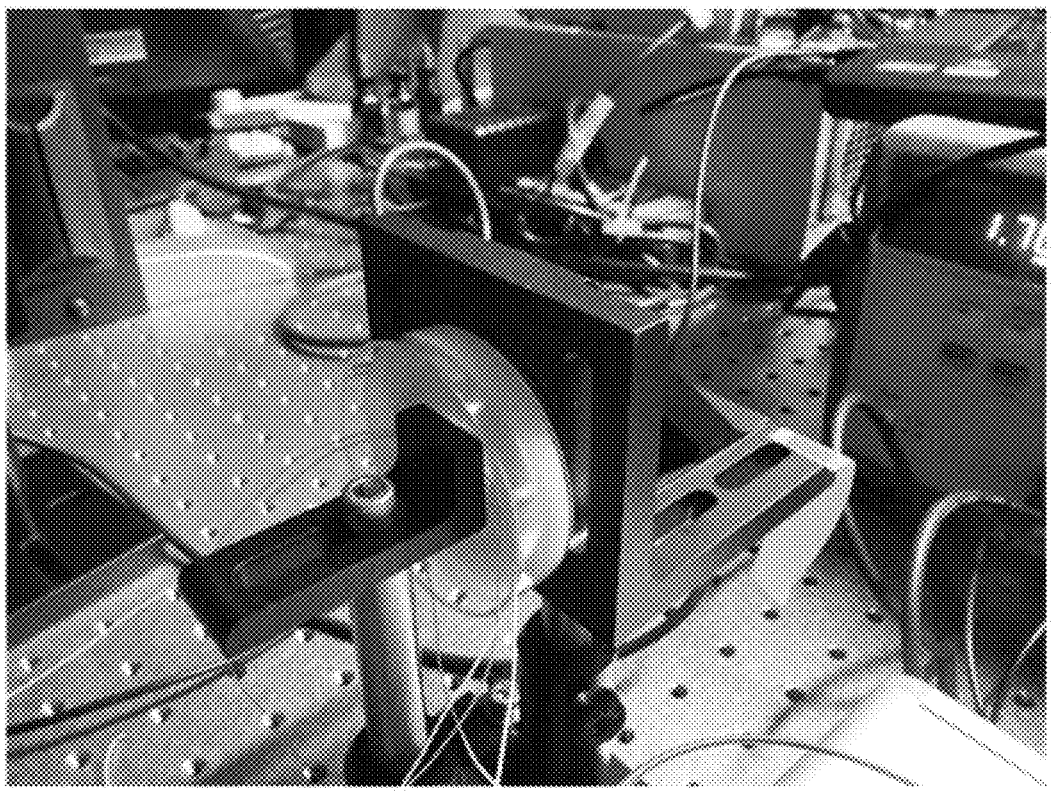
FIG. 22B is a photograph showing reflectance sensing on tissue simulating phantoms at and (b) 650 nm.

With reference to FIGS. 22A-22B, the reflectance sensing capability of the developed microprobe is evaluated on optical phantoms simulating human tissue scattering. Solid phantoms are typically manufactured using Intralipid (IL, I141, Sigma Aldrich, St. Louis, Mo.) as a scatterer in an agar-based matrix. Phantoms are prepared in a petri dish with a diameter of 60 mm and a height of 15 mm. In the sensing procedure at each wavelength, the forward voltage of the LED and the gain of the PGA are adjusted to get a proper voltage variation without saturation. Prior to phantom reflectance sensing, TIA voltage is measured 1) without LED output for dark measurement and 2) at an open space with LED emission to check how much LED emission directly entered the photodiode. In phantom sensing, the prototype probe is contacted with a surface of the phantom and slightly pushed to ensure the contact of the LED and PD.

A set of optical phantoms with three different intralipid (IL) concentrations (0.4, 0.8 and 1.2 mL of IL in 20 mL of de-ionized water) are manufactured to investigate the relationship between scattering coefficient and detected reflectance at the given geometry and angular sensitivity of source and detector. The probe interrogated three spots on the phantoms and the measured voltages are subtracted by the direct detection voltages to account for scattered reflectance sensing.

Testing and Validation

Electrical Testing

Electrical testing of fabricated microprobes (having a photodiode and blue and red LEDs) typically focuses on ensuring 1) moisture proofing and 2) working performance of the phototransistor and microcontroller. The microprobe is immersed in a liquid tissue simulating phantom phosphate buffer saline for fifteen minutes. Electrical performance and consistent output, as well as temperature, is monitored for the experiment duration. A National Institute of Standards and Technology (NIST) standard lamp is aligned with the phototransistor. The measured signal on the microcontroller is analyzed as a baseline measurement, and measurement drift and any signal saturation is monitored.

Optical Testing

The optical performance of the fabricated microprobes can be tested by creating liquid phantoms with realistic tissue scattering and absorption properties. The first phantom includes optical scattering from a homogeneous solution of polystyrene microspheres in de-ionized water (9 or 12 μm diameter to approximate the diameter of normal and cancerous pancreatic cell nuclei, respectively). The second phantom introduces varying levels of hemoglobin (primary absorber in human tissues) to make the liquid scattering phantom a better approximate to human tissue. Signal to noise ratio (SNR) is calculated as the average current intensity of ten sequential collections from the working performance of the phototransistor and microcontroller divided by ten sequential collections of the dark current from a phantom containing de-ionized water.

A two-layered solid phantom is also created to verify the spatially-resolved optical mapping of the microprobe. The bottom layer is a solid agar mixture of 9 μm diameter polystyrene microspheres with hemoglobin and the top layer is a liquid mixture of 12 μm diameter microspheres with a different hemoglobin concentration than the top layer. Then, the optoelectronic microprobe is inserted such that one optical module is contained within the top and bottom layers. Two-layered phantom measurements are compared to measurements from homogeneous phantoms created from the optical properties of each layer.

Temperature Measurements

To assess heat generation by optoelectronic microprobe operation, temperature is typically measured in de-ionized water while the microprobe is emerged in de-ionized water. The LED(s) and phototransistor are powered on continuously and temperature around the microprobe is measured every one minute up to fifteen minutes. Then, the LED(s) and phototransistor are switched on and off with a certain frequency, and the temperature is monitored approximately every one minute. With different operating options, the LED pulse width and frequency is optimized to minimize the heat generation.

Sterilization, Mechanical Testing, and Clinical Simulation

Figure 23:
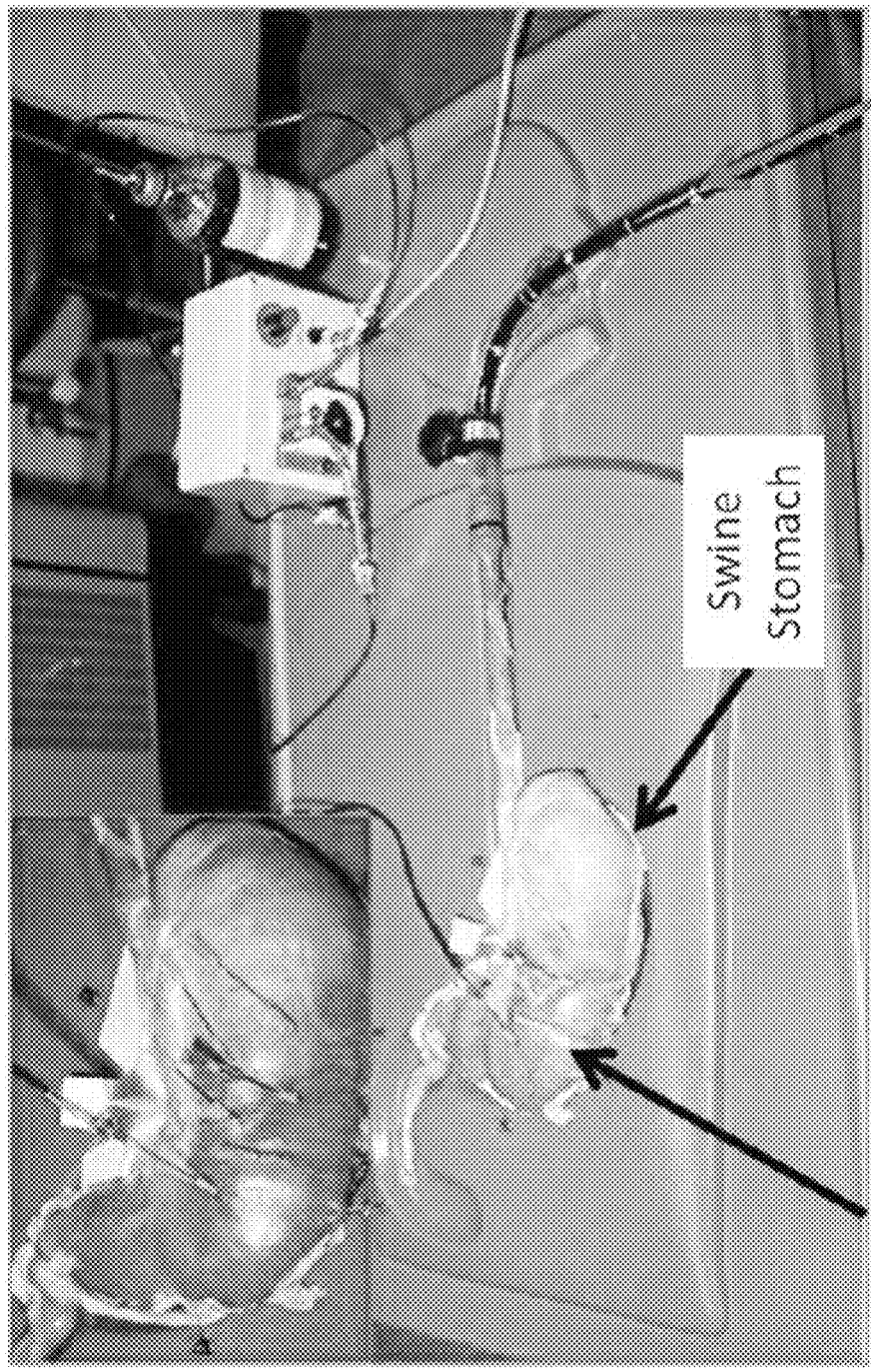
FIG. 23 is a photograph showing an Erlanger Active Simulator for Interventional Endoscopy (EASIE™) for use in testing a mechanical performance of the microprobe.

Each fabricated microprobe can be validated with a standardized procedure. Microprobes are sterilized with a standardized ethylene oxide protocol, which is typically employed in a hospital central sterile supply unit for medical instrumentation. This test employs an Erlangen Active Simulator for Interventional Endoscopy (EASIE™) (see FIG. 23), a clinical endoscopic training simulator, to validate the mechanical integrity and optical performance of each microprobe. The FNA hollow needle, containing the microprobe, is inserted through the instrument channel of the endoscope, protruded through the swine stomach, and into the pancreas-simulating phantom. The microprobe is removed from the endoscope and reinserted. Mechanical integrity of each microprobe is verified via microscopic visual examination and electronic testing.

Measurements on Freshly Excised Human Pancreatic Tissues

Using the IRB approved human studies protocols and experimental methods developed previously, freshly excised human pancreatic tissues can be measured with the optoelectronic microprobe to compare the performance of the microprobe with that of an optical-fiber-based system. Using a hollow needle, the microprobe is inserted into the tissue site of interest and optical measurements are made. Up to ten tissue sites are measured from each specimen. Needle insertion and number of sites measured are consistent with envisioned use during EUS procedures. Typically, five patients are enrolled in such a study during one year. Estimating 5-10 measured tissue sites per patient, 50-100 optical measurement sites are collected from the two optical sub-units. Each measurement has spatially co-localized histology samples.

Histology and Data Analysis

Optical measurements are compared to histopathologic analyses of a co-localized tissue biopsy obtained by a trained pathologist. Tissue biopsies are embedded in paraffin, cut into 5 μm thick slices, stained by H&E staining, and analyzed. For each pancreatic tissue type, data collected with the microprobe and with the optical-fiber-based system (existing data set) are compared at the two target wavelengths by forming the ratio $R_{470nm}/R_{630nm}$. A classification algorithm, based on multinomial logistic regression using Generalized Estimating Equations with one parameter (here, $R_{470nm}/R_{630nm}$) requires approximately 10 to 20 measured sites. The estimated 50-100 sites measured from five patients is typically sufficient to demonstrate feasibility of the microprobe for distinguishing normal tissues from adenocarcinoma tissues.

Fluorescence Sensing

By limiting the wavelength of detected light on the photodetectors, the optoelectronic microprobe can also enable fluorescence intensity sensing as well as reflectance measurements. An optical filter is used to cut off the excitation wavelength and to maintain a high transmission at the emission wavelength of the targeted fluorophore.

Fluorescence Lifetime Sensing

In an example, fluorescence lifetime sensing is also possible for the optoelectronic microprobe by incorporating signal processing and control electronics. Fluorescence lifetime sensing can be implemented in two configurations—frequency and time-domain. Further, small sized LEDs can be employed for pulsed and modulated excitation sources. Detection by photodetectors can also be modulated or gated with an external signal processing device. Specific embodiments for each technique are set forth below.

Frequency-Domain Lifetime Sensing

LED excitation may be modulated with 50 to 80 MHz and the fluorescence may be measured using a photodetector modulated at the same frequency. Phase shift between the excitation and the fluorescence may be used to calculate the fluorescence lifetime. Further, a lock-in-amplifier can be used to modulate the source and detector, and to detect the phase shift.

Time-Domain Lifetime Sensing

During a gated detection method, LEDs are excited by a pulse driver with the duration of a few nanoseconds. The exponential decay of fluorescence can be reconstructed using the number of gated detections with precisely controlled delay from the LED pulse initiation. Rapid lifetime determination algorithm can be employed for fast lifetime calculation.

Figure 24:
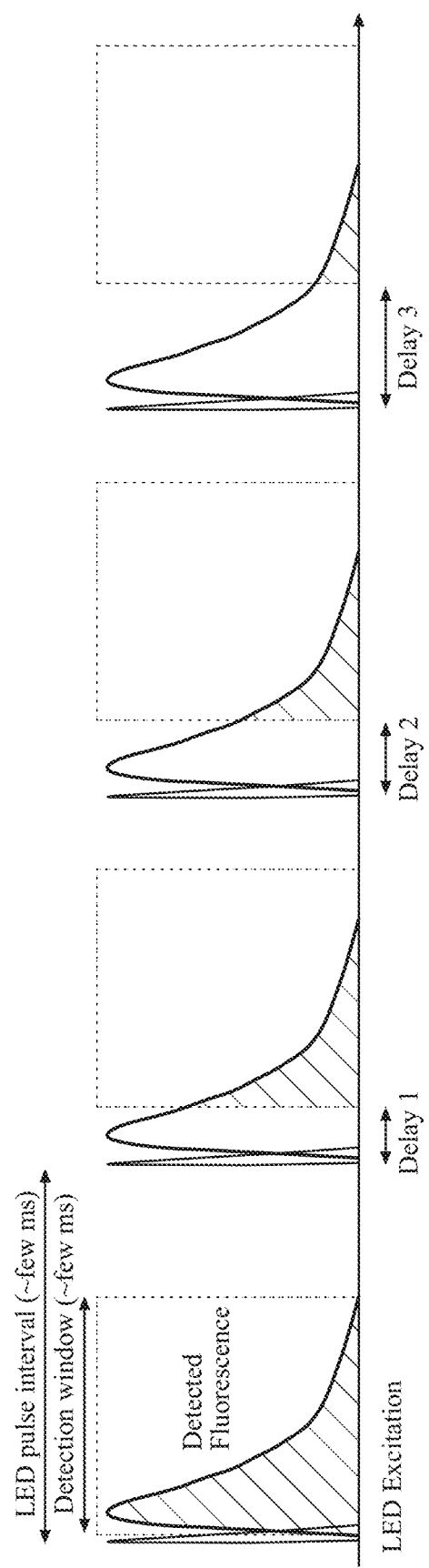
FIG. 24 is a graph illustrating a time-domain fluorescence sensing method without a short-period gating.

FIG. 24 is a graph illustrating a time-domain fluorescence sensing method without a short-period gating. An external delay generator determines the beginning of the detection window. For the first pulse excitation, there is no delay so the detector can measure all of the fluorescence. For the second pulse, fluorescence detection starts with delay and loses some fluorescence. The degree of reduced fluorescence intensity according to increasing delay is related to the fluorescence lifetime. As shown in FIG. 24, if a short period gating (less than 1 ns) is not technically feasible for the photodetectors used for the microprobe, as an alternative, multiple measurements within the delayed detection time window can be employed to reconstruct the fluorescence decay. Here, the time width is shorter than the laser pulse interval, which is possibly a few ms, instead of being less than 1 ns for gating methods. Direct recording of fluorescence decay may be accomplished using the photodetectors with a fast response synchronized by a short-pulsed LED excitation for samples having a strong fluorescence emission (e.g., exogenous fluorescence agents).

Feasibility Test for Fluorescence Sensing

Figure 25B:
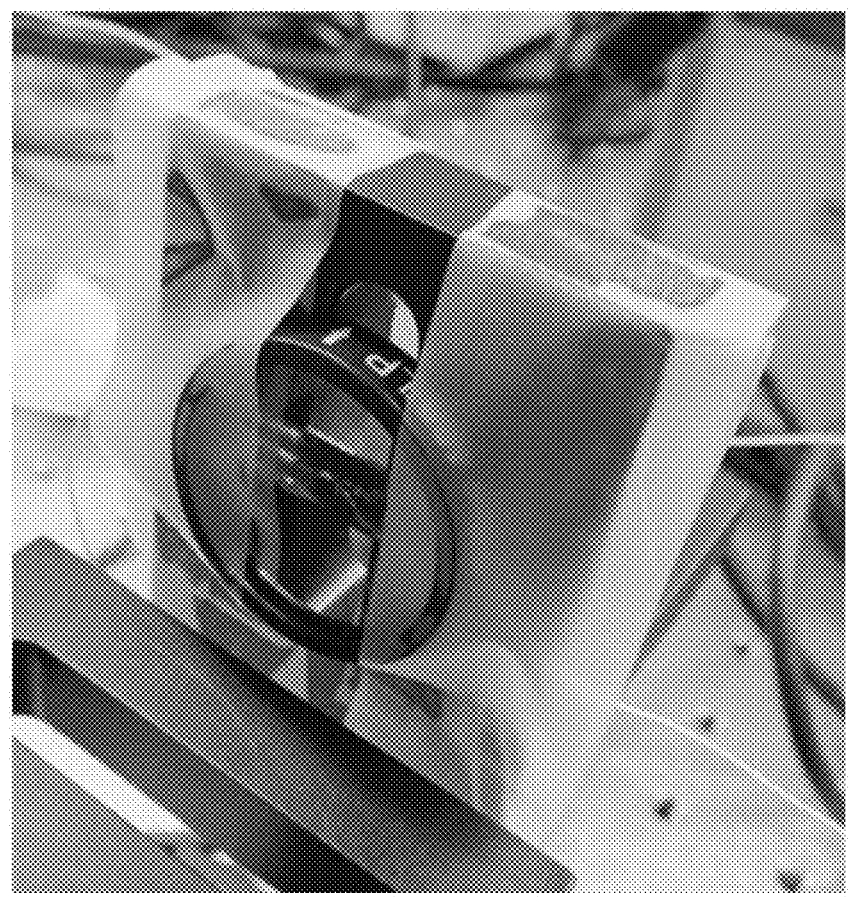
FIG. 25B is a photograph illustrating a fluorescence measurements setup with a long pass filter.

The feasibility of fluorescence sensing of the developed microprobe is assessed on a standard fluorescence solution. Since a small and thin long pass filter passing just fluorescence to the detector is not available, two microprobe modules are employed for 460 nm blue LED emission and photodiode detection, respectively (see FIG. 25A). The blue LED in one device excited 10 μM Rhodamine B in a cuvette with a 1 cm-pathlength, and an off-the-shelf long pass filter with 488 nm cutting wavelength (FF01-488/LP, Semrock, Rochester, N.Y.) (FIG. 25B) blocked 460 nm excitation light and passing just fluorescence emission (peak emission is around 580 nm) towards the PD in another device. The forward voltage of the LED increased and the corresponding voltages on the TIA are obtained.

Results

Blue LED

Figure 26A:
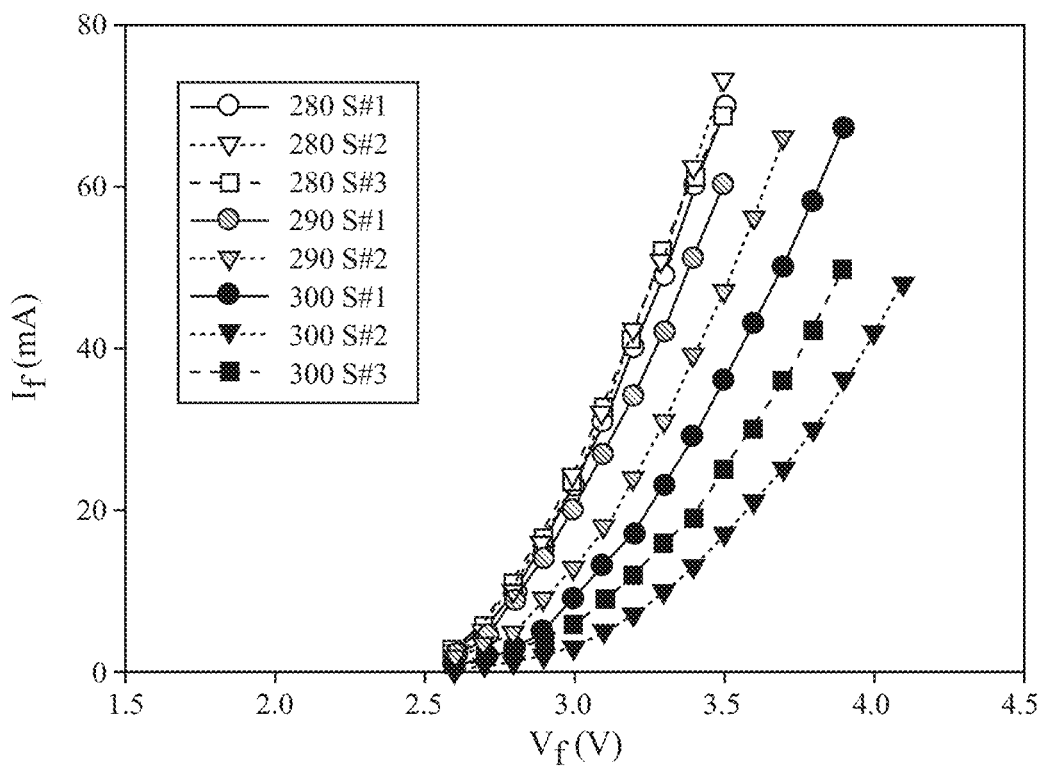
FIGS. 26A-26D are graphs showing $V_f$-$I_f$ curves of a bonded blue LED depending on different bonding temperatures (FIG. 26A), measured optical power versus the forward current on three different samples (FIG. 26B), emission spectrum depending on $V_f$ (FIG. 26C), and zoomed-in spectrum at the peak emission wavelength (FIG. 26D).
Figure 26B:
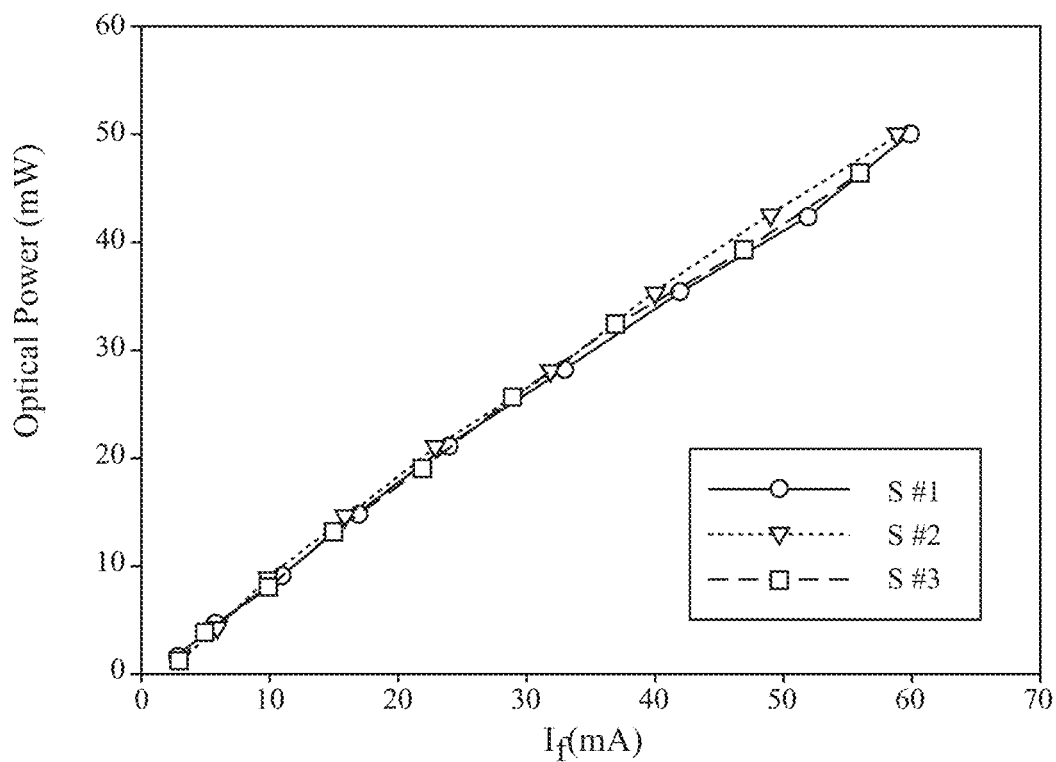
Figure 26C:
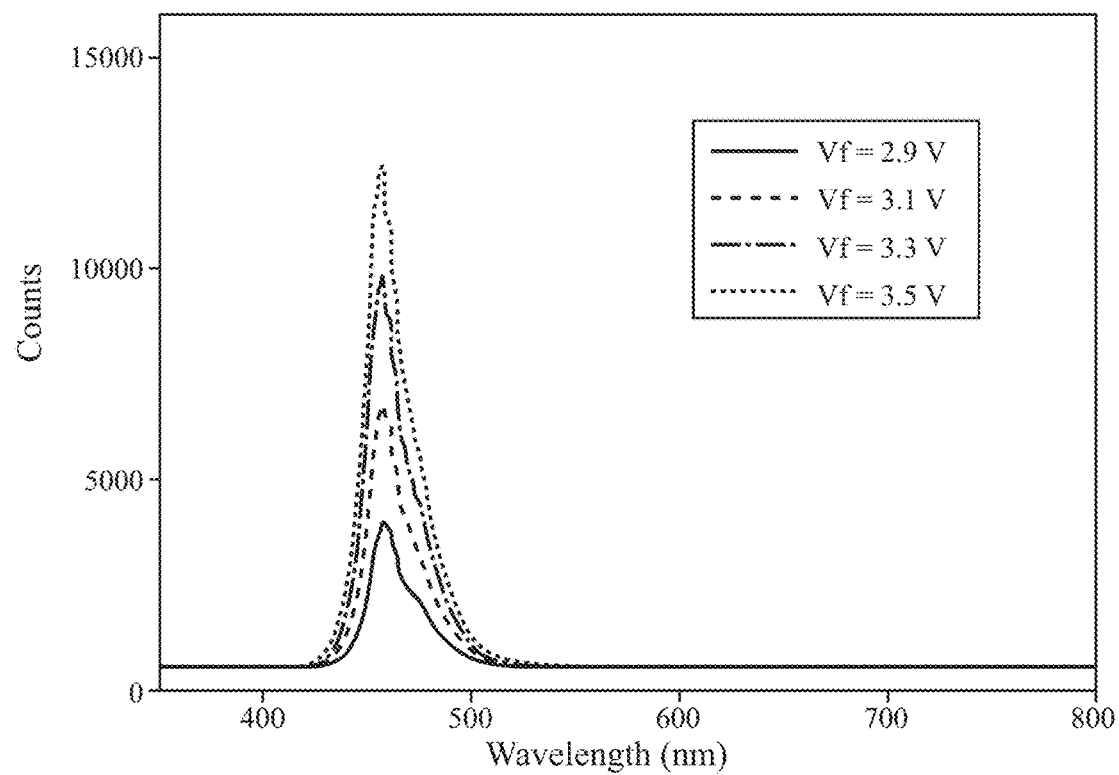
Figure 26D:
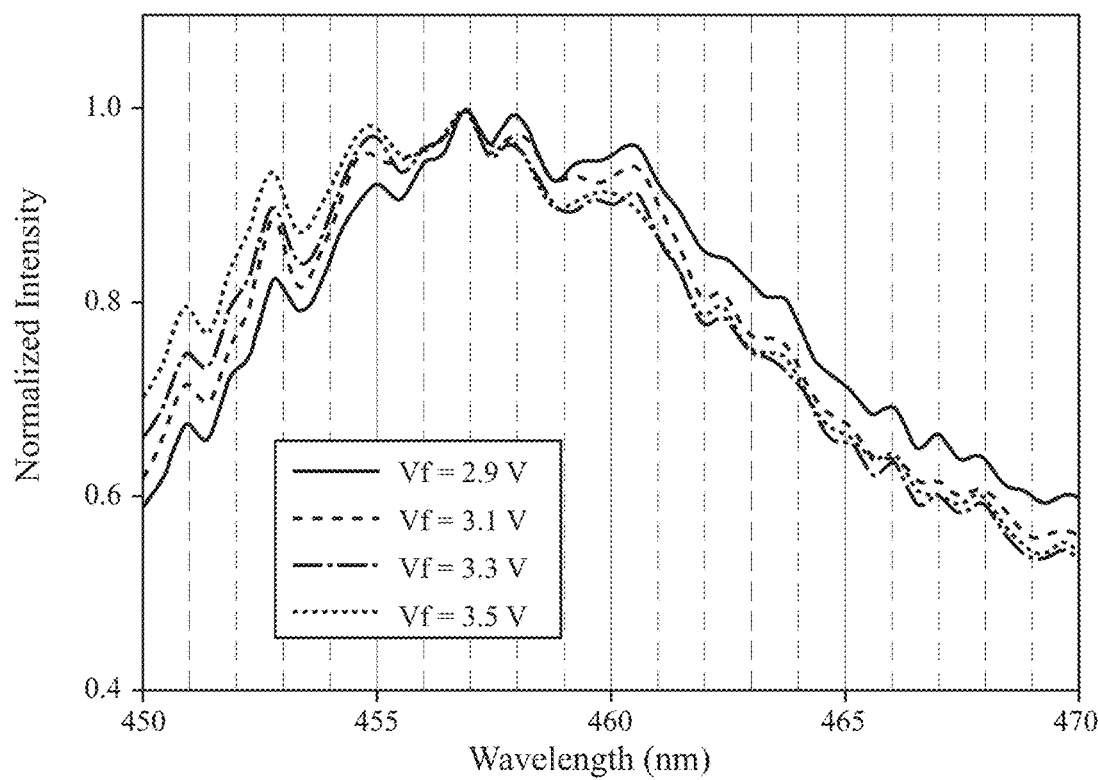
Figure 27A:
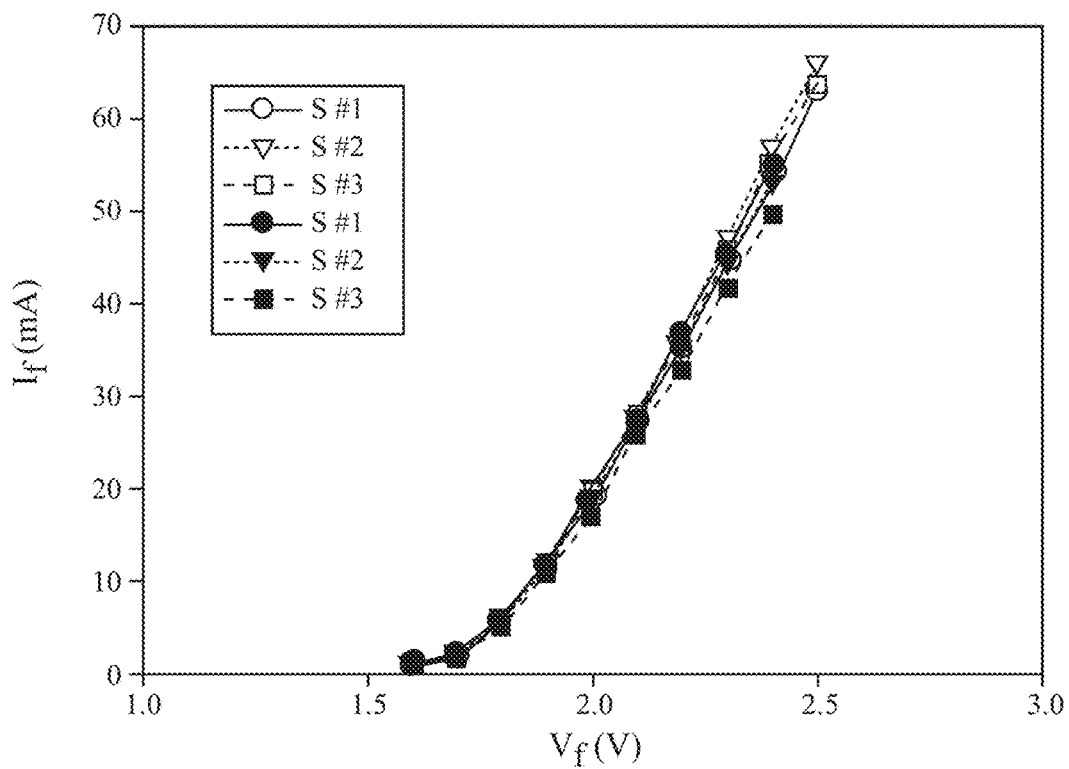
FIGS. 27A-27D are graphs showing $V_f$-$I_f$ curves of a bonded red LED before and after second eutectic bonding (FIG. 27A), measured optical power versus the forward current on three different samples (FIG. 27B), emission spectrum depending on $V_f$ (FIG. 27C), and zoomed-in spectrum at the peak emission wavelength (FIG. 27D).
Figure 27B:
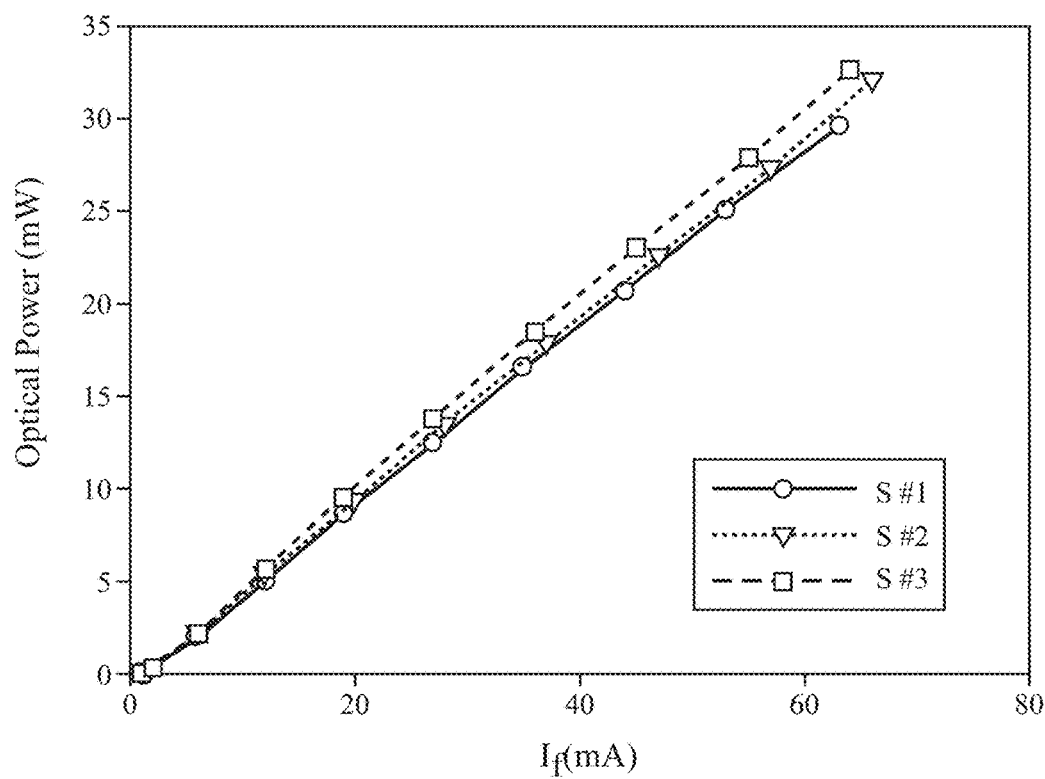
Figure 27C:
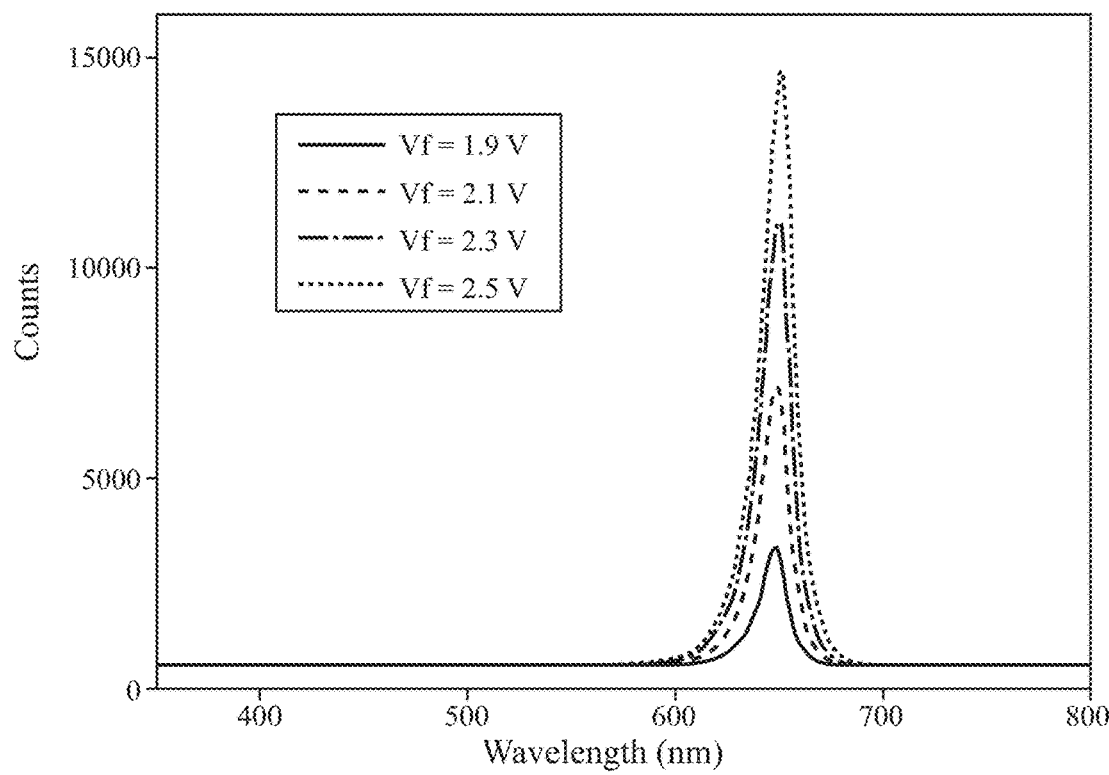
Figure 27D:
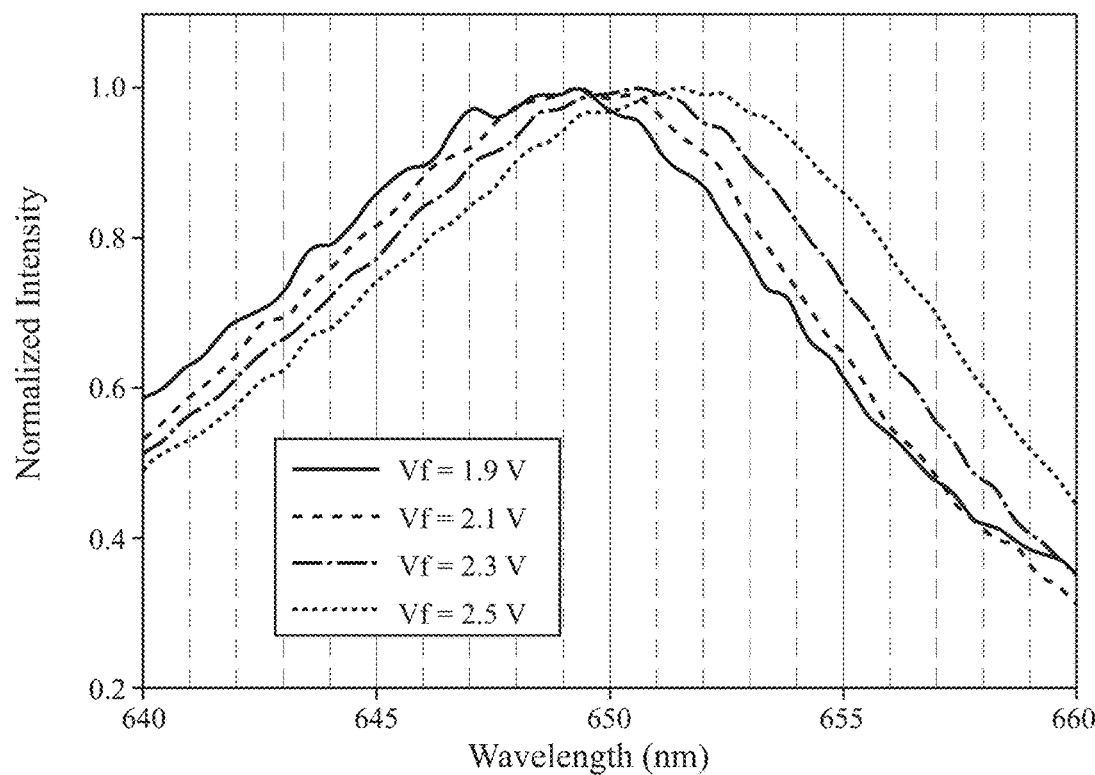

FIG. 26A shows $I_f$-$V_f$ characteristics of assembled blue LEDs depending on different temperature applied for the eutectic bonding. At a temperature higher than 280° C., $I_f$-$V_f$ performance is deteriorated and inconsistent. Measured $I_f$-Optical power curves show a good linear relationship and consistency between three samples (see FIG. 26B). Peak emission wavelength is 457 nm with a full-width-half-maximum of around 30 nm (see FIG. 26C). No prominent wavelength shift depending on the forward voltage is observed (see FIG. 26D).

Red LED

The bonded red LEDs after the eutectic bonding of blue LEDs shows the same performance as the LEDs before the bonding (see FIGS. 27A-27D). This indicates the second eutectic bonding does not affect the results of the first eutectic bonding. Measured optical power is proportional to the applied forward voltage with the consistency between three samples. At the regular forward current of 50 mA, optical power is 22.5 mW. Measured peak emission wavelength is around 650 nm with a full-width half-maximum (FWHM) of 20 nm. Wavelength is shifted at 1/15 nm/mA rate.

Photodiode

Figure 28A:
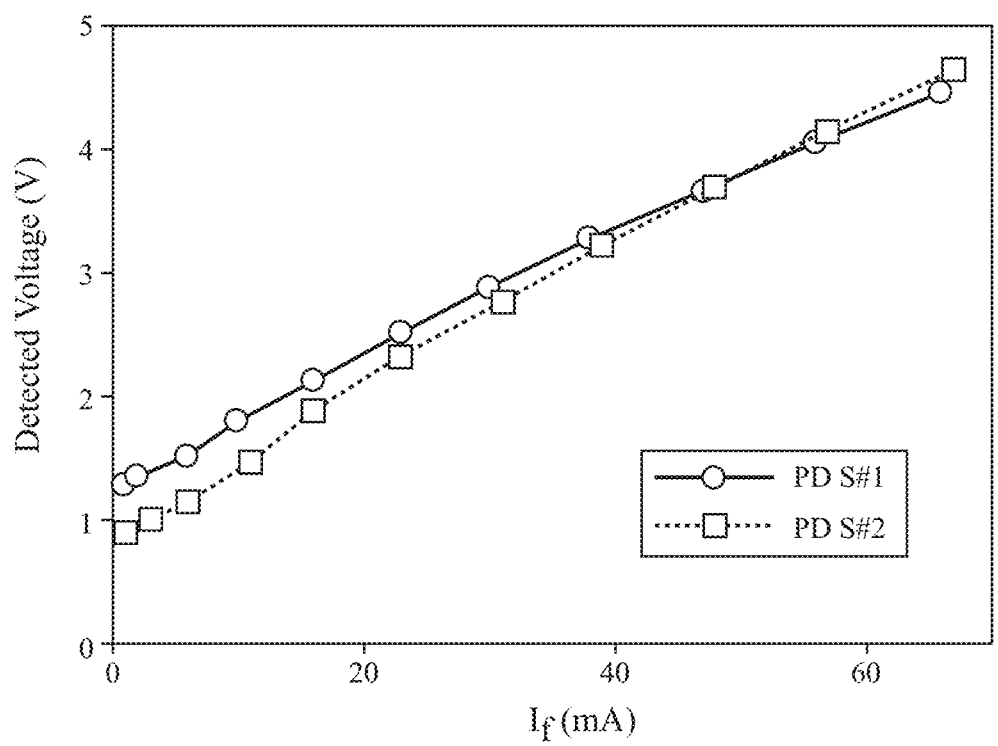
FIGS. 28A-28B are graphs of the voltages at a trans-impedance amplifier output according to different forward currents on blue LEDs (FIG. 28A) and red LEDs (FIG. 28B).
Figure 28B:
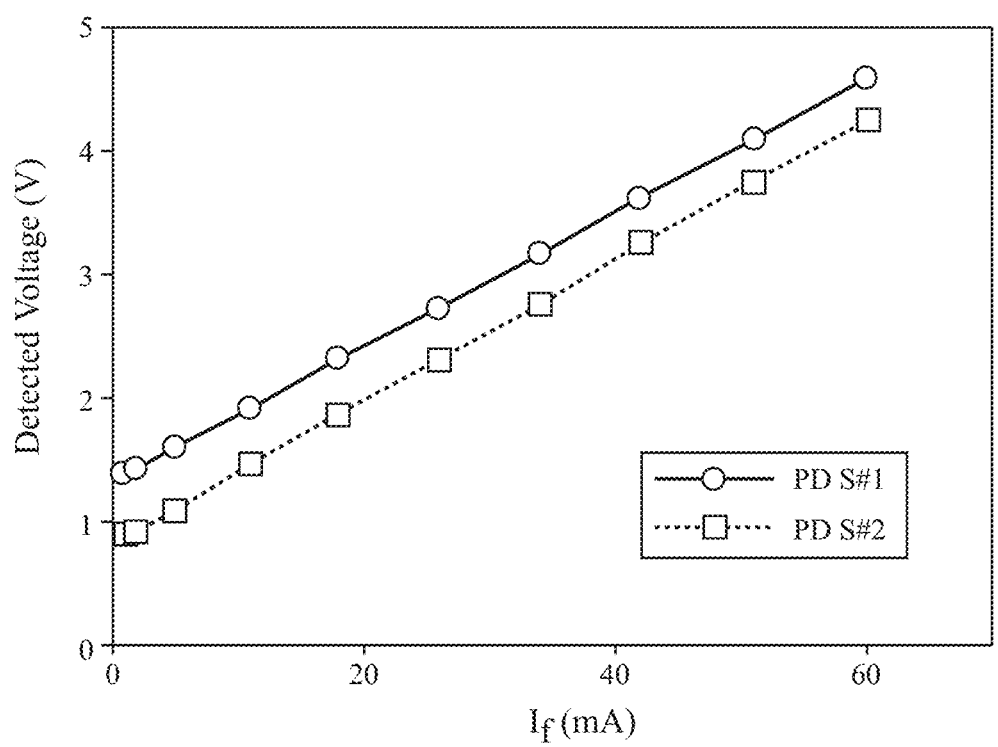

FIG. 28A-28B displays a linear relationship between the forward current of the source (optical power detected on the PD) and detection voltage (current flowing in the PD) at the transimpedance amplifier (TIA) output in two PDs at both wavelengths. Given the total gain is 107, the dark current of the PD can be calculated as ~1V/$10^7$ (A/V)=0.1 µA. While two PDs show the consistent performance, as indicated by the same slope with different dark voltages, the PD of sample S #2 shows a higher slope in a different wavelength.

Characterization of Reflectance Sensing on Tissue Simulating Phantoms

For reflectance sensing, the total gain of the trans-impedance amplifier is set to $10^5$. The forward currents are 2 mA and 6 mA for red and blue LEDs, respectively, to avoid saturation in trans-impedance amplifier output voltage by the direct detection of the emission light. With a gain of $10^5$, the dark voltage is 0.1 mV. The voltages measured by the direct detection are 0.23 mV in 460 nm and 0.39 mV in 650 nm, respectively. Detection voltage increased on higher concentrations of the intralipid, indicating the reflectance sensing is feasible. A larger error bar in 460 nm sensing probably indicates that 460 nm sensing could be more sensitive than 650 nm sensing setup.

Fluorescence Feasibility Test

Figure 29A:
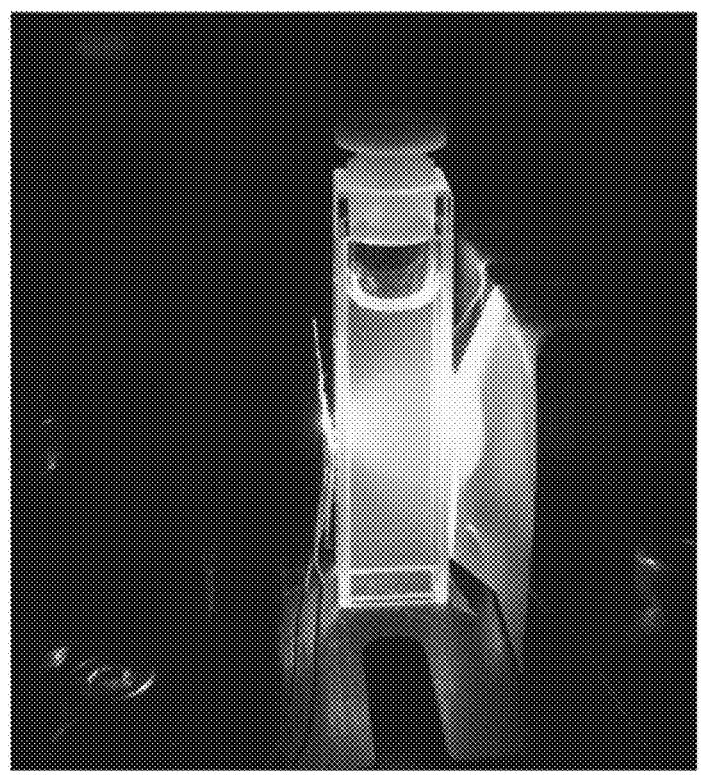
FIG. 29A is a photograph showing a rhodamine B fluorescence emission excited by a blue LED.
Figure 29B:
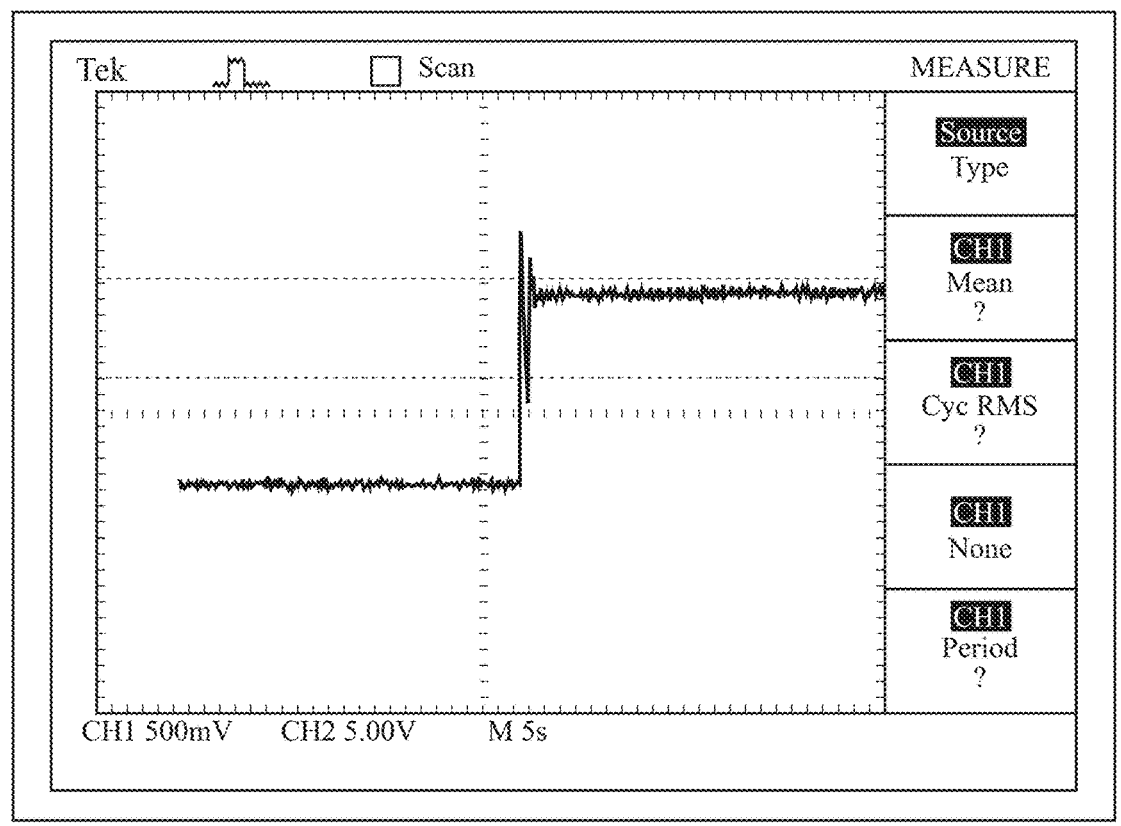
FIG. 29B is an oscilloscope screenshot showing the voltage at the trans-impedance amplifier output increasing when a cuvette containing 10 µM of rhodamine B solution is placed between the blue LED and the photodiode.
Figure 29C:
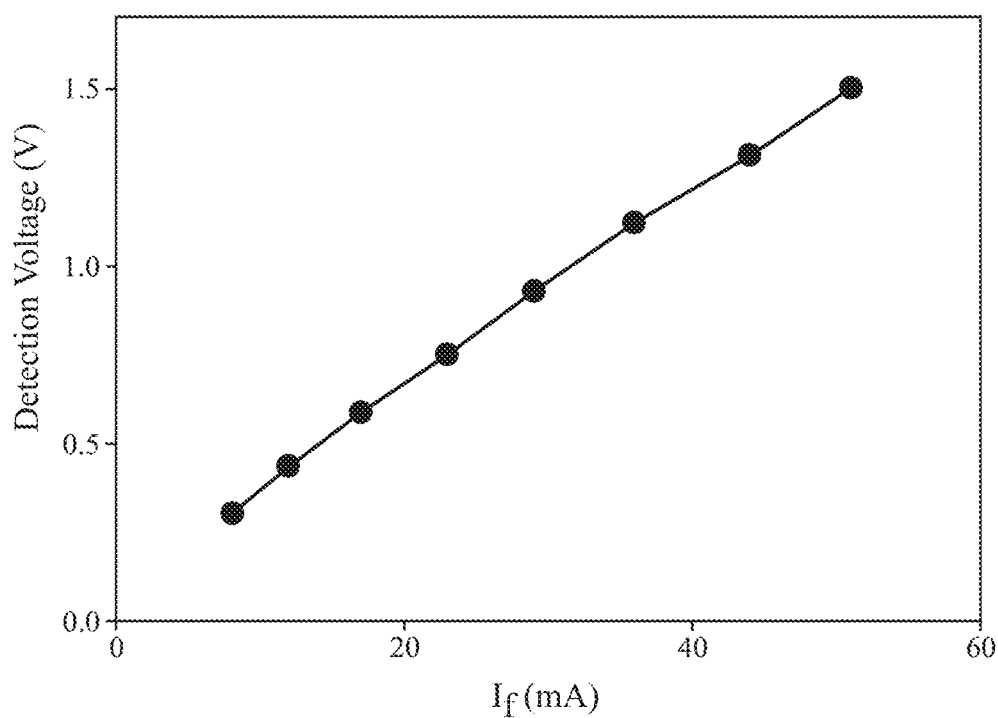
FIG. 29C is a graph showing detection voltages corresponding to different forward currents on the blue LED, and that fluorescence emission increases linearly to the excitation intensity.

With a total gain of 5×$10^6$ and a forward current of 40 mA on the blue LED, the photodiode detection voltage is 0.10 V without a fluorescence sample, and close to the dark voltage of 0.09 V ensuring the block of 460 nm emission light by the 488 nm LP filter. When the sample is placed in the excitation and detection path, the fluorescence detection voltage is up to 1.31 V (as shown in FIG. 29A-29B). Fluorescence detection voltage increases as the excitation power increases (shown in FIG. 29C).

Signal-to-Noise Ratio Calculation

Signal-to-noise (SNR) ratio has been assessed by acquiring 20 reflectance measurements on a 99% reflectance standard for both wavelengths. SNR is calculated by: SNR=20 log (average of 20 measurement/standard deviation of 20 measurements). The resulting SNR for both wavelengths ranged from 50 to 60 dB.

Waterproofness Test

Figure 30C:
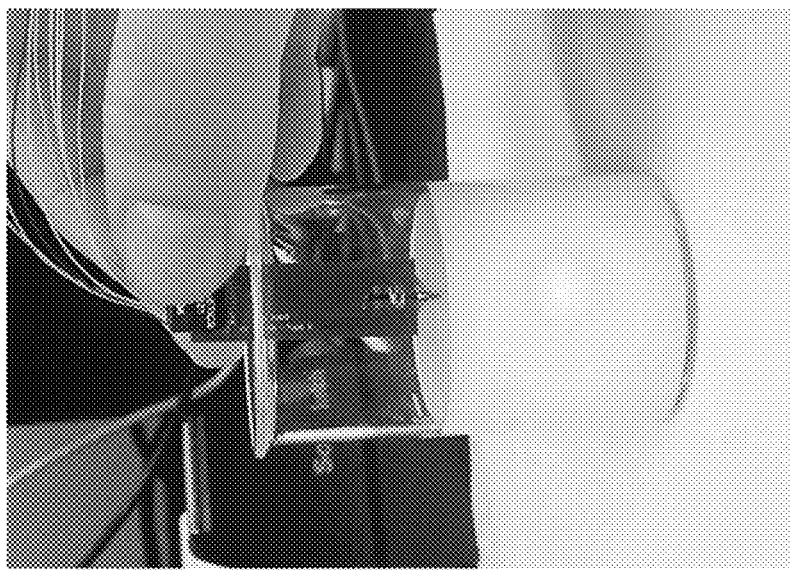
FIGS. 30A-30C are photographs showing a submerged microprobe in deionized (DI) water emitting blue light (FIG. 30A) and scattered LED light distribution in turbid media (FIGS. 30B and 30C).
Figure 30B:
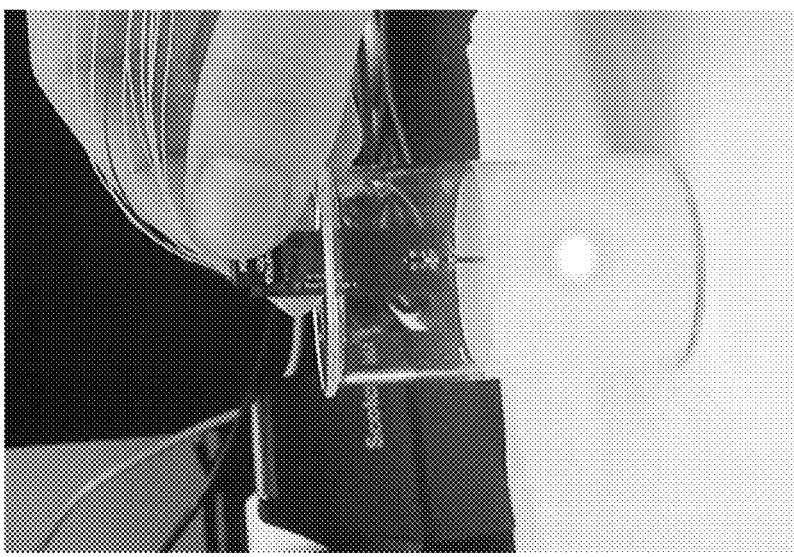
Figure 30A:
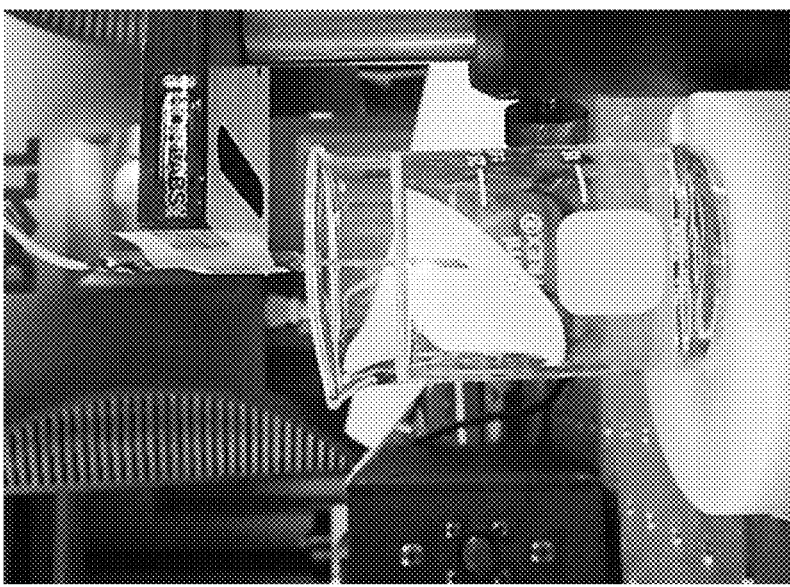

To demonstrate waterproofness of epoxy encapsulation, the microprobe is submerged into a deionized water for about 15 minutes (shown in FIGS. 30A-30C), an estimated time required for in vivo evaluation in a clinic. No degradation in optical performance, including the LED emission power and detected reflectance intensity, is found. The result reveals the developed microprobe would not be affected by watery environment of in vivo tissue sensing.

The optical sensing performance of the entire system is verified on tissue-simulating phantoms in comparison with the optical spectroscopy system (RFLS, Reflectance and Fluorescence Lifetime Spectrometer).

A set of solid tissue phantoms is created based on an agarose powder in dionized water with a polystyrene microsphere (scatterer) and a different concentration of hemoglobin (absorber) dissolved. This is shown FIG. 31. The determined concentration of the microsphere mimics the scattering coefficient of human pancreatic tissues. The variation of hemoglobin concentrations is in a range of the absorption coefficients of human pancreatic tissues, and simulates the different reflectance ratio $R_{460nm}/R_{650nm}$.

Figure 31:
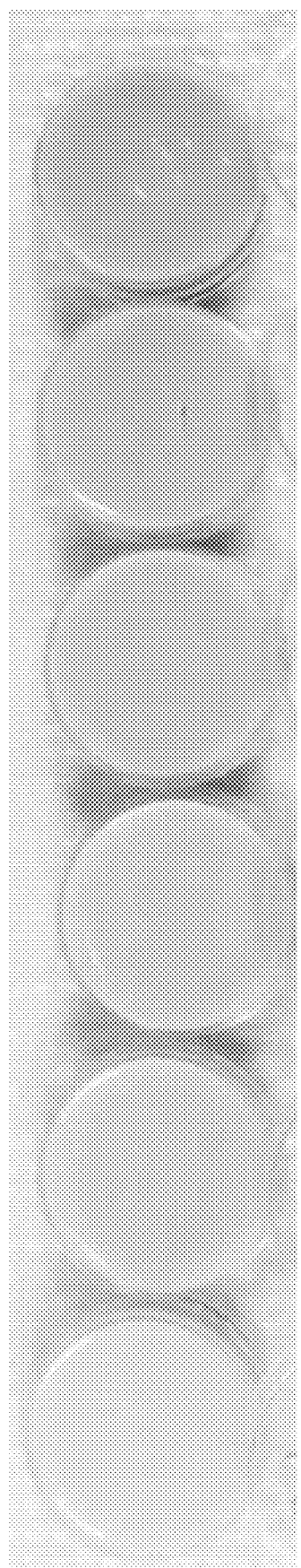
FIG. 31 is a photograph showing solid tissue phantoms made with a base of agarose gel in deionized water, a 1 µm diameter polystyrene microsphere is added with a ratio of 1:5 (microsphere:deionized water), and 0.465 mg/mL of hemoglobin is added to make 5 µM to 30 µM (left to right) by a step size of 5 µM.

As shown in FIG. 31, solid tissue phantoms are made with a base of agarose gel in dionized water. A 1 µm-diameter polystyrene microsphere is added with a ratio of 1:5 (microsphere:DI water). 0.645 mg/ml of hemoglobin is also added to make 5 µM to 30 µM (left to right) by a step size of 5 µM.

Prior to phantom measurements, the microprobe is calibrated on a 50% reflectance standard and initial measurements in open air is acquired to account for direct entrance of emission light to detector. This process is repeated for each LED emission wavelength. Relative reflectance is calculated by Equation 1:

$$R = \frac{R_{meas}(\text{Phantom}) - R_{meas}(\text{Open})}{R_{meas}(50\% \ Ref) - R_{meas}(\text{Open})} \times 0.5 \quad \text{(Equation 1)}$$

For each phantom, three sites are measured and averaged.

RFLS is also calibrated with the 50% reflectance standard before measurements. The fiber optic probe (a core diameter of 600 µm with 0.22 NA, 660 µm distance between a source and a detection fiber) is placed on the phantoms.

Figure 32A:
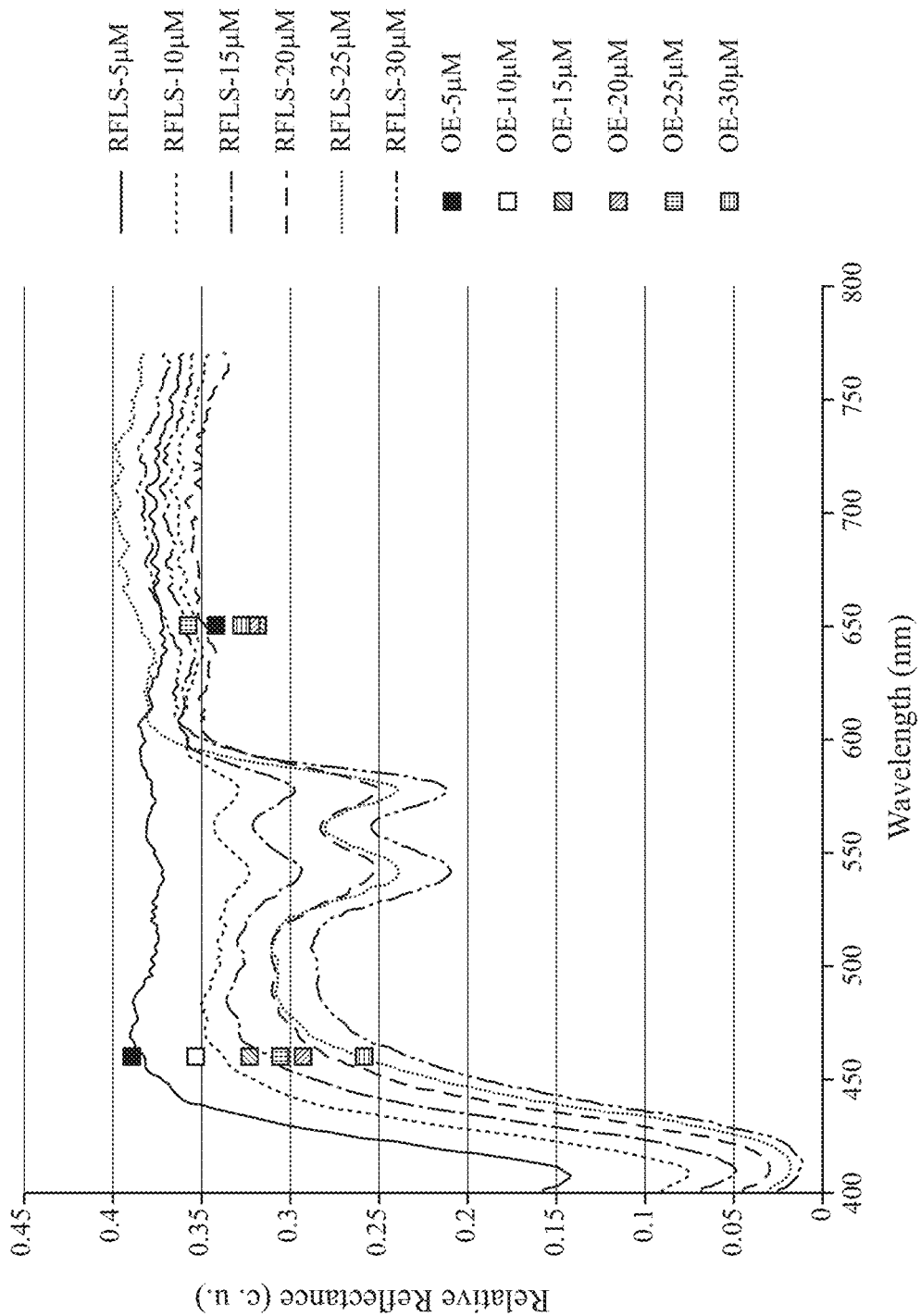
FIG. 32A is a graph showing a measured relative reflectance using a prototyped optoelectronic microprobe and the Reflectance and Fluorescence Lifetime Spectrometer (RFLS), where the solid lines represent wavelength-resolved reflectance spectra measured by the RFLS on the six phantoms shown in FIG. 31. From qualitative comparison with reflectance spectra obtained from excised human pancreatic tissues, the manufactured tissue phantoms shown are properly designed to mimic optical properties of human pancreatic tissue. Dots at wavelength of 460 nm and 650 nm indicate the microprobe readings of six phantoms. The microprobe readings are matched with the RFLS spectrum at those wavelengths for all six phantoms.
Figure 32B:
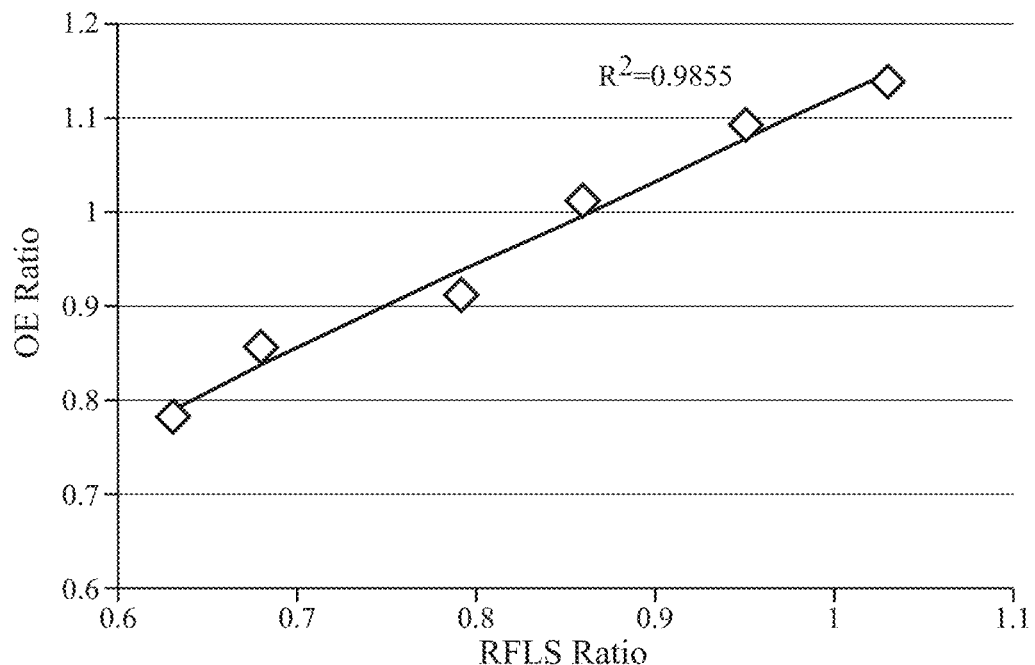
FIGS. 32B and 32C are graphs showing that the proposed ratio metric from both devices has a consistently decreasing trend as the hemoglobin concentration increases (FIG. 32B) where the ratios from the microprobe are lower than the one from the RFLS for all six phantoms, which could be attributed to different source-detection geometry (including angular sensitivity of PD and emission pattern of LED) even with the same separation (FIG. 32C).
Figure 32C:
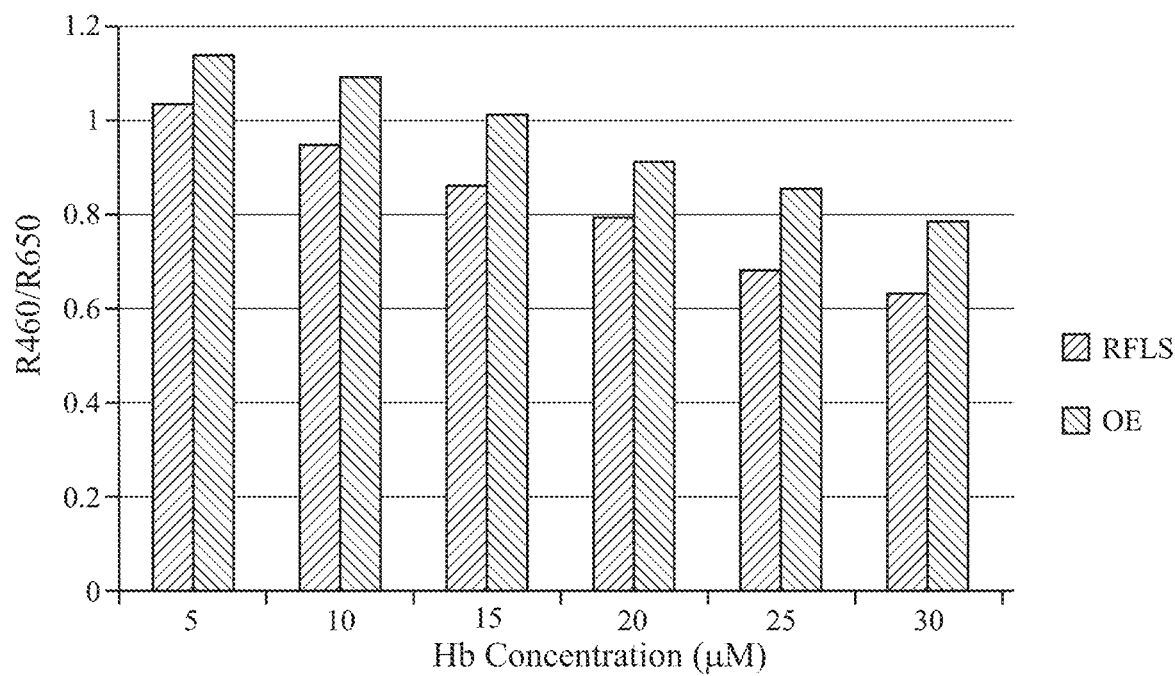

FIGS. 32A-32C show the measurement results using the microprobe and the RFLS on 6 different phantoms. From different reflectance spectral shapes obtained by the RFLS, more hemoglobin concentration produced lower $R_{460nm}/R_{650nm}$. At both wavelength of 460 nm and 650 nm, the relative reflectance intensities measured with the microprobe show a good agreement with reflectance spectra acquired by the RFLS (FIG. 32A). The absolute ratios by the microprobe are consistently lower for all phantoms than the ratios by the RFLS (FIG. 32B). This difference would be attributed to different source-detector geometry. However, there is a linear correlation between two ratios (FIG. 32C), which demonstrates that the optical performance of the microprobe is comparable to the RLFS in term of obtaining the reflectance ratio.

Dual Unit Fabrication

Figure 33:
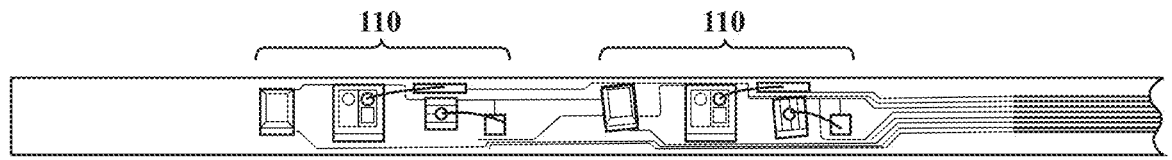
FIG. 33 illustrates an assembled microprobe containing a dual sensing unit for simultaneous multi-site sensing, with a center-to-center spacing between each sensing unit of about 1 mm, ensuring no cross-talk during the sensing.

To demonstrate the multiple-sites sensing capability, the microprobe with a dual sensing unit has been designed, fabricated and assembled. FIG. 33 shows the potential of volumetric sensing to address the lack of spatial information in conventional point spectroscopy. With a traditional fiber-based approach, it may be challenging to achieve multiple-sites sensing.

Simulation of Optical Sensing Volume

Figure 34:
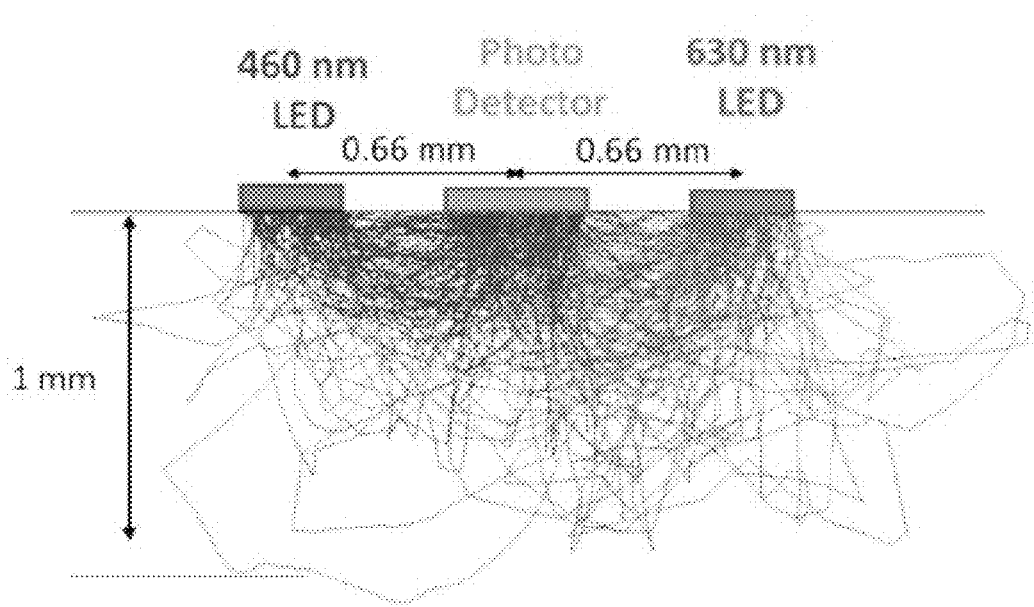
FIG. 34 illustrates a side view propagation of two wavelengths (blue and red) in a pancreatic tissue model.

A computational model is employed to visualize the detected photon paths for each wavelength given the designed source-detector geometry. The embedded Monte Carlo algorithm in the commercialized software (ZEMAX®) is used to simulate light propagation from the LED to the photodetector in pancreatic tissue model. The model reflects a realistic technical specification of each of the optoelectronic components that can affect simulation results, including dimension, angular emission distribution of each LED, and active area and angular sensitivity of photodiode. Optical interrogation volume by the designed microprobe can be qualitatively estimated using the simulation results. With reference to FIG. 34, the light with a longer wavelength (650 nm) travels into a deeper tissue area due to a longer mean path length determined by a lower absorption and scattering coefficient. The paths from each of the blue and red LEDs forms an optical interrogation volume of 1 mm$^3$, which is comparable to the volume of smeared tissue obtained during EUS-guided FNA.

Thermal Safety Analysis

Figure 35:
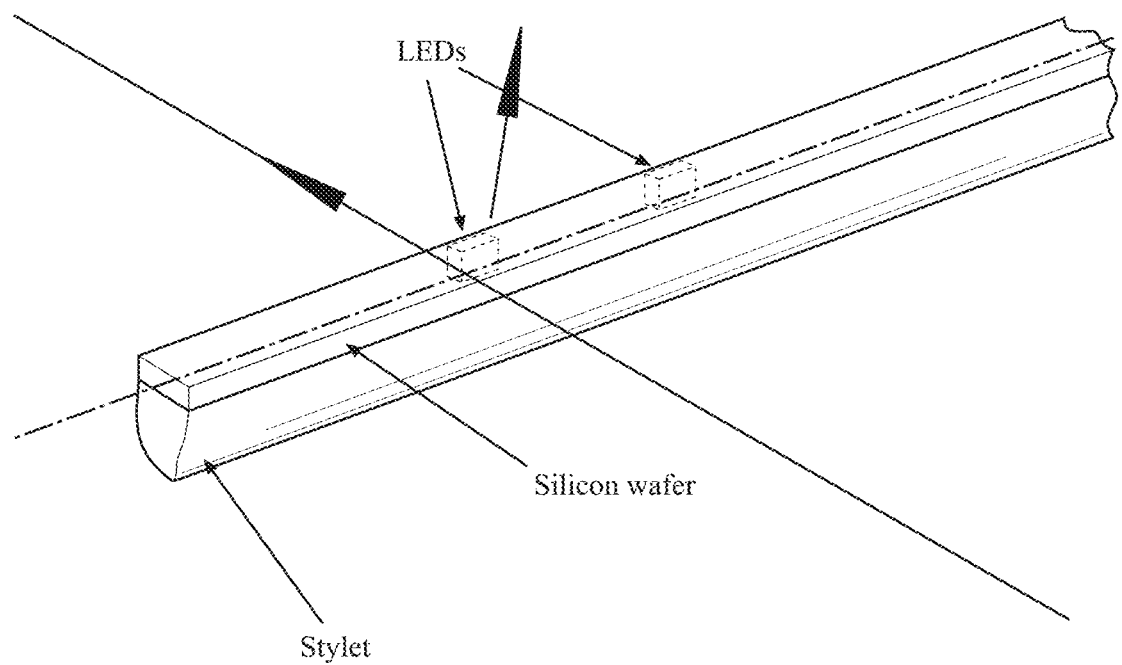
FIG. 35 illustrates a three-dimensional model of a microprobe including integrated sensors for heat transfer analysis.
Figure 36A:
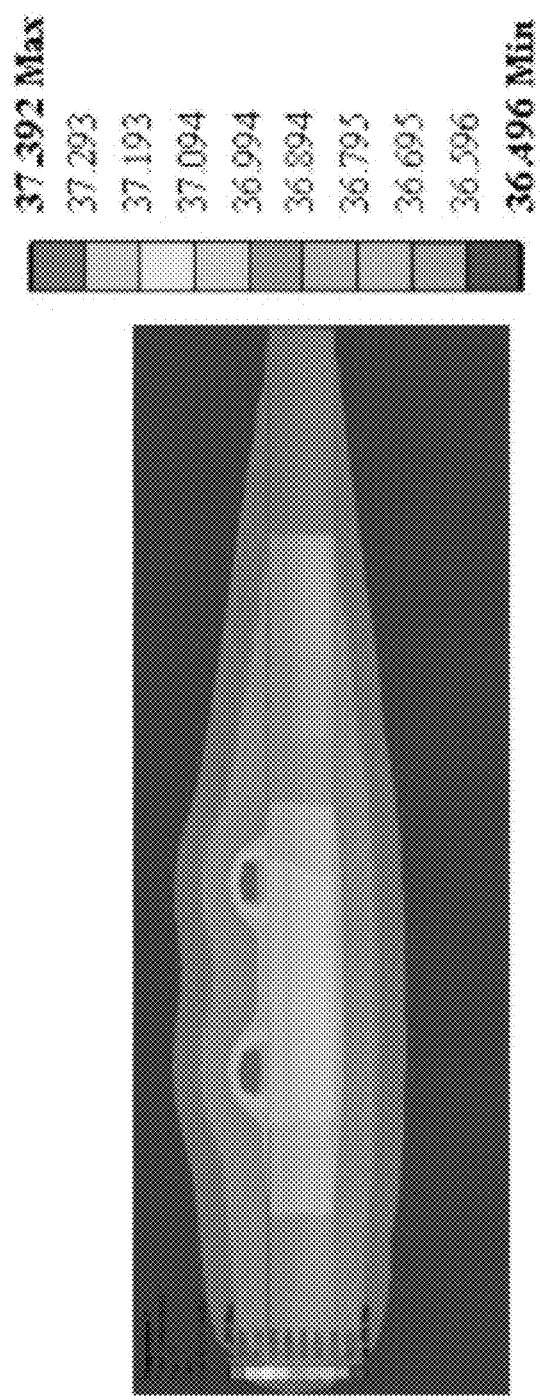
FIGS. 36A and 36B are graphs of a temperature distribution from a side-view of the model of the microprobe shown in FIG. 35 after about 1 second of LED illumination (FIG. 36A) and in steady-state after about 10 seconds of LED illumination (FIG. 36B).
Figure 36B:
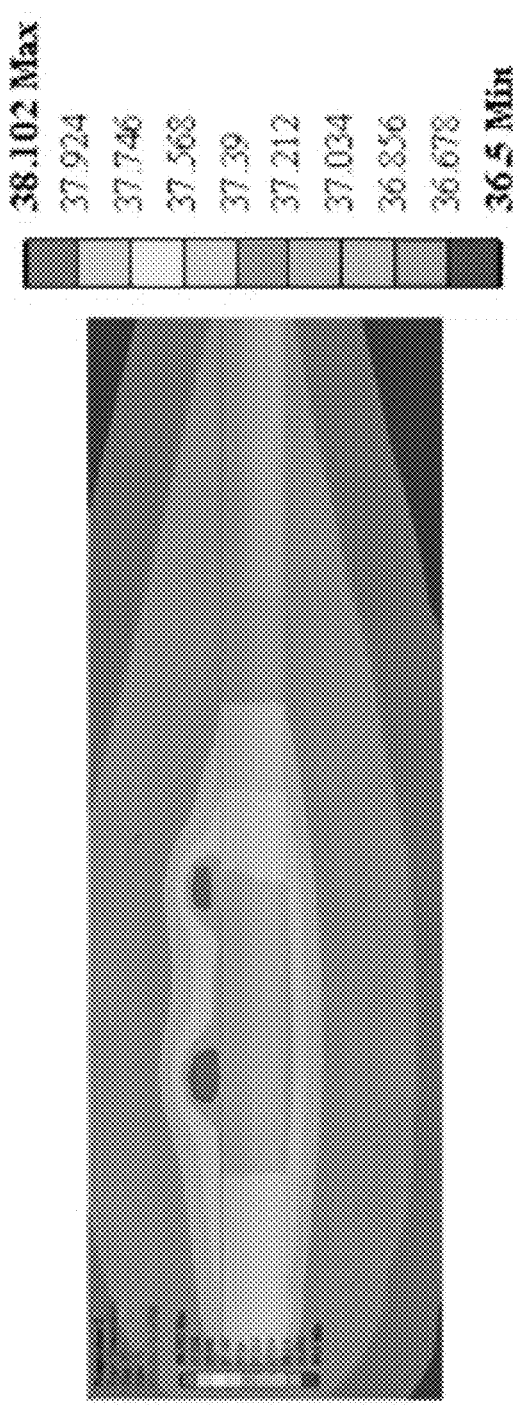
Figure 37:
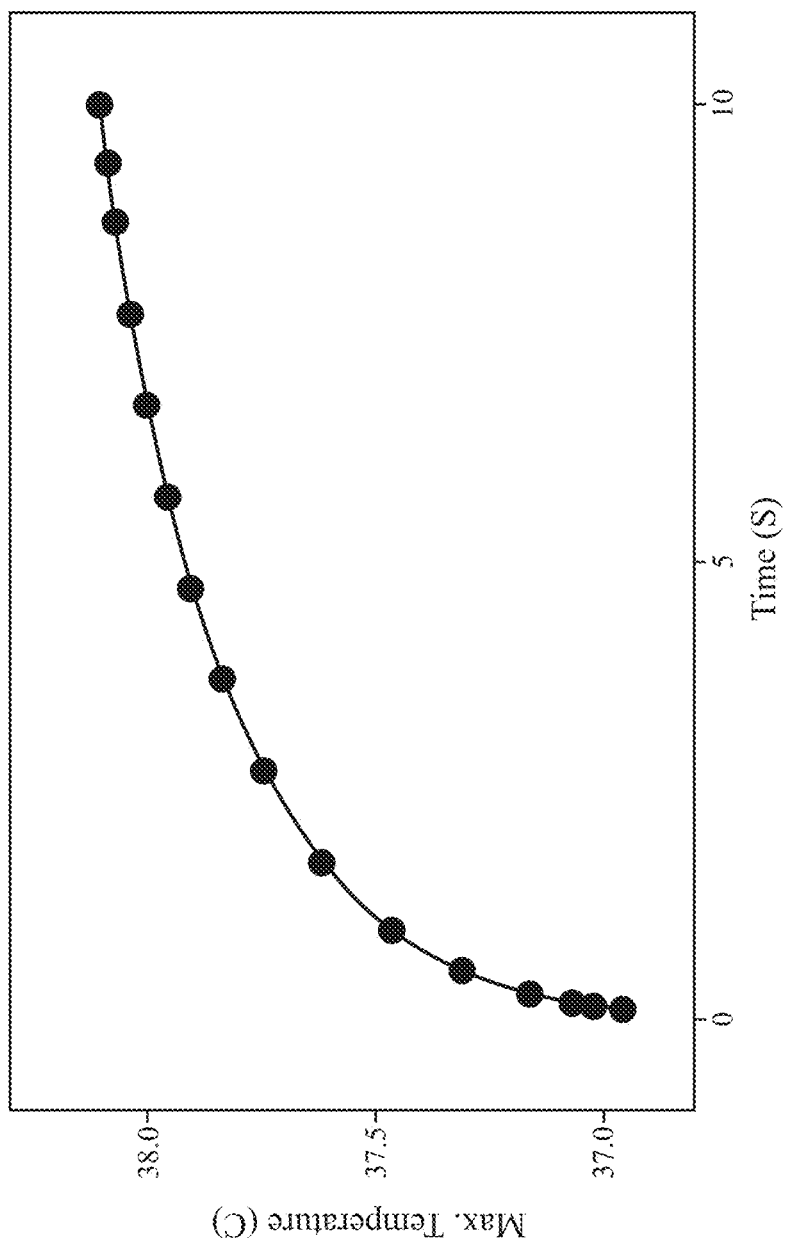
FIG. 37 is a graph illustrating a maximum temperature profile of the microprobe model shown in FIG. 35 over time.

FIG. 35 is an illustration of a three-dimensional model of the microprobe for heat transfer analysis given the heat dissipation from the two LEDs. The heat capacitance of each of the LEDs is shown in FIGS. 36A and 36B. In particular, FIG. 36A is a side-view temperature distribution after 1 second of LED illumination, and FIG. 36B is a side-view temperature distribution in steady-state after about 10 seconds. These temperature distributions show that the maximum temperature increase is about 1 degree on the LEDs, and temperature increase in adjacent pancreatic tissue is minimal. As shown in a time-series maximum temperature profile in FIG. 37, the temperature of the LEDs is stabilized in 10 seconds with continuous LED illumination.

Electrical and Optical Performance of a Microprobe with Three LEDs

Figure 38A:
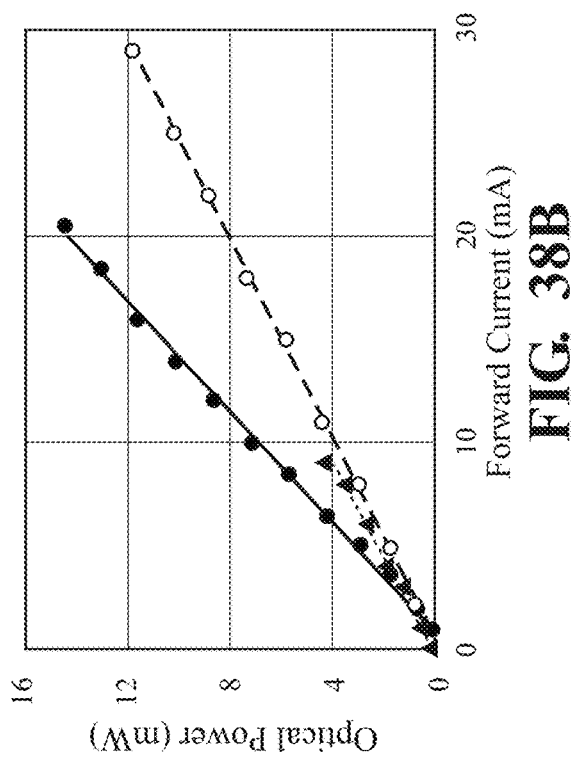
FIG. 38A is a graph showing the forward voltage (V) compared to forward current (mA) for three LEDs with different wavelengths of a fabricated microprobe.
Figure 38B:
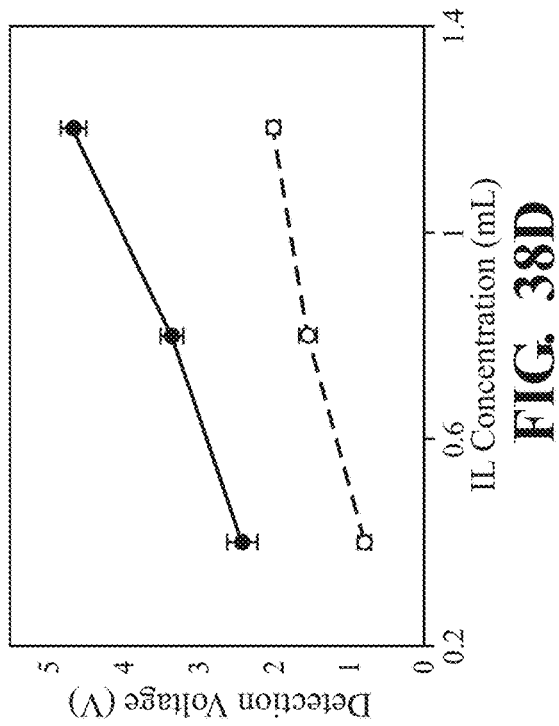
FIG. 38B is a graph of the forward current (mA) compared to the optical power (mW) for three LEDs with different wavelengths of a fabricated microprobe.
Figure 38C:
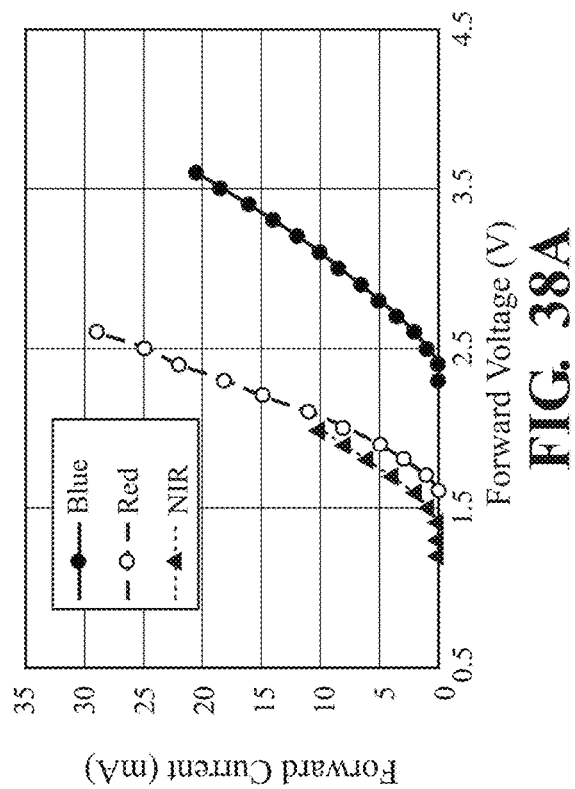
FIG. 38C is a graph showing emission wavelengths of three LEDs of a fabricated microprobe.
Figure 38D:
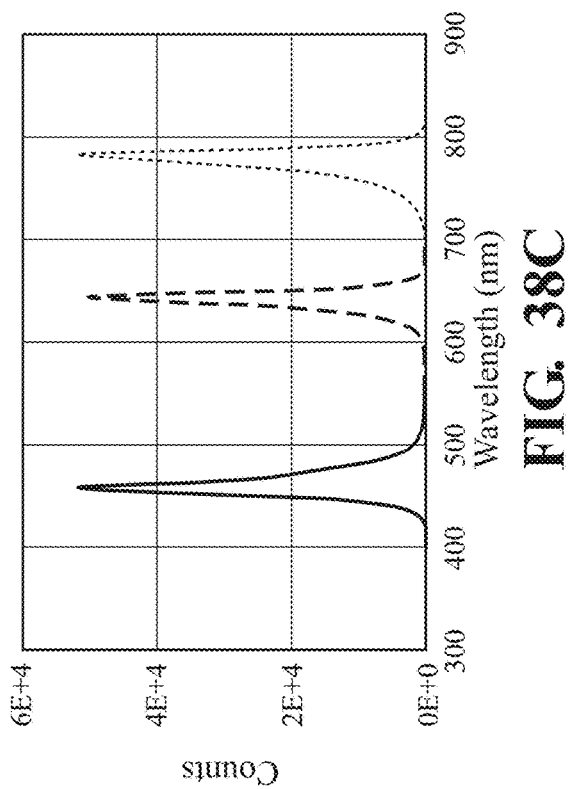
FIG. 38D is a graph showing a detection voltage (V) of a phototransistor of a fabricated microprobe compared to an intralipid concentration (mL).
Figures 39A, 39B, 39C, 39D, 39E, 39F, 39G, 39H:
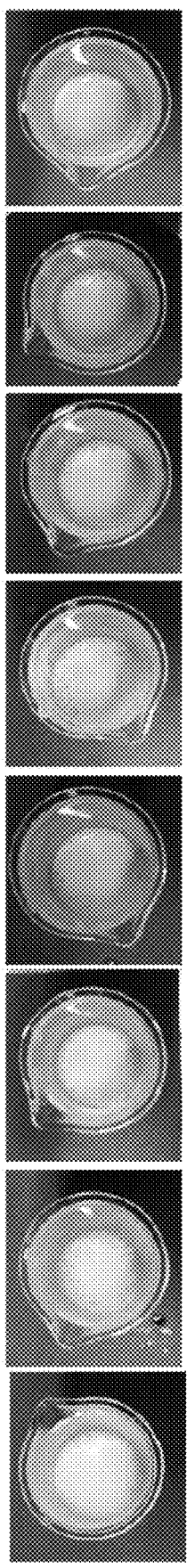
FIGS. 39A-39H are photographs of a set of liquid phantoms including 5 μM of hemoglobin to a base including a predetermined concentration of a 1 μm-sized polystyrene microsphere and deionized water to mimic a scattering coefficient of human pancreatic tissues.

A microprobe was prepared including a phototransistor and three LEDs with different wavelengths. In particular, the microprobe has a blue LED, a red LED, and a near infra-red (NIR) LED. The optical and electrical performances of the microprobe are characterized as shown in FIGS. 38A-38D. FIG. 38A is a graph showing the forward voltage (V) compared to forward current of three LEDs with different wavelengths. FIG. 38B is a graph showing a linear relationship between forward current (mA) and optical power (mW) of the three LEDs. FIG. 38C is a graph showing emission wavelengths of the three LEDs measured using a spectrophotometer. In FIG. 38C, the peak wavelengths are at 478 nm for the blue LED, 649 nm for the red LED, and 785 nm for the NIR LED. Further, the blue LED has a full-width-half-maximum wavelength of 40 nm, the red LED has a full-width-half-maximum wavelength of 50 nm, and the NIR LED has a full-width-half-maximum wavelength of 50 nm. FIG. 38D is a graph showing the detection voltage (V) detected by the phototransistor compared to the intralipid (IL) concentration (mL). As shown in FIG. 38D, the detection voltage of the phototransistor increases with an increase in the scatterer (intralipid) concentration under consistent power of the blue and red LEDs. All of the data shown in FIGS. 38A-38D show that the individual components of the microprobe are working properly.

Verification of the Microprobe with Three LEDs with Varying Wavelengths

The microprobe fabricated with three LEDs (blue, red, and NIR) is verified using a set of liquid phantoms with varying hemoglobin concentrations in comparison with a conventional wavelength-resolved reflectance spectroscopy system. Photographs of the liquid phantoms with varying hemoglobin concentrations are shown in FIGS. 39A-39H. The liquid phantoms are made by adding 5 to 40 μM of hemoglobin (i.e., 5 μM of hemoglobin for the phantom shown in FIG. 39A, 10 μM of hemoglobin for the phantom shown in FIG. 39B, 15 μM of hemoglobin for the phantom shown in FIG. 39C, and so on). The hemoglobin is added to a predetermined concentration of a 1 μm-sized polystyrene microsphere mixed with dionized water to mimic a scattering coefficient of human pancreatic tissues (about 10 cm$^{-1}$).

Figure 40:
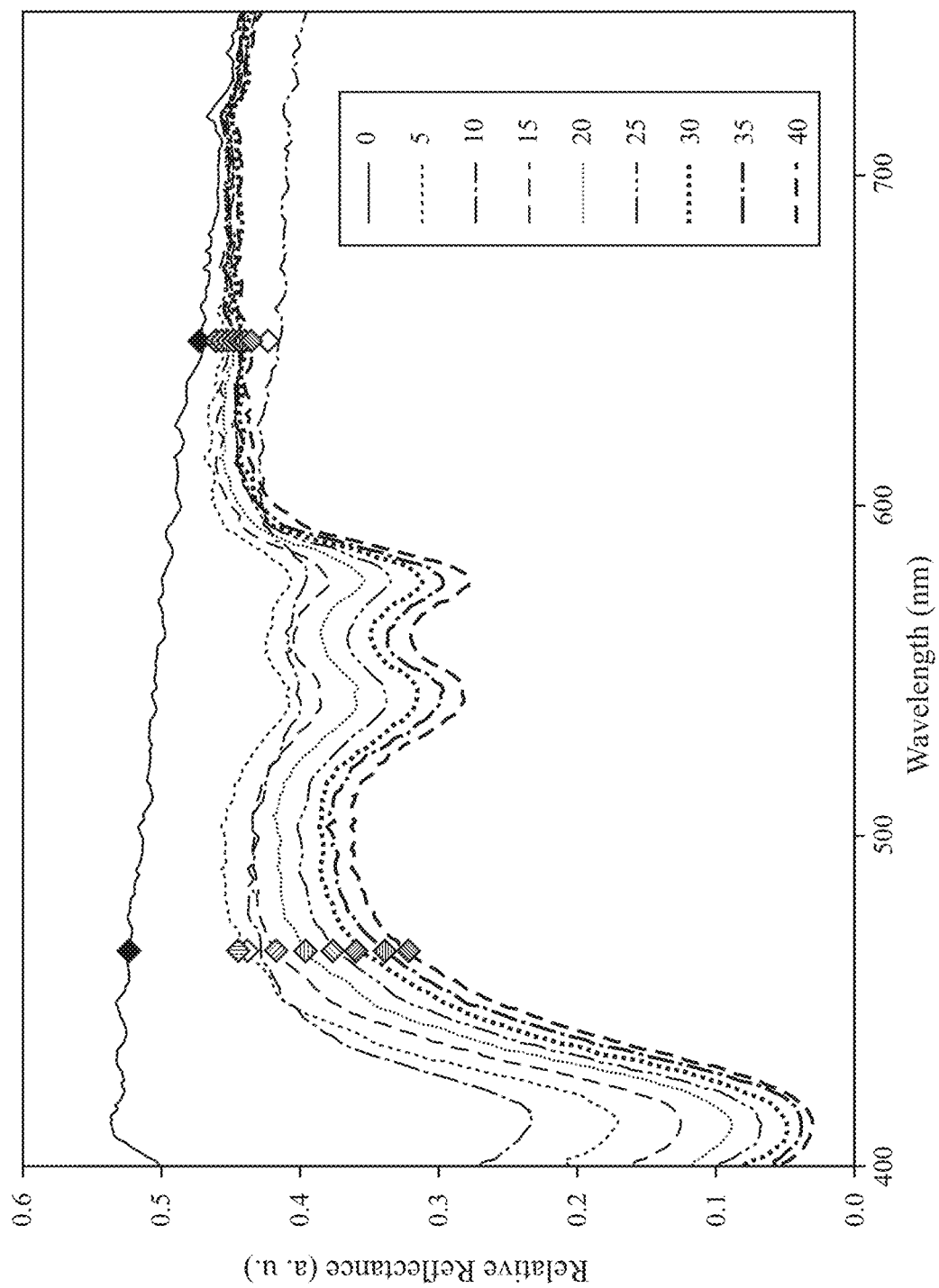
FIG. 40 is a graph showing a measured relative reflectance at each wavelength (nm) for each liquid phantom shown in FIGS. 39A-39H.

The relative reflectance of the hemoglobin in the liquid phantoms is compared to the wavelength (nm). As shown in FIG. 40, the relative reflectance of the hemoglobin at both wavelengths, which was measured using reflectance spectroscopy, are comparable with the varying hemoglobin concentrations. FIG. 40 also shows that as the hemoglobin concentration increases, the reflectance intensity decreases.

Figure 42:
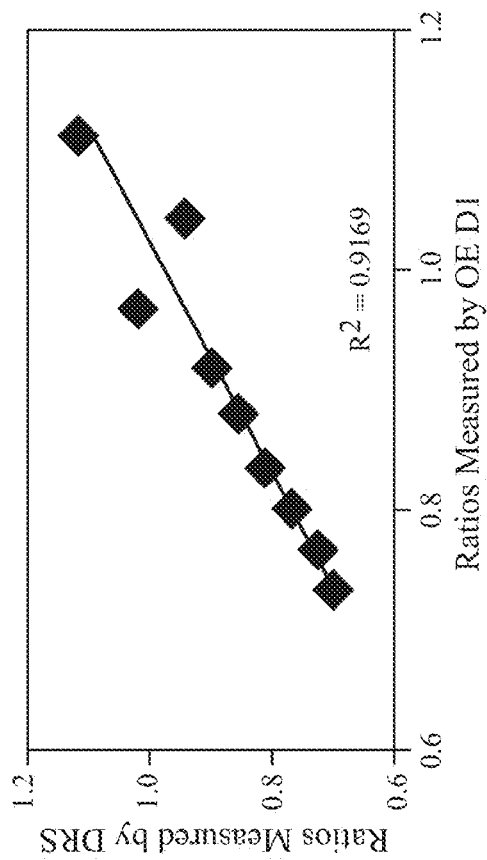
FIG. 42 is a graph of the ratios measured by Diffuse Reflectance Spectroscopy (DRS) compared to the ratios measured by a subunit of a fabricated microprobe.
Figure 41:
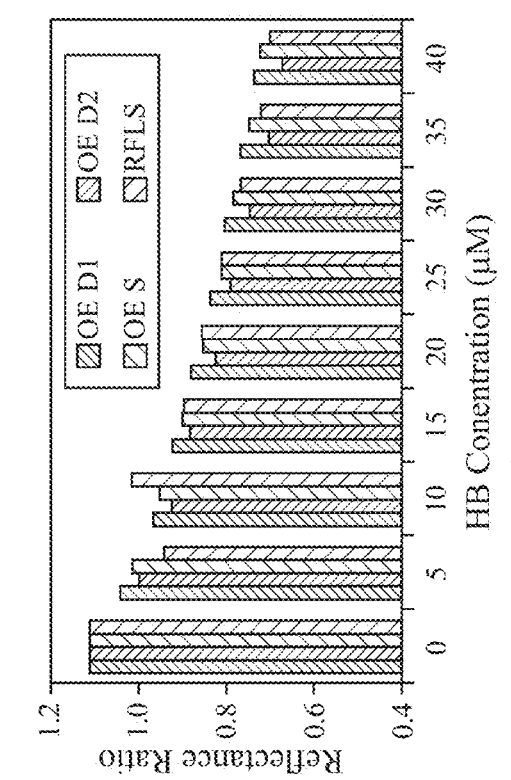
FIG. 41 is a graph of the hemoglobin concentration (μM) of the liquid phantoms in FIGS. 39A-39H compared to the reflectance ratio.

A microprobe was fabricated having two sensing subunits (OE D1 and OE D2), and another microprobe was fabricated having a single sensing unit (OE S). FIG. 41 is a graph showing the relationship between the hemoglobin concentration of the several phantoms and the reflectance ratio. As shown in FIG. 41, the reflectance ratios decrease as the hemoglobin (HB) concentration increases for each sensing unit tested. FIG. 42 shows that although the absolute ratios are different by about 10% between two modalities, the ratios are still similar (r=0.99).

Validation of the Microprobe in Ex Vivo Measurements

Figure 43A:
FIGS. 43A-43C are photographs of freshly excised human pancreas tissue being measured utilizing a fabricated microprobe with a dual sensing unit.
Figure 43B:
Figure 43C:

The microprobe fabricated with two sensing units is validated in ex vivo measurements on resected human pancreas tissue during pancreatic surgery. A total of four patients and twenty-two sites were tested. Photographs showing freshly excised human pancreas tissue measured using the microprobe, with the tissue containing pancreatic cancer in FIG. 43A, normal pancreas tissue shown in FIG. 43B, and tissue containing chronic pancreatitis in FIG. 43C.

Figure 45A:
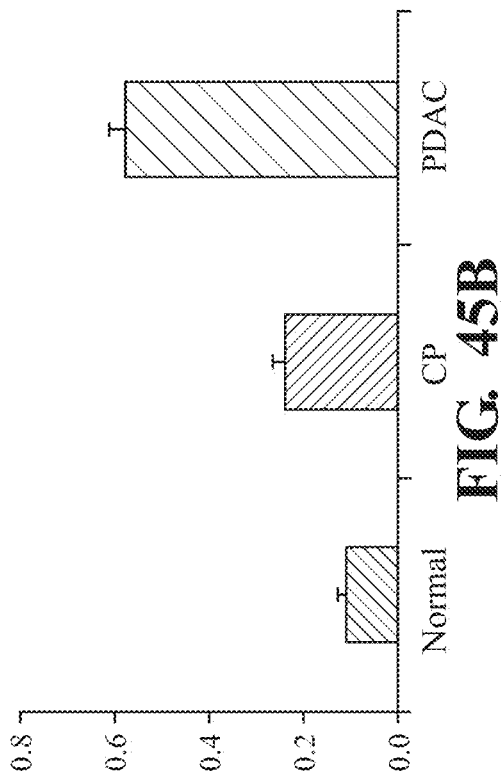
FIGS. 45A and 45B are bar graphs showing the reflectance ratios for normal tissue, tissue with chronic pancreatitis (CP), and tissue with pancreatic cancer (i.e., pancreatic ductal adenocarcinoma (PDAC)).
Figure 45B:
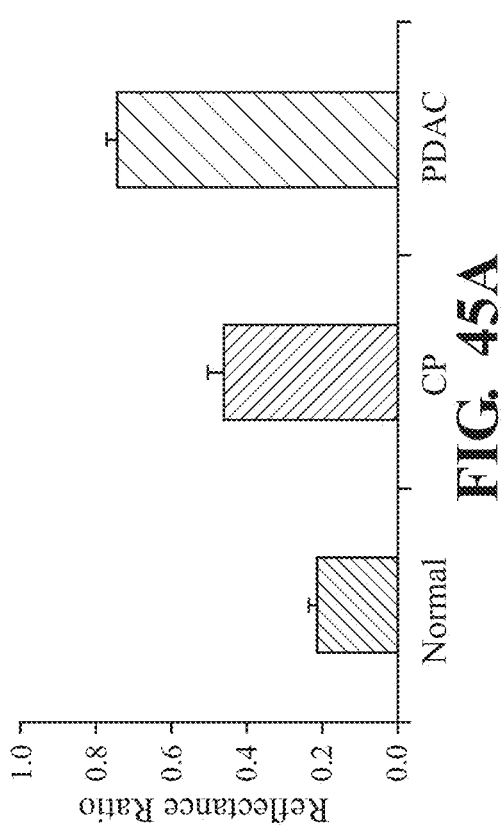
Figure 44:
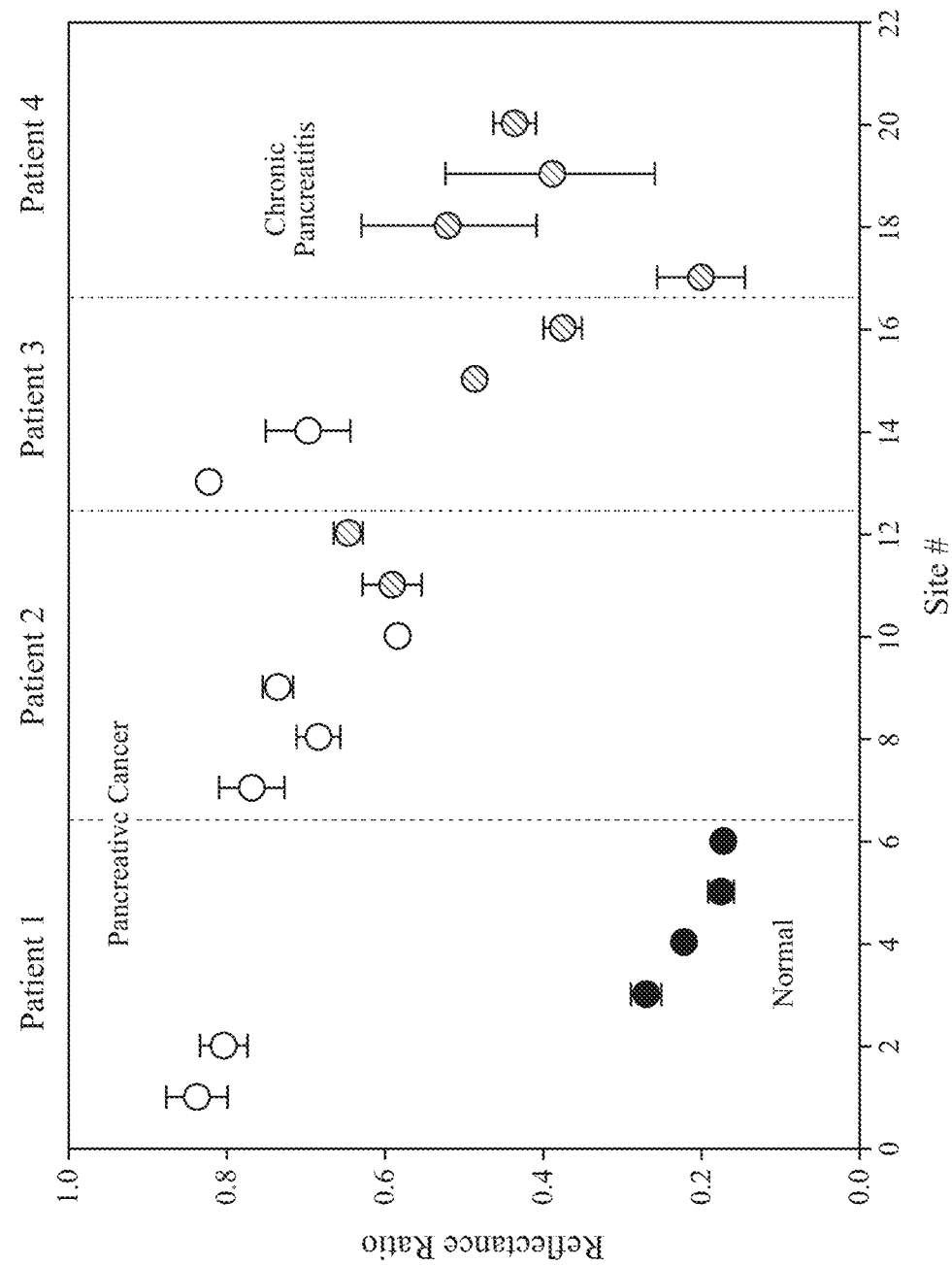
FIG. 44 is a scatter plot of reflectance ratios acquired by one of the subunits of the fabricated microprobe used in the photographs in FIGS. 43A-43C.

FIG. 44 is a scatter plot of reflectance ratios acquired by a subunit of the microprobe from all twenty-two sites of the four patients tested. FIG. 45A is a graph showing the measured reflectance ratios from one of the subunits of the microprobe distinguishing between normal pancreas tissue, tissue with chronic pancreatitis, and pancreas tissue with cancer. FIG. 45B is a graph showing the measured reflectance ratios from the other subunit of the microprobe distinguishing between normal pancreas tissue, tissue with chronic pancreatitis, and pancreas tissue with cancer.

It is believed that the optoelectronic microprobe of the present disclosure has the potential to revolutionize minimally-invasive tissue optical spectroscopy. The microprobe is an integrated optoelectronic system for EUS-FNA compatible tissue diagnosis. Further, quantitative analysis metrics have been developed from data collected during the clinical pilot study of freshly-excised pancreatic tissues. Ratiometric analysis determined that the three most common tissue types (normal, chromic pancreatitis, and adenocarcinoma) can each be distinguished from one another. The microprobe can also provide enhanced accuracy of diagnosis and volumetrically mapped tissue assessment by rapidly measuring multiple tissue sites, which is unlike current EUS-FNA which requires multiple needle passes into the tissue for a single aspirate collection. At each tissue side measured, two optical measurements can be simultaneously collected in less than 1 second, and these optical measurements are independent of motion artifacts and are suitable for clinical endoscopic use. Yet further, the microprobe reduces cost and instrumentation footprint with comparable (or even superior) optical performance and durability compared to standard optical-fiber-based systems. Each fabricated microprobe undergoes standardized validation testing with Erlangen™ Endo-Trainer to verify mechanical stability and optical performance with pancreas-simulating phantoms prior to human endoscope use. Furthermore, while the microprobe has been described above for diagnostics of pancreatic cancer, it is believed that the microprobe may also be used for other FNA procedures, including those performed during lung and breast cancer staging.

Furthermore, optical diagnostics may enhance the technical capability of the endoscopist to provide a more accurate diagnosis and may dramatically alter clinical practice by improved triage of patients to an appropriate therapy with or without surgery. In addition to enhanced accuracy of diagnosis, the microprobe technology compatible with commercially-available FNA needles of the present disclosure provides volumetrically mapped tissue assessment by rapidly measuring multiple tissue sites. This is unlike EUS-FNA, which requires multiple needle passes into the tissue for a single aspirate collection. Accordingly, the microprobe technology of the present disclosure typically has the potential to address an important unmet need of pancreatic neoplasia diagnosis (with a low negative predictive value of cytology) by improving the diagnostic capability of EUS, thereby leading to improved triage of patients to appropriate therapy.

The aforementioned embodiments and description are non-limiting and merely represent various embodiments of this disclosure. Further, the present disclosure has been described in an illustrative manner, and it is to be understood that the terminology which has been used is intended to be in the nature of words of description rather than of limitation. It is now apparent to those skilled in the art that many modifications and variations of the present disclosure are possible in light of the above teachings. It is, therefore, to be understood that the invention may be practiced otherwise than as specifically described.

What is claimed is:

1. A system for analyzing tissue, said system comprising:
a platform defining a longitudinal axis and having a length along said longitudinal axis; and
an optical sensing unit coupled to said platform with said optical sensing unit having a detector and a plurality of light sources electrically isolated from said detector with said optical sensing unit defining an optical axis parallel to said longitudinal axis, wherein said plurality of light sources includes at least one first light source and at least one second light source, and said detector being disposed between said first and second light sources along said optical axis, said optical sensing unit obtaining optical data for tissue analysis,
wherein said platform is a microprobe and said system further comprises a tissue aspiration needle with said microprobe being carried by said tissue aspiration needle.

2. The system as set forth in claim 1 wherein said at least one first light source includes a plurality of first light sources and wherein said at least one second light source includes a plurality of second light sources, with at least one of said first and second plurality of light sources arranged in parallel.

3. The system as set forth in claim 1 wherein said at least one first light source includes a plurality of first light sources and wherein said at least one second light source includes a plurality of second light sources with at least one of said first and second plurality of light sources arranged in series.

4. The system as set forth in claim 1 wherein said optical sensing unit is one of a plurality of optical sensing units coupled to said microprobe with said plurality of optical sensing units being linearly arranged along said optical axis.

5. The system as set forth in claim 4 wherein said plurality of optical sensing units includes at least two optical sensing units.

6. The system as set forth in claim 4 wherein said plurality of optical sensing units includes from two to twenty optical sensing units.

7. The system as set forth in claim 4 wherein said microprobe has first and second opposing surfaces each extending along said length and said plurality of optical sensing units includes at least one optical sensing unit coupled to each of said first and second opposing surfaces of said microprobe.

8. The system as set forth in claim 1 wherein each of said first and second light sources is a µLED emitting light within the visible spectrum.

9. The system as set forth in claim 8 wherein said first light source is a µLED emitting a red light and said second light source is a µLED emitting a blue light.

10. The system as set forth in claim 1 wherein said detector is chosen from a photodiode, a photodetector, and a phototransistor and said detector has a peak spectroscopic sensitivity of from about 850 to 900 nm.

11. The system as set forth in claim 1 wherein said first and second light sources are separated by a distance from about 0.4 to 5 mm along said optical axis, measured from the center of said first light source to the center of said second light source.

12. The system as set forth in claim 1 wherein said optical data is reflectance data.

13. The system as set forth in claim 12 further comprising a computer including an application containing computer-readable instructions causing the computer to utilize said reflectance data to analyze the tissue.

14. The system as set forth in claim 1 wherein said optical data is fluorescence data and said system further comprises a filter adjacent said detector for cutting a wavelength of light for measuring said fluorescence data.

15. A system for analyzing tissue, said system comprising:
a tissue aspiration needle defining a cavity having an opening; and
a microprobe disposed within said cavity and carried by said tissue aspiration needle with said microprobe defining a longitudinal axis and having a length along said longitudinal axis,
said microprobe having a platform and a plurality of optical sensing units coupled to said platform with said optical sensing units defining an optical axis parallel to said longitudinal axis and linearly arranged along said length and along said optical axis, said optical sensing units being exposed through said opening of said cavity, with each of said sensing units having first and second light sources and a detector arranged between and electrically isolated from said first and second light sources along said optical axis;
wherein said plurality of sensing units obtain optical data substantially simultaneously for analyzing the tissue.

16. The system as set forth in claim 15 wherein said first light source is a µLED emitting a red light and said second light source is a µLED emitting a blue light.

17. The system as set forth in claim 15 wherein said microprobe further includes a printed circuit board coupled to said platform, and said plurality of optical sensing units coupled to said printed circuit board.

18. A method of analyzing tissue utilizing a system comprising a platform defining a longitudinal axis and having a length along said longitudinal axis and an optical sensing unit coupled to the platform with the optical sensing unit defining an optical axis parallel to the longitudinal axis and with the optical sensing unit having a detector and a plurality of light sources electrically isolated from the detector, wherein the plurality of light sources includes at least one first light source and at least one second light source with the detector being disposed between the first and second light sources along the optical axis, wherein said platform is a microprobe and said system further comprises a tissue aspiration needle with said microprobe being carried by said tissue aspiration needle, said method comprising the steps of:

directing a light from the first and second light sources toward the tissue;

obtaining optical data while the light is being directed toward the tissue;

utilizing the optical data to analyze the tissue.

19. The method as set forth in claim 18 wherein the step of directing the light is further defined as directing a red light from the first light source and a blue light from the second light source.

20. The method as set forth in claim 18 wherein the step of obtaining the optical data is further defined as obtaining optical reflectance data.

21. The method as set forth in claim 18 wherein the system further includes a filter adjacent the detector and the step of obtaining the optical data is further defined as obtaining fluorescence data.

\* \* \* \* \*